US012722002B2

(12) United States Patent
Gerasimenko et al.

(10) Patent No.: US 12,722,002 B2
(45) **Date of Patent: *Sep. 1, 2026**

(54) MULTI-SITE TRANSCUTANEOUS ELECTRICAL STIMULATION OF THE SPINAL CORD FOR FACILITATION OF LOCOMOTION

(71) Applicant: The Regents of the University of California, Oakland, CA (US)

(72) Inventors: Yury P. Gerasimenko, Los Angeles, CA (US); Victor Reggie Edgerton, Los Angeles, CA (US); Roland R. Roy, Playa Vista, CA (US); Daniel C. Lu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/334,188

(22) Filed: Sep. 19, 2025

(65) Prior Publication Data

US 2026/0007883 A1 Jan. 8, 2026

Related U.S. Application Data

(63) Continuation of application No. 19/214,843, filed on May 21, 2025, which is a continuation of application
(Continued)

(51) Int. Cl.
*A61N 1/36* (2006.01)
*A61K 31/00* (2006.01)
(Continued)

(52) U.S. Cl.
CPC .......... *A61N 1/36003* (2013.01); *A61K 31/00* (2013.01); *A61K 31/197* (2013.01);
(Continued)

(58) Field of Classification Search
CPC .............. A61N 1/0456; A61N 1/36003; A61N 1/36034; A61K 31/00; A61K 31/197; A63B 2213/004; G16H 20/40
See application file for complete search history.

(56) References Cited

U.S. PATENT DOCUMENTS 2,868,343 A 1/1959 Sproul
3,543,761 A 12/1970 Bradley
(Continued)

FOREIGN PATENT DOCUMENTS

AU 2012204526 B2 5/2016
CA 2649663 A1 11/2007
(Continued)

OTHER PUBLICATIONS

Canadian Office Action in counterpart Canadian Patent Application No. 2906779 mailed Apr. 9, 2021, 4 pages.
(Continued)

*Primary Examiner* — Benjamin J Klein
(74) *Attorney, Agent, or Firm* — Mark S. Cohen; PEARL COHEN LLP

(57) ABSTRACT

In various embodiments, systems and methods for stimulation of the spinal cord to improve and restore upper extremity motor function in a subject having paralysis due to a spinal cord injury are provided. In some embodiments, the systems and methods involve administration of transcutaneous electrical spinal cord stimulation (tSCS) to the subject at a frequency and intensity that induces improved control of movement of the upper limbs of the subject.

26 Claims, 8 Drawing Sheets

Related U.S. Application Data

No. 17/837,913, filed on Jun. 10, 2022, now Pat. No. 12,311,169, which is a continuation of application No. 15/975,678, filed on May 9, 2018, now Pat. No. 11,400,284, which is a continuation of application No. 14/775,618, filed as application No. PCT/US2014/029340 on Mar. 14, 2014, now Pat. No. 9,993,642.

(60) Provisional application No. 61/802,034, filed on Mar. 15, 2013.

(51) Int. Cl.
*A61K 31/197* (2006.01)
*A61N 1/04* (2006.01)
*G16H 20/40* (2018.01)

(52) U.S. Cl.
CPC ....... *A61N 1/0456* (2013.01); *A61N 1/36034* (2017.08); *G16H 20/40* (2018.01); *A63B 2213/004* (2013.01)

(56) References Cited

U.S. PATENT DOCUMENTS 3,650,277 A 3/1972 Sjostrand et al.
3,653,518 A 4/1972 Polen
3,662,758 A 5/1972 Glover
3,724,467 A 4/1973 Avery et al.
4,044,774 A 8/1977 Corbin et al.
4,102,344 A 7/1978 Conway et al.
4,141,365 A 2/1979 Fischell et al.
4,285,347 A 8/1981 Hess
4,303,904 A 12/1981 Chasek
4,340,063 A 7/1982 Maurer
4,340,216 A 7/1982 Murphy
4,356,902 A 11/1982 Murphy
4,379,462 A 4/1983 Borkan et al.
4,398,537 A 8/1983 Holmbo
4,402,501 A 9/1983 Lohman
4,410,175 A 10/1983 Shamp
4,414,986 A 11/1983 Dickhudt et al.
4,538,624 A 9/1985 Tarjan
4,549,556 A 10/1985 Tarjan et al.
4,559,948 A * 12/1985 Liss .................. A61N 1/36021 607/46
4,569,352 A 2/1986 Petrofsky et al.
4,573,481 A 3/1986 Bullara
4,574,789 A 3/1986 Forster
4,724,842 A 2/1988 Charters
4,742,054 A 5/1988 Naftchi
4,784,420 A 11/1988 Makino et al.
4,798,982 A 1/1989 Voorman
4,800,898 A 1/1989 Hess et al.
4,934,368 A 6/1990 Lynch
4,969,452 A 11/1990 Petrofsky et al.
5,002,053 A * 3/1991 Garcia-Rill ........ A61N 1/36003 607/61
5,018,631 A 5/1991 Reimer
5,031,618 A 7/1991 Mullett
5,066,272 A 11/1991 Eaton et al.
5,081,989 A 1/1992 Graupe et al.
5,121,754 A 6/1992 Mullett
5,284,151 A 2/1994 Onoda
5,337,908 A 8/1994 Beck, Jr.
5,344,439 A 9/1994 Otten
5,348,544 A 9/1994 Sweeney et al.
5,354,320 A 10/1994 Schaldach et al.
5,366,813 A 11/1994 Berlin
5,374,285 A 12/1994 Vaiani et al.
5,417,719 A 5/1995 Hull et al.
5,421,783 A 6/1995 Kockelman et al.
5,441,465 A 8/1995 Hefner et al.
5,443,486 A 8/1995 Hrdlicka et al.
5,476,441 A 12/1995 Durfee et al.
5,553,270 A 9/1996 Rosenbluth
5,562,718 A 10/1996 Palermo
5,571,141 A 11/1996 McNeil et al.
5,584,818 A 12/1996 Morrison
5,601,527 A 2/1997 Selkowitz
5,626,540 A 5/1997 Hall
5,630,836 A 5/1997 Prem et al.
5,643,330 A 7/1997 Holsheimer et al.
5,643,332 A 7/1997 Stein
5,667,461 A 9/1997 Hall
5,733,322 A 3/1998 Starkebaum
5,788,606 A 8/1998 Rich
5,814,018 A 9/1998 Elson et al.
5,819,962 A 10/1998 Okubo et al.
5,876,425 A 3/1999 Gord et al.
5,877,183 A 3/1999 Cincotta
5,948,004 A 9/1999 Weijand et al.
5,958,933 A 9/1999 Naftchi
5,983,141 A 11/1999 Sluijter et al.
5,984,368 A 11/1999 Cain
6,052,624 A 4/2000 Mann
6,058,331 A 5/2000 King
6,066,163 A 5/2000 John
6,080,087 A 6/2000 Bingham
6,104,957 A 8/2000 Alo et al.
6,115,634 A 9/2000 Donders et al.
6,122,548 A 9/2000 Starkebaum et al.
6,139,475 A 10/2000 Bessler et al.
6,168,948 B1 1/2001 Anderson et al.
6,182,843 B1 2/2001 Tax et al.
6,188,927 B1 2/2001 Lu et al.
6,236,892 B1 5/2001 Feler
6,280,640 B1 8/2001 Hurwitz et al.
6,281,207 B1 8/2001 Richter et al.
6,308,103 B1 10/2001 Gielen
6,309,401 B1 10/2001 Redko et al.
6,319,241 B1 11/2001 King et al.
D454,139 S 3/2002 Feldcamp
6,463,327 B1 * 10/2002 Lurie ................. A61M 16/209 607/42
6,464,208 B1 10/2002 Smith
6,470,213 B1 10/2002 Alley
6,490,486 B1 12/2002 Bradley
6,500,110 B1 12/2002 Davey et al.
6,503,231 B1 1/2003 Prausnitz et al.
6,505,074 B2 1/2003 Boveja et al.
6,516,227 B1 * 2/2003 Meadows .......... A61N 1/37247 607/46
6,551,849 B1 4/2003 Kenney
6,587,724 B2 7/2003 Mann
6,662,053 B2 12/2003 Borkan
6,666,831 B1 12/2003 Edgerton et al.
6,685,729 B2 2/2004 Gonzalez
6,748,276 B1 6/2004 Daignault, Jr. et al.
6,819,956 B2 11/2004 DiLorenzo
6,839,594 B2 1/2005 Cohen et al.
6,862,479 B1 3/2005 Whitehurst et al.
6,871,099 B1 3/2005 Whitehurst et al.
6,878,112 B2 4/2005 Linberg et al.
6,892,098 B2 5/2005 Ayal et al.
6,895,280 B2 5/2005 Meadows et al.
6,895,283 B2 5/2005 Erickson et al.
6,901,292 B2 5/2005 Hrdlicka et al.
6,937,891 B2 8/2005 Leinders et al.
6,950,706 B2 9/2005 Rodriguez et al.
6,975,907 B2 12/2005 Zanakis et al.
6,978,181 B1 12/2005 Snell
6,988,006 B2 1/2006 King et al.
6,999,820 B2 2/2006 Jordan
7,010,749 B2 3/2006 Hasha et al.
7,020,521 B1 3/2006 Brewer et al.
7,024,247 B2 4/2006 Gliner et al.
7,035,690 B2 4/2006 Goetz
7,047,084 B2 5/2006 Erickson et al.
7,065,408 B2 6/2006 Herman et al.
7,096,070 B1 8/2006 Jenkins et al.
7,099,718 B1 8/2006 Thacker et al.
7,110,820 B2 9/2006 Tcheng et al.

(56) References Cited

U.S. PATENT DOCUMENTS 7,125,388 B1 10/2006 Reinkensmeyer et al.
7,127,287 B2 10/2006 Duncan et al.
7,127,296 B2 10/2006 Bradley
7,127,297 B2 10/2006 Law et al.
7,135,497 B1 11/2006 Zeman et al.
7,146,221 B2 12/2006 Krulevitch et al.
7,149,773 B2 12/2006 Haller et al.
7,153,242 B2 12/2006 Goffer
7,184,837 B2 2/2007 Goetz
7,200,443 B2 * 4/2007 Faul .................. A61N 1/36017 607/45
7,209,787 B2 4/2007 DiLorenzo
7,228,179 B2 6/2007 Campen et al.
7,239,920 B1 7/2007 Thacker et al.
7,251,529 B2 7/2007 Greenwood-Van Meerveld
7,252,090 B2 8/2007 Goetz
7,313,440 B2 12/2007 Miesel
7,324,853 B2 1/2008 Ayal et al.
7,330,760 B2 2/2008 Heruth et al.
7,330,762 B2 2/2008 Boveja et al.
7,337,005 B2 2/2008 Kim et al.
7,337,006 B2 2/2008 Kim et al.
7,340,298 B1 3/2008 Barbut
7,377,006 B2 5/2008 Genoa et al.
7,381,192 B2 * 6/2008 Brodard ............... A61H 1/0255 601/5
7,415,309 B2 8/2008 McIntyre
7,450,992 B1 11/2008 Cameron
7,463,927 B1 12/2008 Chaouat
7,463,928 B2 12/2008 Lee et al.
7,467,016 B2 12/2008 Colborn
7,493,170 B1 2/2009 Segel et al.
7,496,404 B2 2/2009 Meadows et al.
7,502,652 B2 3/2009 Gaunt et al.
7,536,226 B2 5/2009 Williams et al.
D594,024 S 6/2009 King
D595,308 S 6/2009 King
7,544,185 B2 6/2009 Bengtsson
7,565,195 B1 7/2009 Kroll et al.
7,584,000 B2 9/2009 Erickson
7,590,454 B2 9/2009 Garabedian et al.
7,603,178 B2 10/2009 North et al.
7,620,502 B2 11/2009 Selifonov et al.
7,628,750 B2 12/2009 Cohen et al.
7,647,115 B2 1/2010 Levin et al.
7,660,636 B2 2/2010 Castel et al.
7,697,995 B2 4/2010 Cross, Jr. et al.
7,725,193 B1 5/2010 Chu
7,729,781 B2 6/2010 Swoyer et al.
7,734,340 B2 * 6/2010 De Ridder ......... A61N 1/36017 607/2
7,734,351 B2 6/2010 Testerman et al.
7,742,037 B2 6/2010 Sako et al.
7,769,463 B2 8/2010 Katsnelson
7,769,464 B2 8/2010 Gerber et al.
7,780,617 B2 8/2010 Tornatore et al.
7,797,057 B2 9/2010 Harris
7,801,600 B1 9/2010 Carbunaru et al.
7,801,601 B2 9/2010 Maschino et al.
7,813,803 B2 10/2010 Heruth et al.
7,813,809 B2 10/2010 Strother et al.
7,840,270 B2 11/2010 Ignagni et al.
7,856,264 B2 12/2010 Firlik et al.
7,861,872 B2 1/2011 Ng et al.
7,877,146 B2 1/2011 Rezai et al.
7,890,182 B2 2/2011 Parramon et al.
D638,439 S 5/2011 Cavanaugh et al.
7,949,395 B2 5/2011 Kuzma
7,949,403 B2 5/2011 Palermo et al.
7,987,000 B2 7/2011 Moffitt et al.
7,991,465 B2 8/2011 Bartic et al.
8,019,427 B2 9/2011 Moffitt
8,050,773 B2 11/2011 Zhu
8,063,087 B2 11/2011 Chow et al.
8,100,815 B2 1/2012 Balaker et al.
8,108,051 B2 1/2012 Cross, Jr. et al.
8,108,052 B2 1/2012 Boling
D656,153 S 3/2012 Imamura et al.
8,131,358 B2 3/2012 Moffitt et al.
8,135,473 B2 3/2012 Miesel et al.
8,155,750 B2 4/2012 Jaax et al.
8,168,481 B2 5/2012 Hanaoka et al.
8,170,660 B2 5/2012 Dacey, Jr. et al.
8,190,262 B2 5/2012 Gerber et al.
8,195,304 B2 6/2012 Strother et al.
8,214,048 B1 7/2012 Whitehurst et al.
8,224,453 B2 7/2012 De Ridder
8,229,565 B2 7/2012 Kim et al.
8,238,666 B2 8/2012 Besley et al.
8,239,038 B2 8/2012 Wolf, II
8,260,436 B2 9/2012 Gerber et al.
8,265,770 B2 9/2012 Toy et al.
8,271,099 B1 9/2012 Swanson
8,295,936 B2 10/2012 Wahlstrand et al.
8,311,644 B2 11/2012 Moffitt et al.
8,326,569 B2 12/2012 Lee et al.
8,332,029 B2 12/2012 Glukhovsky et al.
8,332,047 B2 12/2012 Libbus et al.
8,332,053 B1 12/2012 Patterson et al.
8,346,366 B2 1/2013 Arle et al.
8,352,036 B2 1/2013 Dimarco et al.
8,355,791 B2 1/2013 Moffitt
8,355,797 B2 1/2013 Caparso et al.
8,364,273 B2 1/2013 De Ridder
8,369,961 B2 2/2013 Christman et al.
8,374,696 B2 2/2013 Sanchez et al.
D677,674 S 3/2013 Rampson et al.
8,407,576 B1 3/2013 Yin et al.
8,412,345 B2 4/2013 Moffitt
8,428,728 B2 * 4/2013 Sachs ................. A61N 1/36067 607/43
8,442,655 B2 5/2013 Moffitt et al.
8,452,406 B2 5/2013 Arcot-Krishnamurthy et al.
D684,991 S 6/2013 Wenz et al.
D684,996 S 6/2013 Wenz et al.
8,463,400 B2 6/2013 Hegi et al.
D688,259 S 8/2013 Pearcy et al.
D689,086 S 9/2013 Philopoulos
8,543,200 B2 9/2013 Lane et al.
D691,154 S 10/2013 Talbot et al.
D691,172 S 10/2013 Wujcik et al.
8,588,884 B2 11/2013 Hegde et al.
D694,763 S 12/2013 Edwards et al.
8,626,300 B2 1/2014 Demarais et al.
8,630,717 B2 1/2014 Olson et al.
8,700,145 B2 4/2014 Kilgard et al.
8,712,546 B2 4/2014 Kim et al.
D705,241 S 5/2014 Chen et al.
D707,235 S 6/2014 Arnold et al.
8,740,825 B2 6/2014 Ehrenreich et al.
8,750,957 B2 6/2014 Tang et al.
RE45,030 E 7/2014 Stevenson et al.
8,766,928 B2 7/2014 Weeldreyer et al.
8,768,472 B2 7/2014 Fang et al.
8,768,481 B2 7/2014 Lane
8,788,046 B2 * 7/2014 Bennett ............. A61N 1/36021 607/46
8,805,542 B2 8/2014 Tai et al.
8,836,368 B2 9/2014 Afshar et al.
8,847,548 B2 9/2014 Kesler et al.
8,849,410 B2 9/2014 Walker et al.
8,849,418 B2 9/2014 Daglow
8,897,870 B2 11/2014 De Ridder
8,903,502 B2 12/2014 Perryman et al.
D721,722 S 1/2015 Lee
8,957,549 B2 2/2015 Kesler et al.
D735,231 S 7/2015 Omiya
9,072,891 B1 7/2015 Rao
9,079,039 B2 7/2015 Carlson et al.
9,101,769 B2 8/2015 Edgerton et al.
D737,840 S 9/2015 Omiya
9,192,768 B2 11/2015 Yokoi et al.
9,205,259 B2 12/2015 Kim et al.
9,205,260 B2 12/2015 Kim et al.

(56) References Cited

U.S. PATENT DOCUMENTS 9,205,261 B2 12/2015 Kim et al.
9,248,291 B2 2/2016 Mashiach
D750,664 S 3/2016 Chen et al.
9,272,139 B2 3/2016 Hamilton et al.
9,272,143 B2 3/2016 Libbus et al.
9,283,391 B2 3/2016 Ahmed
9,314,630 B2 4/2016 Levin et al.
D758,398 S 6/2016 Yu et al.
9,358,384 B2 6/2016 Dubuclet
D760,753 S 7/2016 Cheng et al.
D762,234 S 7/2016 Li et al.
9,393,409 B2 7/2016 Edgerton et al.
D763,273 S 8/2016 Hwang et al.
9,409,023 B2 8/2016 Burdick et al.
9,409,030 B2 8/2016 Perryman et al.
9,415,218 B2 8/2016 Edgerton et al.
9,421,365 B2 8/2016 Sumners et al.
D769,302 S 10/2016 Rodriguez
D770,468 S 11/2016 Carlson et al.
D770,470 S 11/2016 Jin
9,520,887 B1 12/2016 Zhuang et al.
D780,768 S 3/2017 Carlson et al.
9,592,358 B2 3/2017 Miller et al.
9,592,385 B2 3/2017 Kaula et al.
9,597,517 B2 3/2017 Moffitt
D783,032 S 4/2017 Cashner et al.
9,610,442 B2 4/2017 Yoo et al.
D788,134 S 5/2017 Wong et al.
9,639,982 B2 5/2017 Craik et al.
9,656,076 B2 5/2017 Trier et al.
D789,963 S 6/2017 Agashiwala et al.
D794,667 S 8/2017 Havaldar et al.
9,717,908 B2 8/2017 Karunasiri
9,724,513 B2 8/2017 Lane et al.
9,802,052 B2 10/2017 Marnfeldt
9,812,875 B2 11/2017 Nejatali et al.
D806,717 S 1/2018 Bae et al.
9,895,545 B2 2/2018 Rao et al.
D816,708 S 5/2018 Riedel et al.
D819,681 S 6/2018 Fung et al.
9,993,642 B2 6/2018 Gerasimenko et al.
10,092,750 B2 10/2018 Edgerton et al.
D834,601 S 11/2018 Felt
10,124,166 B2 11/2018 Edgerton et al.
10,137,299 B2 11/2018 Lu et al.
D839,278 S 1/2019 Carlson et al.
D839,914 S 2/2019 Lee et al.
D841,017 S 2/2019 Bathla
D843,388 S 3/2019 Protzman et al.
10,406,366 B2 9/2019 Westlund et al.
10,449,371 B2 10/2019 Serrano Carmona
D874,491 S 2/2020 Kuo et al.
D874,507 S 2/2020 Martell et al.
D875,108 S 2/2020 Chitalia et al.
D875,752 S 2/2020 Nelson et al.
D877,753 S 3/2020 Chitalia et al.
10,751,533 B2 8/2020 Edgerton et al.
10,758,732 B1 9/2020 Heldman
10,773,074 B2 9/2020 Liu et al.
10,799,701 B2 10/2020 Lee
10,806,927 B2 10/2020 Edgerton et al.
10,806,935 B2 10/2020 Rao et al.
D904,437 S 12/2020 Chitalia et al.
D905,701 S 12/2020 Feng et al.
10,881,853 B2 1/2021 Edgerton et al.
10,898,719 B2 1/2021 Pivonka et al.
D912,074 S 3/2021 Giannino et al.
D926,784 S 8/2021 Carlson et al.
D928,188 S 8/2021 Giannino et al.
11,097,122 B2 8/2021 Lu
11,123,312 B2 9/2021 Lu et al.
11,129,983 B2 9/2021 Lo et al.
D939,549 S 12/2021 Miyai et al.
D947,216 S 3/2022 Leininger
11,266,850 B2 3/2022 Prouza et al.
11,298,533 B2 4/2022 Edgerton et al.
D962,245 S 8/2022 Thompson et al.
11,400,284 B2 8/2022 Gerasimenko et al.
11,491,336 B2 11/2022 Scheltienne et al.
11,511,116 B2 11/2022 Wagner et al.
11,515,733 B2 11/2022 Babakhani et al.
11,638,820 B2 5/2023 Edgerton et al.
11,684,774 B2 * 6/2023 Crosby .............. A61N 1/36003 606/41
11,691,015 B2 7/2023 Minassian et al.
D1,008,290 S 12/2023 Stapfer
D1,008,291 S 12/2023 Stapfer
D1,010,666 S 1/2024 Cai et al.
11,911,621 B2 2/2024 Ganty et al.
11,944,814 B2 4/2024 Lo et al.
11,957,910 B2 4/2024 Edgerton et al.
11,986,653 B2 5/2024 Lo et al.
11,992,684 B2 5/2024 Minassian et al.
12,018,135 B2 6/2024 Scher et al.
12,023,492 B2 7/2024 Edgerton et al.
12,076,301 B2 9/2024 Lu et al.
D1,044,827 S 10/2024 Tabrizi et al.
12,201,833 B2 1/2025 Edgerton et al.
12,214,198 B2 * 2/2025 Bennett .............. A61N 1/36021
12,268,878 B2 4/2025 Phillips et al.
12,415,079 B2 9/2025 Scheltienne et al.
2001/0016266 A1 8/2001 Okazaki et al.
2001/0032992 A1 10/2001 Wendt
2002/0042814 A1 4/2002 Fukasawa et al.
2002/0050456 A1 5/2002 Sheppard, Jr. et al.
2002/0052539 A1 5/2002 Haller et al.
2002/0055779 A1 * 5/2002 Andrews .............. A61N 1/0456 607/118
2002/0083240 A1 6/2002 Hoese et al.
2002/0111661 A1 8/2002 Cross et al.
2002/0115945 A1 * 8/2002 Herman ............... A61N 1/3604 601/15
2002/0123672 A1 9/2002 Christophersom et al.
2002/0138512 A1 9/2002 Buresh et al.
2002/0173505 A1 11/2002 Skogvall
2002/0175931 A1 11/2002 Holtz et al.
2002/0187260 A1 12/2002 Sheppard, Jr. et al.
2002/0188332 A1 12/2002 Lurie et al.
2002/0193843 A1 12/2002 Hill et al.
2003/0032992 A1 2/2003 Thacker et al.
2003/0078633 A1 4/2003 Firlik et al.
2003/0093021 A1 5/2003 Goffer
2003/0093131 A1 5/2003 Loeb et al.
2003/0097166 A1 5/2003 Krulevitch et al.
2003/0100933 A1 * 5/2003 Ayal .................. A61N 1/36007 607/48
2003/0113725 A1 6/2003 Small et al.
2003/0114894 A1 6/2003 Dar et al.
2003/0114899 A1 6/2003 Woods et al.
2003/0135253 A1 7/2003 Kokones et al.
2003/0139422 A1 7/2003 Teng
2003/0145759 A1 8/2003 Rodnunsky
2003/0158583 A1 * 8/2003 Burnett .................. A61N 2/006 607/2
2003/0199116 A1 10/2003 Tai et al.
2003/0200323 A1 10/2003 Dold et al.
2003/0208248 A1 11/2003 Carter et al.
2003/0220679 A1 11/2003 Han
2003/0233137 A1 12/2003 Paul, Jr.
2004/0039425 A1 2/2004 Greenwood-Van Meerveld
2004/0044380 A1 3/2004 Bruninga et al.
2004/0082979 A1 4/2004 Tong et al.
2004/0087286 A1 5/2004 Inoue et al.
2004/0088015 A1 5/2004 Casavant et al.
2004/0111118 A1 6/2004 Hill et al.
2004/0111126 A1 6/2004 Tanagho et al.
2004/0121528 A1 6/2004 Krulevitch et al.
2004/0122483 A1 6/2004 Nathan et al.
2004/0127954 A1 * 7/2004 McDonald, III ... A61N 1/36003 607/48
2004/0133248 A1 7/2004 Frei et al.
2004/0138518 A1 7/2004 Rise et al.
2004/0147975 A1 * 7/2004 Popovic ............. A61N 1/36003 607/48

(56) References Cited

U.S. PATENT DOCUMENTS

2004/0172027 A1 9/2004 Speitling et al.
2004/0172097 A1 9/2004 Brodard et al.
2004/0181263 A1 9/2004 Balzer et al.
2004/0192082 A1 9/2004 Wagner et al.
2004/0192834 A1 9/2004 Nakayoshi et al.
2004/0243204 A1 12/2004 Maghribi et al.
2004/0267320 A1 12/2004 Taylor et al.
2005/0004622 A1 1/2005 Cullen et al.
2005/0043775 A1 2/2005 John et al.
2005/0061315 A1 3/2005 Lee et al.
2005/0070982 A1 3/2005 Heruth et al.
2005/0075662 A1 4/2005 Pedersen et al.
2005/0075669 A1 4/2005 King
2005/0075678 A1 4/2005 Faul
2005/0075693 A1 4/2005 Toy et al.
2005/0080460 A1 4/2005 Wang et al.
2005/0090756 A1 4/2005 Wolf et al.
2005/0101827 A1 5/2005 Delisle
2005/0102007 A1 5/2005 Ayal et al.
2005/0113878 A1 5/2005 Gerber
2005/0113882 A1 5/2005 Cameron et al.
2005/0119713 A1 6/2005 Whitehurst et al.
2005/0125045 A1 6/2005 Brighton et al.
2005/0203588 A1 9/2005 King
2005/0205961 A1 9/2005 Doong
2005/0209655 A1 9/2005 Bradley et al.
2005/0231186 A1 10/2005 Saavedra Barrera et al.
2005/0239612 A1 10/2005 Keiser
2005/0246004 A1 11/2005 Cameron et al.
2005/0253273 A1 11/2005 Tai et al.
2005/0277999 A1 12/2005 Strother et al.
2005/0278000 A1 12/2005 Strother et al.
2006/0003090 A1 1/2006 Rodger et al.
2006/0007983 A1 1/2006 Tai et al.
2006/0015153 A1 1/2006 Gliner et al.
2006/0015470 A1 1/2006 Lauer et al.
2006/0016266 A1 1/2006 Weise et al.
2006/0018360 A1 1/2006 Tai et al.
2006/0041225 A1 2/2006 Wallace et al.
2006/0041295 A1 2/2006 Osypka
2006/0047325 A1* 3/2006 Thimineur ......... A61N 1/36071 607/45
2006/0075339 A1 4/2006 Tomita et al.
2006/0082626 A1 4/2006 Oikawa et al.
2006/0089696 A1 4/2006 Olsen et al.
2006/0095088 A1 5/2006 De Ridder
2006/0100671 A1 5/2006 De Ridder
2006/0111754 A1* 5/2006 Rezai ...................... A61M 5/00 607/41
2006/0122678 A1 6/2006 Olsen et al.
2006/0142337 A1 6/2006 Ikeura et al.
2006/0142816 A1 6/2006 Fruitman et al.
2006/0142822 A1* 6/2006 Tulgar ............... A61N 1/36021 607/45
2006/0149333 A1 7/2006 Tanagho et al.
2006/0149337 A1 7/2006 John
2006/0189453 A1 8/2006 Leblond
2006/0189839 A1 8/2006 Laniado et al.
2006/0195153 A1 8/2006 Diubaldi et al.
2006/0239482 A1 10/2006 Hatoum
2006/0241356 A1 10/2006 Flaherty
2006/0282127 A1* 12/2006 Zealear ................... A61B 5/24 607/42
2007/0004567 A1 1/2007 Shetty et al.
2007/0009968 A1 1/2007 Cunningham et al.
2007/0016097 A1 1/2007 Farquhar et al.
2007/0016266 A1 1/2007 Paul, Jr.
2007/0016268 A1 1/2007 Carter et al.
2007/0016329 A1 1/2007 Herr et al.
2007/0021513 A1 1/2007 Agee et al.
2007/0027495 A1 2/2007 Gerber
2007/0047852 A1 3/2007 Sharp et al.
2007/0049814 A1* 3/2007 Muccio ................ A61N 1/0468 600/388
2007/0055318 A1 3/2007 Forsberg et al.
2007/0055337 A1 3/2007 Tanrisever
2007/0060954 A1* 3/2007 Cameron ............. A61N 1/0553 607/2
2007/0060980 A1 3/2007 Strother et al.
2007/0067003 A1 3/2007 Sanchez et al.
2007/0073357 A1 3/2007 Rooney et al.
2007/0083240 A1 4/2007 Peterson et al.
2007/0100389 A1 5/2007 Jaax et al.
2007/0121702 A1 5/2007 Laguardia et al.
2007/0121709 A1 5/2007 Ittogi
2007/0129769 A1 6/2007 Bourget et al.
2007/0142874 A1 6/2007 John
2007/0142878 A1 6/2007 Krulevitch et al.
2007/0150023 A1 6/2007 Ignagni et al.
2007/0150034 A1 6/2007 Rooney et al.
2007/0156172 A1 7/2007 Alvarado
2007/0156179 A1 7/2007 S.E.
2007/0156200 A1 7/2007 Kornet et al.
2007/0168008 A1 7/2007 Olsen
2007/0179534 A1 8/2007 Firlik et al.
2007/0179579 A1 8/2007 Feler et al.
2007/0191709 A1 8/2007 Swanson
2007/0208381 A1 9/2007 Hill et al.
2007/0233204 A1 10/2007 Lima et al.
2007/0250119 A1 10/2007 Tyler et al.
2007/0255372 A1 11/2007 Metzler et al.
2007/0265621 A1 11/2007 Matthis et al.
2007/0265679 A1 11/2007 Bradley et al.
2007/0265691 A1 11/2007 Swanson
2007/0276449 A1 11/2007 Gunter et al.
2007/0276450 A1 11/2007 Meadows et al.
2007/0282378 A1 12/2007 Huang et al.
2007/0293910 A1 12/2007 Strother et al.
2008/0002227 A1 1/2008 Tsujimoto
2008/0004674 A1* 1/2008 King ................... A61N 1/0553 607/46
2008/0009927 A1 1/2008 Vilims
2008/0021513 A1 1/2008 Thacker et al.
2008/0027346 A1 1/2008 Litt et al.
2008/0046049 A1 2/2008 Skubitz et al.
2008/0051851 A1* 2/2008 Lin ......................... A61N 1/05 607/42
2008/0071325 A1 3/2008 Bradley
2008/0077192 A1* 3/2008 Harry .................. A61N 1/0476 42/84
2008/0092911 A1 4/2008 Schulman et al.
2008/0103579 A1 5/2008 Gerber
2008/0105185 A1 5/2008 Kuhlman
2008/0127031 A1 5/2008 Olsson et al.
2008/0140152 A1 6/2008 Imran et al.
2008/0140162 A1 6/2008 Goetz et al.
2008/0140169 A1 6/2008 Imran
2008/0147143 A1 6/2008 Popovic et al.
2008/0154329 A1 6/2008 Pyles et al.
2008/0183097 A1 7/2008 Leyde et al.
2008/0183224 A1 7/2008 Barolat
2008/0200749 A1 8/2008 Zheng et al.
2008/0202940 A1 8/2008 Jiang et al.
2008/0207985 A1 8/2008 Farone
2008/0208287 A1* 8/2008 Palermo ................ A61N 1/323 607/3
2008/0215113 A1 9/2008 Pawlowicz
2008/0221653 A1 9/2008 Agrawal et al.
2008/0224226 A1 9/2008 Suzuki et al.
2008/0228241 A1 9/2008 Sachs
2008/0228250 A1 9/2008 Mironer
2008/0234121 A1 9/2008 Kim et al.
2008/0234791 A1 9/2008 Arle et al.
2008/0255582 A1 10/2008 Harris
2008/0269854 A1 10/2008 Hegland et al.
2008/0275129 A1 11/2008 Lundstedt et al.
2008/0279896 A1 11/2008 Heinen et al.
2008/0287268 A1 11/2008 Hidler
2008/0294211 A1 11/2008 Moffitt
2008/0294226 A1 11/2008 Moffitt et al.
2008/0318733 A1 12/2008 Osler-Weppenaar
2009/0005844 A1 1/2009 Swoyer et al.
2009/0012436 A1 1/2009 Lanfermann et al.

(56) References Cited

U.S. PATENT DOCUMENTS

2009/0024186 A1 1/2009 Brockway
2009/0024997 A1 1/2009 Kobayashi
2009/0093854 A1 4/2009 Leung et al.
2009/0112281 A1 4/2009 Miyazawa et al.
2009/0118365 A1 5/2009 Benson, III et al.
2009/0131995 A1 5/2009 Sloan et al.
2009/0157141 A1 6/2009 Chiao et al.
2009/0198305 A1 8/2009 Naroditsky et al.
2009/0204173 A1 8/2009 Fang et al.
2009/0227925 A1 9/2009 Mcbean et al.
2009/0229166 A1 9/2009 Sawrie
2009/0254151 A1 10/2009 Anderson et al.
2009/0270960 A1 10/2009 Zhao et al.
2009/0281529 A1 11/2009 Carriazo
2009/0281599 A1 11/2009 Thacker et al.
2009/0293270 A1 12/2009 Brindley et al.
2009/0299166 A1 12/2009 Nishida et al.
2009/0299167 A1 12/2009 Seymour
2009/0306491 A1 12/2009 Haggers
2009/0312165 A1 12/2009 Rempe
2010/0004715 A1 1/2010 Fahey
2010/0006737 A1 1/2010 Colombo et al.
2010/0008782 A1 1/2010 Danescu et al.
2010/0010646 A1 1/2010 Drew et al.
2010/0016732 A1 1/2010 Wells et al.
2010/0023069 A1 1/2010 Moffitt et al.
2010/0023070 A1 1/2010 Moffitt et al.
2010/0023103 A1 1/2010 Elborno
2010/0029040 A1 2/2010 Nomoto
2010/0042193 A1 2/2010 Slavin
2010/0048358 A1 2/2010 Tchao et al.
2010/0057177 A1* 3/2010 Moffitt .............. A61N 1/36071 607/148
2010/0063568 A1 3/2010 Staunton et al.
2010/0070007 A1 3/2010 Parker et al.
2010/0070010 A1 3/2010 Simpson
2010/0087782 A1 4/2010 Ghaffari et al.
2010/0094800 A1 4/2010 Sharp
2010/0114205 A1 5/2010 Donofrio et al.
2010/0114239 A1 5/2010 Mcdonald, III
2010/0116526 A1 5/2010 Arora et al.
2010/0125313 A1 5/2010 Lee et al.
2010/0137238 A1 6/2010 Gan et al.
2010/0137938 A1 6/2010 Kishawi et al.
2010/0137943 A1* 6/2010 Zhu ................... A61N 1/36071 607/59
2010/0145428 A1 6/2010 Cameron et al.
2010/0152811 A1 6/2010 Flaherty
2010/0166546 A1 7/2010 Mahan et al.
2010/0168820 A1 7/2010 Maniak et al.
2010/0179562 A1 7/2010 Linker et al.
2010/0185253 A1* 7/2010 Dimarco ................. A61N 1/06 607/42
2010/0191307 A1 7/2010 Fang et al.
2010/0198298 A1* 8/2010 Glukhovsky ...... A61N 1/36017 607/46
2010/0217355 A1 8/2010 Tass et al.
2010/0217418 A1 8/2010 Fontanot
2010/0228310 A1 9/2010 Shuros et al.
2010/0241121 A1 9/2010 Logan et al.
2010/0241191 A1 9/2010 Testerman et al.
2010/0268299 A1 10/2010 Farone
2010/0274312 A1 10/2010 Alataris et al.
2010/0279606 A1 11/2010 Hillan et al.
2010/0280570 A1 11/2010 Sturm et al.
2010/0298905 A1 11/2010 Simon
2010/0298910 A1 11/2010 Carbunaru et al.
2010/0305660 A1 12/2010 Hegi et al.
2010/0312304 A1 12/2010 York et al.
2010/0318168 A1 12/2010 Bighetti
2010/0324699 A1 12/2010 Herr et al.
2010/0331925 A1 12/2010 Peterson
2011/0006793 A1 1/2011 Peschke et al.
2011/0009919 A1 1/2011 Carbunaru et al.
2011/0016081 A1 1/2011 Basak et al.
2011/0029040 A1 2/2011 Walker et al.
2011/0029044 A1 2/2011 Hyde et al.
2011/0034277 A1 2/2011 Brandes
2011/0034912 A1 2/2011 De Graff et al.
2011/0034977 A1 2/2011 Janik et al.
2011/0040349 A1* 2/2011 Graupe ............. A61N 1/36003 607/49
2011/0054567 A1 3/2011 Lane et al.
2011/0054568 A1 3/2011 Lane et al.
2011/0054570 A1 3/2011 Lane
2011/0054579 A1 3/2011 Kumar et al.
2011/0060461 A1 3/2011 Velliste et al.
2011/0077660 A1 3/2011 Janik et al.
2011/0082515 A1 4/2011 Libbus et al.
2011/0084489 A1 4/2011 Kaplan
2011/0093043 A1 4/2011 Torgerson et al.
2011/0112601 A1 5/2011 Meadows et al.
2011/0112611 A1 5/2011 Aghassian
2011/0118815 A1 5/2011 Kuzma et al.
2011/0125203 A1* 5/2011 Simon ................... A61N 2/006 607/2
2011/0130804 A1 6/2011 Lin et al.
2011/0152967 A1* 6/2011 Simon ................... A61N 2/006 607/45
2011/0160810 A1 6/2011 Griffith
2011/0166546 A1* 7/2011 Jaax .................. A61N 1/36082 607/46
2011/0184482 A1 7/2011 Eberman et al.
2011/0184488 A1 7/2011 De Ridder
2011/0184489 A1* 7/2011 Nicolelis ............ A61N 1/36025 607/48
2011/0201944 A1 8/2011 Higgins et al.
2011/0202107 A1 8/2011 Sunagawa et al.
2011/0208265 A1 8/2011 Erickson et al.
2011/0213266 A1 9/2011 Williams et al.
2011/0218590 A1 9/2011 Degiorgio et al.
2011/0218594 A1 9/2011 Doron et al.
2011/0224153 A1 9/2011 Levitt et al.
2011/0224665 A1 9/2011 Crosby et al.
2011/0224752 A1 9/2011 Rolston et al.
2011/0224753 A1 9/2011 Palermo et al.
2011/0224755 A1 9/2011 Arie et al.
2011/0224757 A1 9/2011 Zdeblick et al.
2011/0230101 A1 9/2011 Tang et al.
2011/0230701 A1* 9/2011 Simon ................. A61N 1/0456 607/46
2011/0230702 A1* 9/2011 Honour .................... A61N 1/40 607/42
2011/0230747 A1 9/2011 Rogers et al.
2011/0230808 A1 9/2011 Lisowski
2011/0231326 A1 9/2011 Marino
2011/0237221 A1 9/2011 Prakash et al.
2011/0237921 A1 9/2011 Askin et al.
2011/0245734 A1 10/2011 Wagner et al.
2011/0260126 A1 10/2011 Willis
2011/0270360 A1 11/2011 Harris et al.
2011/0276107 A1* 11/2011 Simon ..................... A61N 2/02 607/46
2011/0288609 A1 11/2011 Tehrani et al.
2011/0295100 A1 12/2011 Hegde et al.
2012/0006793 A1 1/2012 Swanson
2012/0011222 A1 1/2012 Yasukawa et al.
2012/0011950 A1 1/2012 Kracke
2012/0013041 A1 1/2012 Cao et al.
2012/0013126 A1 1/2012 Molloy
2012/0016448 A1 1/2012 Lee
2012/0016453 A1 1/2012 Feler et al.
2012/0018249 A1 1/2012 Mehr
2012/0022371 A1 1/2012 Summerton
2012/0022551 A1 1/2012 Staunton et al.
2012/0029528 A1 2/2012 Macdonald et al.
2012/0035684 A1 2/2012 Thompson et al.
2012/0036552 A1 2/2012 Dare et al.
2012/0041518 A1 2/2012 Kim et al.
2012/0052432 A1 3/2012 Matsuura
2012/0053645 A1 3/2012 Ayanoor-Vitikkate et al.
2012/0059432 A1 3/2012 Emborg et al.
2012/0071250 A1 3/2012 O'Neil et al.

(56) References Cited

U.S. PATENT DOCUMENTS

2012/0071950 A1 3/2012 Archer
2012/0083709 A1 4/2012 Parker et al.
2012/0101326 A1* 4/2012 Simon ................ A61N 1/36007 607/40
2012/0109251 A1 5/2012 Lebedev et al.
2012/0109295 A1 5/2012 Fan
2012/0116476 A1 5/2012 Kothandaraman
2012/0116478 A1* 5/2012 Buhlmann ........... A61B 5/4519 607/48
2012/0123223 A1 5/2012 Freeman et al.
2012/0123293 A1* 5/2012 Shah .................... A61N 1/0551 607/46
2012/0126392 A1 5/2012 Kalvesten et al.
2012/0136408 A1 5/2012 Grill et al.
2012/0143281 A1 6/2012 Birkill et al.
2012/0161531 A1 6/2012 Kim
2012/0161721 A1 6/2012 Neethimanickam
2012/0165899 A1 6/2012 Gliner
2012/0168397 A1 7/2012 Lim et al.
2012/0172222 A1 7/2012 Artigas Puerto
2012/0172246 A1 7/2012 Nguyen et al.
2012/0172510 A1 7/2012 Esseghir et al.
2012/0172946 A1 7/2012 Alataris et al.
2012/0179222 A1 7/2012 Jaax et al.
2012/0185020 A1* 7/2012 Simon .................... A61N 2/006 607/72
2012/0197338 A1 8/2012 Su et al.
2012/0203055 A1 8/2012 Pletnev
2012/0203131 A1 8/2012 Dilorenzo
2012/0203246 A1 8/2012 Staunton et al.
2012/0221073 A1 8/2012 Southwell et al.
2012/0232615 A1 9/2012 Barolat et al.
2012/0252380 A1 10/2012 Kawakita
2012/0252874 A1* 10/2012 Feinstein ................ A61P 25/00 514/44 A
2012/0259380 A1 10/2012 Pyles
2012/0265269 A1 10/2012 Lui
2012/0271315 A1 10/2012 Pianca et al.
2012/0271372 A1 10/2012 Osorio
2012/0277824 A1 11/2012 Li
2012/0277834 A1 11/2012 Mercanzini et al.
2012/0283697 A1 11/2012 Kim et al.
2012/0283797 A1 11/2012 De Ridder
2012/0302821 A1 11/2012 Burnett
2012/0310302 A1* 12/2012 Bennett .............. A61N 1/36071 607/46
2012/0310305 A1 12/2012 Kaula et al.
2012/0310315 A1 12/2012 Savage et al.
2012/0330321 A1 12/2012 Johnson et al.
2012/0330391 A1 12/2012 Bradley et al.
2013/0006322 A1* 1/2013 Tai ..................... A61N 1/36007 607/40
2013/0006793 A1 1/2013 O'Sullivan et al.
2013/0012853 A1* 1/2013 Brown ................. A41D 31/185 602/19
2013/0013041 A1 1/2013 Glukhovsky et al.
2013/0023972 A1 1/2013 Kuzma et al.
2013/0026640 A1 1/2013 Ito et al.
2013/0030312 A1 1/2013 Keel et al.
2013/0030319 A1 1/2013 Hettrick et al.
2013/0030501 A1 1/2013 Feler et al.
2013/0032508 A1 2/2013 Azuma
2013/0035745 A1* 2/2013 Ahmed .............. A61N 1/36103 607/66
2013/0041235 A1 2/2013 Rogers et al.
2013/0053734 A1 2/2013 Barriskill et al.
2013/0053922 A1* 2/2013 Ahmed .............. A61N 1/36071 607/45
2013/0066392 A1 3/2013 Simon et al.
2013/0066411 A1 3/2013 Thacker et al.
2013/0085317 A1* 4/2013 Feinstein ........... A61N 1/37247 600/14
2013/0085361 A1 4/2013 Mercanzini et al.
2013/0096640 A1 4/2013 Passover
2013/0096661 A1 4/2013 Greenberg et al.
2013/0096662 A1 4/2013 Swanson
2013/0110196 A1 5/2013 Alataris et al.
2013/0116604 A1 5/2013 Marilla et al.
2013/0116751 A1 5/2013 Moffitt et al.
2013/0123568 A1* 5/2013 Hamilton ................. A61N 2/02 600/13
2013/0123659 A1 5/2013 Bartol et al.
2013/0138167 A1 5/2013 Bradley et al.
2013/0150915 A1 6/2013 Kane et al.
2013/0154373 A1 6/2013 Lisuwandi et al.
2013/0158444 A1 6/2013 Herr et al.
2013/0165991 A1* 6/2013 Kim ......................... A61B 5/01 607/46
2013/0190143 A1 7/2013 Greenhill et al.
2013/0197408 A1 8/2013 Goldfarb et al.
2013/0204324 A1* 8/2013 Thacker ............. A61N 1/36075 607/46
2013/0211477 A1 8/2013 Cullen et al.
2013/0226263 A1 8/2013 Kelly et al.
2013/0237948 A1 9/2013 Donders et al.
2013/0245712 A1 9/2013 Simon et al.
2013/0253222 A1 9/2013 Nakao
2013/0253229 A1 9/2013 Sawant et al.
2013/0253299 A1* 9/2013 Weber ................ A61N 1/36107 607/45
2013/0253611 A1 9/2013 Lee et al.
2013/0268016 A1 10/2013 Xi et al.
2013/0268020 A1 10/2013 Rosenberg et al.
2013/0268021 A1 10/2013 Moffitt
2013/0268041 A1 10/2013 Schulte et al.
2013/0281890 A1* 10/2013 Mishelevich ...... A61N 1/36085 601/2
2013/0289446 A1 10/2013 Stone et al.
2013/0289650 A1 10/2013 Karlsson et al.
2013/0289664 A1 10/2013 Johanek
2013/0289667 A1 10/2013 Wacnik et al.
2013/0296965 A1 11/2013 Mokelke et al.
2013/0303873 A1* 11/2013 Voros .................. H05K 1/0283 604/20
2013/0304159 A1 11/2013 Simon et al.
2013/0310211 A1 11/2013 Wilton et al.
2013/0310911 A1* 11/2013 Tai ...................... A61N 1/0558 216/17
2013/0325081 A1 12/2013 Karst et al.
2013/0325083 A1 12/2013 Bharmi et al.
2013/0345780 A1 12/2013 Tabada et al.
2014/0005753 A1 1/2014 Carbunaru
2014/0031893 A1 1/2014 Walker et al.
2014/0031895 A1 1/2014 Rahimi et al.
2014/0046407 A1 2/2014 Ben-Ezra et al.
2014/0053401 A1 2/2014 Kuzma et al.
2014/0058292 A1 2/2014 Alford et al.
2014/0058490 A1 2/2014 Dimarco
2014/0059499 A1 2/2014 Kim et al.
2014/0066950 A1 3/2014 Macdonald et al.
2014/0067007 A1 3/2014 Drees et al.
2014/0067013 A1 3/2014 Kaula et al.
2014/0067354 A1 3/2014 Kaula et al.
2014/0074190 A1 3/2014 Griffith
2014/0081011 A1 3/2014 Vaught et al.
2014/0081071 A1 3/2014 Simon et al.
2014/0081345 A1 3/2014 Hershey
2014/0087922 A1 3/2014 Bayerlein et al.
2014/0088674 A1 3/2014 Bradley
2014/0100491 A1 4/2014 Hu et al.
2014/0100633 A1* 4/2014 Mann .................. A61N 1/0551 607/116
2014/0107397 A1 4/2014 Simon et al.
2014/0107398 A1 4/2014 Simon et al.
2014/0114374 A1 4/2014 Rooney et al.
2014/0114385 A1 4/2014 Nijhuis et al.
2014/0124713 A1 5/2014 Majumdar et al.
2014/0142652 A1 5/2014 Francois et al.
2014/0163640 A1 6/2014 Edgerton et al.
2014/0171961 A1 6/2014 Lacey et al.
2014/0172045 A1 6/2014 Yip et al.
2014/0172055 A1 6/2014 Venancio

(56) References Cited

U.S. PATENT DOCUMENTS

2014/0180361 A1 6/2014 Burdick et al.
2014/0200387 A1* 7/2014 Ahmed .................. A61N 1/205 600/9
2014/0201905 A1 7/2014 Glukhovsky
2014/0213842 A1 7/2014 Simon et al.
2014/0213844 A1 7/2014 Pilla et al.
2014/0228905 A1 8/2014 Bolea
2014/0236257 A1* 8/2014 Parker ...................... A61B 5/24 607/46
2014/0243923 A1 8/2014 Doan et al.
2014/0257016 A1* 9/2014 Ahmed .................... A61N 2/02 607/48
2014/0277271 A1 9/2014 Chan et al.
2014/0296752 A1 10/2014 Edgerton et al.
2014/0303685 A1 10/2014 Rosenberg et al.
2014/0303901 A1 10/2014 Sadeh
2014/0316484 A1 10/2014 Edgerton et al.
2014/0316503 A1 10/2014 Tai et al.
2014/0324118 A1 10/2014 Simon et al.
2014/0330067 A1 11/2014 Jordan
2014/0330335 A1 11/2014 Errico et al.
2014/0336722 A1 11/2014 Rocon De Lima et al.
2014/0339909 A1 11/2014 Sugawara
2014/0343623 A1 11/2014 Alves et al.
2014/0344740 A1 11/2014 Kaula et al.
2014/0357936 A1 12/2014 Simon et al.
2014/0359521 A1 12/2014 Lin et al.
2014/0371830 A1 12/2014 Howard et al.
2015/0005167 A1 1/2015 Jung et al.
2015/0005840 A1 1/2015 Pal et al.
2015/0012061 A1 1/2015 Chen
2015/0022143 A1 1/2015 Kim
2015/0032187 A1 1/2015 Ranu et al.
2015/0051674 A1 2/2015 Barner et al.
2015/0057717 A1 2/2015 Wu et al.
2015/0065559 A1 3/2015 Feinstein et al.
2015/0066111 A1 3/2015 Blum et al.
2015/0074997 A1 3/2015 Kuzma et al.
2015/0088212 A1 3/2015 De Ridder
2015/0094734 A1 4/2015 Staunton et al.
2015/0094791 A1 4/2015 Edgell et al.
2015/0120634 A1 4/2015 Tateno
2015/0126120 A1 5/2015 Chen
2015/0148878 A1 5/2015 Yoo et al.
2015/0151114 A1 6/2015 Black et al.
2015/0151126 A1 6/2015 Kishawi et al.
2015/0165226 A1 6/2015 Simon et al.
2015/0174411 A1 6/2015 Ranu
2015/0182784 A1* 7/2015 Barriskill ............. A61H 1/0262 607/3
2015/0188592 A1 7/2015 Solondz
2015/0190200 A1* 7/2015 Courtine ................ A61B 5/721 604/20
2015/0190634 A1 7/2015 Rezai et al.
2015/0196231 A1 7/2015 Ziaie et al.
2015/0196241 A1 7/2015 Yekutieli
2015/0200561 A1 7/2015 Lee et al.
2015/0217120 A1 8/2015 Nandra et al.
2015/0224326 A1 8/2015 Toth et al.
2015/0231326 A1 8/2015 Milner et al.
2015/0231396 A1 8/2015 Burdick et al.
2015/0246216 A1 9/2015 Barker
2015/0265830 A1 9/2015 Simon et al.
2015/0268845 A1 9/2015 Endo
2015/0320632 A1 11/2015 Vallery et al.
2015/0328462 A1 11/2015 Griffith
2015/0343199 A1 12/2015 Wechter et al.
2015/0343205 A1 12/2015 Howard et al.
2016/0001096 A1 1/2016 Mishelevich
2016/0005538 A1 1/2016 Koyanagi et al.
2016/0030737 A1 2/2016 Gerasimenko et al.
2016/0030748 A1 2/2016 Edgerton et al.
2016/0030750 A1 2/2016 Bokil et al.
2016/0045727 A1 2/2016 Rezai et al.
2016/0045731 A1 2/2016 Simon et al.
2016/0067477 A1 3/2016 Dubuclet
2016/0074663 A1 3/2016 De Ridder
2016/0082261 A1 3/2016 Moffitt et al.
2016/0121109 A1 5/2016 Edgerton et al.
2016/0121114 A1 5/2016 Simon et al.
2016/0121116 A1 5/2016 Simon et al.
2016/0121121 A1 5/2016 Mashiach
2016/0136477 A1 5/2016 Bucher et al.
2016/0143588 A1 5/2016 Hoitink et al.
2016/0144167 A1 5/2016 Bakker et al.
2016/0144184 A1 5/2016 Marnfeldt
2016/0157389 A1 6/2016 Hwang
2016/0166828 A1 6/2016 Yu
2016/0175586 A1 6/2016 Edgerton et al.
2016/0197488 A1 7/2016 Hada et al.
2016/0213918 A1 7/2016 Howard et al.
2016/0220813 A1 8/2016 Edgerton et al.
2016/0228706 A1 8/2016 Hershey et al.
2016/0235977 A1 8/2016 Lu et al.
2016/0250461 A1 9/2016 Dubuclet
2016/0263376 A1 9/2016 Yoo et al.
2016/0271413 A1 9/2016 Vallejo et al.
2016/0279418 A1 9/2016 Courtine et al.
2016/0279429 A1 9/2016 Hershey et al.
2016/0291848 A1 10/2016 Hall et al.
2016/0310739 A1 10/2016 Burdick et al.
2016/0339239 A1 11/2016 Yoo et al.
2016/0367827 A1 12/2016 Tahmasian
2017/0007320 A1 1/2017 Levin et al.
2017/0007831 A1 1/2017 Edgerton et al.
2017/0014620 A9 1/2017 Staunton et al.
2017/0014622 A1 1/2017 Bozung et al.
2017/0065814 A1 3/2017 Howard et al.
2017/0079598 A1 3/2017 Stolen et al.
2017/0098951 A1 4/2017 Olgun et al.
2017/0098962 A1 4/2017 Desrosiers
2017/0118722 A1 4/2017 Hong et al.
2017/0128729 A1 5/2017 Netoff et al.
2017/0156662 A1 6/2017 Goodall et al.
2017/0157389 A1 6/2017 Tai et al.
2017/0157396 A1 6/2017 Dixon et al.
2017/0161454 A1 6/2017 Grill et al.
2017/0165497 A1 6/2017 Lu
2017/0173326 A1 6/2017 Bloch et al.
2017/0189686 A1 7/2017 Steinke et al.
2017/0239486 A1 8/2017 Suryavanshi
2017/0246450 A1 8/2017 Liu et al.
2017/0246452 A1 8/2017 Liu et al.
2017/0266455 A1 9/2017 Steinke
2017/0274209 A1 9/2017 Edgerton et al.
2017/0291023 A1 10/2017 Kuzma et al.
2017/0296837 A1 10/2017 Jin
2017/0338570 A1 11/2017 Myers
2017/0348523 A1 12/2017 Rubehn et al.
2017/0348532 A1 12/2017 Moffitt et al.
2017/0354819 A1 12/2017 Bloch et al.
2017/0361093 A1 12/2017 Yoo et al.
2017/0361115 A1 12/2017 Aghassian et al.
2018/0008826 A1 1/2018 Dimarco
2018/0028812 A1 2/2018 Vallejo et al.
2018/0056078 A1 3/2018 Kashyap et al.
2018/0083473 A1 3/2018 Menegoli et al.
2018/0085582 A1 3/2018 Calle et al.
2018/0085583 A1 3/2018 Zhang et al.
2018/0093093 A1 4/2018 Courtine et al.
2018/0104479 A1 4/2018 Grill et al.
2018/0110992 A1 4/2018 Parramon et al.
2018/0117334 A1 5/2018 Jung
2018/0125416 A1 5/2018 Schwarz et al.
2018/0125419 A1 5/2018 Yun et al.
2018/0126154 A1 5/2018 Dubuclet
2018/0126155 A1 5/2018 Mclaughlin et al.
2018/0133480 A1 5/2018 Annoni et al.
2018/0133481 A1 5/2018 Von Zitzewitz et al.
2018/0153474 A1 6/2018 Aeschlimann et al.
2018/0178008 A1 6/2018 Bouton et al.
2018/0185632 A1 7/2018 Staunton et al.
2018/0185642 A1 7/2018 Lu

(56) References Cited

U.S. PATENT DOCUMENTS

2018/0185648 A1 7/2018 Nandra et al.
2018/0193655 A1 7/2018 Zhang et al.
2018/0214694 A1 8/2018 Parramon
2018/0221620 A1 8/2018 Metzger
2018/0221651 A1 8/2018 Chang et al.
2018/0228421 A1 8/2018 Saab
2018/0229037 A1 8/2018 Edgerton et al.
2018/0229038 A1 8/2018 Burdick et al.
2018/0236240 A1 8/2018 Harkema et al.
2018/0256906 A1 9/2018 Pivonka et al.
2018/0272125 A1 9/2018 Sandhu
2018/0272132 A1 9/2018 Subbaroyan et al.
2018/0280693 A1 10/2018 Edgerton et al.
2018/0280706 A1 10/2018 Maile et al.
2018/0289971 A1 10/2018 Yeh et al.
2018/0294547 A1 10/2018 Park et al.
2018/0318576 A1 11/2018 Bozung et al.
2018/0326220 A1 11/2018 Kaula et al.
2018/0337547 A1 11/2018 Menegoli et al.
2018/0353755 A1 12/2018 Edgerton et al.
2018/0361146 A1 12/2018 Gerasimenko et al.
2018/0367187 A1 12/2018 Mcfarthing
2018/0369574 A1 12/2018 Dubuclet et al.
2018/0369575 A1 12/2018 Dubuclet et al.
2018/0369576 A1 12/2018 Dubuclet et al.
2019/0001122 A1 1/2019 Ganty et al.
2019/0001139 A1 1/2019 Mishra et al.
2019/0009094 A1 1/2019 Zhang et al.
2019/0017983 A1 1/2019 Smith
2019/0022371 A1 1/2019 Chang et al.
2019/0027257 A1 1/2019 Ghogawala
2019/0033622 A1 1/2019 Olgun et al.
2019/0160294 A1 5/2019 Peterson et al.
2019/0167980 A1 6/2019 Peterson
2019/0167987 A1 6/2019 Lu et al.
2019/0192852 A1 6/2019 De Ridder
2019/0192864 A1 6/2019 Koop et al.
2019/0240468 A1 8/2019 Yun et al.
2019/0247650 A1 8/2019 Tran
2019/0262609 A1 8/2019 Brill et al.
2019/0269917 A1 9/2019 Courtine et al.
2019/0299006 A1 10/2019 Marnfeldt
2019/0321639 A1 10/2019 Rao et al.
2019/0336760 A1* 11/2019 Shah .................. A61N 1/36178
2019/0344070 A1 11/2019 Molnar et al.
2019/0344075 A1 11/2019 Bloch et al.
2019/0358454 A1 11/2019 Lin et al.
2019/0374776 A1 12/2019 Mishra et al.
2019/0374777 A1 12/2019 Burdick et al.
2019/0381313 A1 12/2019 Lu
2019/0381328 A1 12/2019 Wechter et al.
2019/0381382 A1 12/2019 Wu
2020/0009385 A1* 1/2020 Shah .................. A61N 1/36062
2020/0060602 A1 2/2020 Wagner et al.
2020/0061378 A1 2/2020 Ganguly et al.
2020/0086116 A1 3/2020 Formento et al.
2020/0121544 A1 4/2020 George et al.
2020/0139126 A1 5/2020 Napadow et al.
2020/0144846 A1 5/2020 Shin
2020/0147382 A1 5/2020 Caban et al.
2020/0155019 A1 5/2020 Esteller et al.
2020/0155865 A1 5/2020 Lu
2020/0228901 A1 7/2020 Baek
2020/0360697 A1 11/2020 Paoles et al.
2020/0398068 A1 12/2020 Agnihotri et al.
2021/0069052 A1 3/2021 Burke
2021/0093865 A1 4/2021 Vallejo et al.
2021/0121692 A1 4/2021 Edgerton et al.
2021/0153942 A1 5/2021 Scheltienne et al.
2021/0154481 A1 5/2021 Scheltienne et al.
2021/0170177 A1 6/2021 Minassian et al.
2021/0170178 A1 6/2021 Wagner et al.
2021/0187278 A1 6/2021 Lu
2021/0213292 A1 7/2021 Minassian et al.
2021/0236837 A1 8/2021 Lu
2021/0275810 A1 9/2021 Caban
2021/0290955 A1 9/2021 Brouns et al.
2021/0299441 A1 9/2021 Edgerton et al.
2021/0378991 A1 12/2021 Lu
2021/0402186 A1 12/2021 Edgerton et al.
2022/0016420 A1 1/2022 Lo et al.
2022/0111208 A1 4/2022 Phillips et al.
2022/0125374 A1 4/2022 Courtine et al.
2022/0134108 A1 5/2022 Dinsmoor et al.
2022/0143407 A1 5/2022 Zhuang et al.
2022/0161042 A1 5/2022 Lu et al.
2022/0176130 A1 6/2022 Wu et al.
2022/0184386 A1 6/2022 Courtine et al.
2022/0233848 A1 7/2022 Gad et al.
2022/0313993 A1 10/2022 Gerasimenko et al.
2022/0409899 A1 12/2022 Ganty et al.
2023/0045403 A1 2/2023 Robison et al.
2023/0053053 A1 2/2023 Delattre et al.
2023/0186201 A1 6/2023 Cella et al.
2023/0281527 A1 9/2023 Cella et al.
2024/0001116 A1 1/2024 Edgerton et al.
2024/0050746 A1 2/2024 Angeli et al.
2024/0335666 A1 10/2024 Murphy
2024/0374541 A1 11/2024 Lu et al.
2024/0424291 A1 12/2024 Ganty et al.
2024/0424302 A1 12/2024 Dumeny
2025/0025689 A1 1/2025 Lo et al.
2025/0032799 A1 1/2025 Weijand et al.

FOREIGN PATENT DOCUMENTS

CA 2823592 A1 7/2012
CA 2856202 A1 5/2013
CA 2864473 A1 5/2013
CA 3034123 A1 2/2018
CN 101227940 A 7/2008
CN 101822223 A 9/2010
CN 103263727 A 8/2013
CN 104307098 A 1/2015
DE 3830429 A1 3/1990
DE 202007015508 U1 3/2008
EP 0034145 A1 8/1981
EP 0236976 A1 9/1987
EP 0630987 A1 12/1994
EP 1127907 A2 8/2001
EP 1303332 A1 4/2003
EP 1575665 A1 9/2005
EP 1675648 A1 7/2006
EP 1680182 A1 7/2006
EP 2130326 A1 12/2009
EP 2141851 A2 1/2010
EP 2160127 A1 3/2010
EP 2178319 A1 4/2010
EP 2192897 A1 6/2010
EP 2226114 A1 9/2010
EP 2243510 A2 10/2010
EP 2258496 A1 12/2010
EP 2361631 A1 8/2011
EP 2368401 A1 9/2011
EP 2387467 A1 11/2011
EP 2396995 A1 12/2011
EP 2397788 A1 12/2011
EP 2445990 A2 5/2012
EP 2471518 A2 7/2012
EP 2475283 A1 7/2012
EP 2486897 A2 8/2012
EP 2626051 A1 8/2013
EP 2628502 A1 8/2013
EP 2661307 A2 11/2013
EP 2665514 A2 11/2013
EP 2688642 A2 1/2014
EP 2810689 A1 12/2014
EP 2810690 A1 12/2014
EP 2868323 A1 5/2015
EP 2868343 A1 5/2015
EP 2966422 A1 1/2016
EP 2968940 A1 1/2016
EP 3184145 A1 6/2017
EP 3269424 A1 1/2018

(56) References Cited

FOREIGN PATENT DOCUMENTS

| | | | |
|---|---|---|---|
| EP | 3323468 | A1 | 5/2018 |
| EP | 3328481 | A1 | 6/2018 |
| EP | 3381506 | A1 | 10/2018 |
| EP | 3421081 | A1 | 1/2019 |
| EP | 3285855 | B1 | 6/2019 |
| EP | 3495019 | A1 | 6/2019 |
| EP | 3527258 | A1 | 8/2019 |
| EP | 3969100 | B1 | 7/2023 |
| JP | H0326620 | A | 2/1991 |
| JP | 3184145 | B2 | 7/2001 |
| JP | 2002517283 | A | 6/2002 |
| JP | 2002200178 | A | 7/2002 |
| JP | 2004065529 | A | 3/2004 |
| JP | 2007526798 | A | 9/2007 |
| JP | 2008067917 | A | 3/2008 |
| JP | 2008543429 | A | 12/2008 |
| JP | 2009512516 | A | 3/2009 |
| JP | 2011502586 | A | 1/2011 |
| JP | 2011504112 | A | 2/2011 |
| JP | 2012515060 | A | 7/2012 |
| JP | 2013508119 | A | 3/2013 |
| JP | 2014513562 | A | 6/2014 |
| JP | 2014514043 | A | 6/2014 |
| JP | 2016506255 | A | 3/2016 |
| JP | 6132856 | B2 | 5/2017 |
| JP | 2017104685 | A | 6/2017 |
| JP | 2017523868 | A | 8/2017 |
| JP | 2017525509 | A | 9/2017 |
| JP | 2018524113 | A | 8/2018 |
| KR | 101573840 | B1 | 12/2015 |
| RU | 2130326 | C1 | 5/1999 |
| RU | 2141851 | C1 | 11/1999 |
| RU | 2160127 | C1 | 12/2000 |
| RU | 2178319 | C2 | 1/2002 |
| RU | 2192897 | C2 | 11/2002 |
| RU | 2193441 | C2 | 11/2002 |
| RU | 2001102533 | A | 11/2002 |
| RU | 2226114 | C1 | 3/2004 |
| RU | 2258496 | C2 | 8/2005 |
| RU | 2361631 | C2 | 7/2009 |
| RU | 2368401 | C1 | 9/2009 |
| RU | 2387467 | C1 | 4/2010 |
| RU | 2396995 | C2 | 8/2010 |
| RU | 2397788 | C2 | 8/2010 |
| RU | 2445990 | C1 | 3/2012 |
| RU | 2471518 | C2 | 1/2013 |
| RU | 2475283 | C2 | 2/2013 |
| RU | 2661307 | C1 | 7/2018 |
| WO | 8100458 | A1 | 2/1981 |
| WO | 9409808 | A1 | 5/1994 |
| WO | 9747357 | A1 | 12/1997 |
| WO | 9908749 | A1 | 2/1999 |
| WO | 0019912 | A1 | 4/2000 |
| WO | 0209808 | A1 | 2/2002 |
| WO | 0234331 | A2 | 5/2002 |
| WO | 02092165 | A1 | 11/2002 |
| WO | 03005887 | A2 | 1/2003 |
| WO | 03026735 | A2 | 4/2003 |
| WO | 03092795 | A1 | 11/2003 |
| WO | 2003094749 | A1 | 11/2003 |
| WO | 2004087116 | A2 | 10/2004 |
| WO | 2005002663 | A2 | 1/2005 |
| WO | 2005051306 | A2 | 6/2005 |
| WO | 2005065768 | A1 | 7/2005 |
| WO | 2005087307 | A2 | 9/2005 |
| WO | 2006026850 | A1 | 3/2006 |
| WO | 2006135751 | A2 | 12/2006 |
| WO | 2006138069 | A1 | 12/2006 |
| WO | 2007007057 | A1 | 1/2007 |
| WO | 2007007058 | A1 | 1/2007 |
| WO | 2007012114 | A1 | 2/2007 |
| WO | 2007047852 | A2 | 4/2007 |
| WO | 2007057508 | A2 | 5/2007 |
| WO | 2007081764 | A2 | 7/2007 |
| WO | 2007107831 | A2 | 9/2007 |
| WO | 2008075294 | A1 | 6/2008 |
| WO | 2008092785 | A1 | 8/2008 |
| WO | 2008070807 | A3 | 9/2008 |
| WO | 2008109862 | A2 | 9/2008 |
| WO | 2008121891 | A1 | 10/2008 |
| WO | 2009042217 | A1 | 4/2009 |
| WO | 2009111142 | A2 | 9/2009 |
| WO | 2010021977 | A1 | 2/2010 |
| WO | 2010055421 | A1 | 5/2010 |
| WO | 2010083308 | A1 | 7/2010 |
| WO | 2010114998 | A1 | 10/2010 |
| WO | 2010124128 | A1 | 10/2010 |
| WO | 2011005607 | A1 | 1/2011 |
| WO | 2011008459 | A2 | 1/2011 |
| WO | 2011136875 | A1 | 11/2011 |
| WO | 2012050200 | A1 | 4/2012 |
| WO | 2012075195 | A1 | 6/2012 |
| WO | 2012080964 | A1 | 6/2012 |
| WO | 2012094346 | A2 | 7/2012 |
| WO | 2012100260 | A2 | 7/2012 |
| WO | 2012103519 | A2 | 8/2012 |
| WO | 2012129574 | A2 | 9/2012 |
| WO | 2013049658 | A1 | 4/2013 |
| WO | 2013069004 | A1 | 5/2013 |
| WO | 2013071307 | A1 | 5/2013 |
| WO | 2013071309 | A1 | 5/2013 |
| WO | 2013117750 | A1 | 8/2013 |
| WO | 2013152124 | A1 | 10/2013 |
| WO | 2013179230 | A1 | 12/2013 |
| WO | 2013188965 | A1 | 12/2013 |
| WO | 2014005075 | A1 | 1/2014 |
| WO | 2014031142 | A1 | 2/2014 |
| WO | 2014089299 | A2 | 6/2014 |
| WO | 2014144785 | A1 | 9/2014 |
| WO | 2014149895 | A1 | 9/2014 |
| WO | 2014205356 | A2 | 12/2014 |
| WO | 2014209877 | A1 | 12/2014 |
| WO | 2015000800 | A1 | 1/2015 |
| WO | 2015048563 | A2 | 4/2015 |
| WO | 2015063127 | A1 | 5/2015 |
| WO | 2015106286 | A1 | 7/2015 |
| WO | 2015172894 | A1 | 11/2015 |
| WO | 2016005367 | A1 | 1/2016 |
| WO | 2016025913 | A1 | 2/2016 |
| WO | 2016029159 | A2 | 2/2016 |
| WO | 2016033369 | A1 | 3/2016 |
| WO | 2016033372 | A1 | 3/2016 |
| WO | 2016064761 | A1 | 4/2016 |
| WO | 2016110804 | A1 | 7/2016 |
| WO | 2016112398 | A1 | 7/2016 |
| WO | 2016172239 | A1 | 10/2016 |
| WO | 2017005661 | A1 | 1/2017 |
| WO | 2017011410 | A1 | 1/2017 |
| WO | 2017024276 | A1 | 2/2017 |
| WO | 2017035512 | A1 | 3/2017 |
| WO | 2017044904 | A1 | 3/2017 |
| WO | 2017058913 | A1 | 4/2017 |
| WO | 2017062508 | A1 | 4/2017 |
| WO | 2017117450 | A1 | 7/2017 |
| WO | 2017146659 | A1 | 8/2017 |
| WO | 2017188965 | A1 | 11/2017 |
| WO | 2018033591 | A2 | 2/2018 |
| WO | 2018039296 | A2 | 3/2018 |
| WO | 2018039458 | A1 | 3/2018 |
| WO | 2018063879 | A1 | 4/2018 |
| WO | 2018093765 | A1 | 5/2018 |
| WO | 2018106843 | A1 | 6/2018 |
| WO | 2018140531 | A1 | 8/2018 |
| WO | 2018148844 | A1 | 8/2018 |
| WO | 2018217791 | A1 | 11/2018 |
| WO | 2019211314 | A1 | 11/2019 |
| WO | 2020028088 | A1 | 2/2020 |
| WO | 2020041502 | A1 | 2/2020 |
| WO | 2020041633 | A1 | 2/2020 |
| WO | 2020236946 | A1 | 11/2020 |

(56) References Cited

FOREIGN PATENT DOCUMENTS

WO D215131-0001 7/2022
WO 2022221442 A1 10/2022

OTHER PUBLICATIONS

Canadian Office Action in counterpart Canadian Patent Application No. 2906779 mailed May 7, 2020, 5 pages.
Canadian Office Action in counterpart Canadian Patent Application No. 2925754 mailed Nov. 27, 2020, 5 pages.
Canadian Office Action in counterpart Canadian Patent Application No. 2925754 mailed Sep. 28, 2021, 4 pages.
Canadian Office Action in counterpart Canadian Patent Application No. 2958924 mailed Jul. 14, 2022, 4 pages.
Canadian Office Action in counterpart Canadian Patent Application No. 2958924 mailed Oct. 21, 2021, 5 pages.
Canadian Office Action in counterpart Canadian Patent Application No. 3030615 mailed Jun. 19, 2023, 5 pages.
Canadian Office Action in counterpart Canadian Patent Application No. 3030615 mailed Sep. 6, 2022, 5 pages.
Capogrosso, M. et al., "A Brain-Spinal Interface Alleviating Gait Deficits after Spinal Cord Injury in Primates," Nature, (2016), vol. 539, No. 7628, pp. 284-288.
Capogrosso, M. et al., "A Computational Model for Epidural Electrical Stimulation of Spinal Sensorimotor Circuits," Journal of Neuroscience, (2013), vol. 33, No. 49, pp. 19326-19340.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, (2004), vol. 12, No. 1, pp. 32-42.
Chatagny, P. et al., "Distinction between hand dominance and hand preference in primates: a behavioral investigation of manual dexterity in nonhuman primates (macaques) and human subjects," Brain and Behavior, (2013), vol. 3, No. 5, pp. 575-595.
Colgate, E. et al., "An Analysis of Contact Instability in Terms of Passive Physical Equivalents," Proceedings of the 1989 IEEE International Conference on Robotics and Automation, Scottsdale, Arizona, (1989), pp. 404-409.
Communication Pursuant to Article 94(3) EPC in counterpart European Application No. 19209911.7 mailed Mar. 1, 2023, 2 pages.
Communication Pursuant to Article 94(3) EPC in counterpart European Patent Application No. 12760696.0 mailed Nov. 9, 2017, 5 pages.
Communication Pursuant to Article 94(3) EPC in counterpart European Patent Application No. 12847885.6 mailed Apr. 15, 2016, 5 pages.
Communication Pursuant to Article 94(3) EPC in counterpart European Patent Application No. 12847885.6 mailed Feb. 16, 2017, 5 pages.
Communication Pursuant to Article 94(3) EPC in counterpart European Patent Application No. 12848368.2 mailed May 9, 2018, 5 pages.
Communication Pursuant to Article 94(3) EPC in counterpart European Patent Application No. 14765477.6 mailed Nov. 14, 2018, 5 pages.
Communication Pursuant to Article 94(3) EPC in counterpart European Patent Application No. 14765477.6 mailed Sep. 27, 2019, 6 pages.
Communication Pursuant to Article 94(3) EPC in counterpart European Patent Application No. 14849355.4 mailed Jul. 20, 2018, 6 pages.
Communication Pursuant to Article 94(3) EPC in counterpart European Patent Application No. 15834593.4 mailed Jul. 17, 2019, 4 pages.
Communication Pursuant to Article 94(3) EPC in counterpart European Patent Application No. 15834593.4 mailed Jul. 30, 2020, 5 pages.
Communication Pursuant to Article 94(3) EPC in counterpart European Patent Application No. 17826212.7 mailed Dec. 21, 2020, 7 pages.
Communication Pursuant to Article 94(3) EPC in counterpart European Patent Application No. 18807366.2 mailed Mar. 22, 2023, 4 pages.
Communication Pursuant to Article 94(3) EPC in counterpart European Patent Application No. 19209911.7 mailed Jul. 20, 2023, 5 pages.
Communication Pursuant to Article 94(3) EPC in counterpart European Patent Application No. 20160841.1 mailed Mar. 6, 2024, 5 pages.
Communication Pursuant to Article 94(3) EPC in counterpart European Patent Application No. 20726108.2 mailed Mar. 20, 2024, 4 pages.
Communication Pursuant to Article 94(3) EPC in counterpart European Patent Application No. 211660801.7 mailed Mar. 7, 2024, 6 pages.
Communication Pursuant to Article 94(3) EPC in counterpart European Patent Application No. 21166801.7 mailed Mar. 7, 2024, 6 pages.
Communication Pursuant to Article 94(3) EPC in counterpart European Patent Application No. 24153829.7 mailed Apr. 4, 2025, 5 pages.
Communication Pursuant to Rule 114(2) EPC in counterpart European Patent Application No. 12847885.6 mailed Mar. 27, 2015, 28 pages.
Communication Regarding Extended European Search Report in counterpart European Patent Application No. 24153829.7 mailed May 22, 2024, 8 pages.
Cotton, D. P. J. et al., "A Multifunctional Capacitive Sensor for Stretchable Electronic Skins," IEEE Sensors Journal, IEEE Service Center, New York, NY, US, (2009), vol. 9, No. 12, pp. 2008-2009.
Coursera, "What is Machine Learning? Definition, Types, and Examples," Coursera, May 20, 2025. Retrieved from the Internet: <URL:https://www.coursera.org/articles/what-is-machine-learning>, 12 pages.
Courtine, G. et al., "Can experiments in nonhuman primates expedite the translation of treatments for spinal cord injury in humans?" Nature Medicine, (2007), vol. 13, No. 5, pp. 561-566.
Courtine, G. et al., "Modulation of multisegmental monosynaptic responses in a variety of leg muscles during walking and running in humans," Journal of Physiology, (2007), vol. 582, No. 3, pp. 1125-1139.
Courtine, G. et al., "Recovery of supraspinal control of stepping via indirect propriospinal relay connections after spinal cord injury," Nature Medicine, (2008), vol. 14, No. 1, pp. 69-74.
Courtine, G. et al., "Transformation of nonfunctional spinal circuits into functional states after the loss of brain input," Nature Neuroscience, (2009), vol. 12, No. 10, pp. 1333-1342.
Cowley, K. et al., "Propriospinal neurons are sufficient for bulbospinal transmission of the locomotor command signal in the neonatal rat spinal cord," The Journal of Physiology, (2008), vol. 586, No. 6, pp. 1623-1635.
Cyganowski, A et al., "Stretchable electrodes for neuroprosthetic interfaces," Sensors, 2012 IEEE, Taipei, (2012), pp. 1-4.
Dani, V. et al., "Stochastic Linear Optimization Under Bandit Feedback," In Proceedings of the 21st Annual Conference on Learning Theory (COLT), (2008), No. 101, pp. 1-15.
Danner, S. et al., "Human Spinal locomotor control is based on flexibly organized burst generators," Brain: A Journal of Neurology, (2015), vol. 138, No. 3, pp. 577-588.
Danner, S. M. et al., "Body Position Influences Which neural structures are recruited by lumbar transcutaneous spinal cord stimulation," PLoS ONE, (2016), vol. 11, No. 1, pp. 1-13.
Danner, S. M. et al., "Can the Human Lumbar Posterior Columns be Stimulated by Transcutaneous Spinal Cord Stimulation? A modeling study," Europe PMC funders author manuscripts, Artificial Organs, (2011), vol. 35, No. 3, pp. 257-262.
Decision to Refuse a European Patent Application in counterpart European Patent Application No. 15834593.4 mailed Oct. 28, 2021, 24 pages.

(56) References Cited

OTHER PUBLICATIONS

Definition of "Insert," Dictionary [online], Oxford English Dictionary, 2020 [retrieved on Dec. 15, 2022], 2 pages.
Desantana, J. M. et al., "Effectiveness of Transcutaneous Electrical Nerve Stimulation for Treatment of Hyperalgesia and Pain," Current Rheumatology Reports, (2008), vol. 10, pp. 492-499.
Dimitrijevic, M. M. et al. "Evidence for a Spinal Central Pattern Generator in Humans," Annals New York Academy Sciences, (1998), vol. 860, No. 1, pp. 360-376.
Dimitrijevic, M. M. et al., "Clinical Elements for the Neuromuscular Stimulation and Functional Electrical Stimulation protocols in the Practice of Neurorehabilitation," Artificial Organs, vol. 26, No. 4, (2002), pp. 256-259.
Krassioukov, A. et al., "A Systematic Review of the Management of Orthostatic Hypotension Following Spinal Cord Injury," Archives of Physical Medicine and Rehabilitation, (2009), vol. 90, No. 5, pp. 876-885.
Krause, A. et al., "Contextual Gaussian Process Bandit Optimization," In Advances in Neural Information Processing Systems (NIPS), (2011), pp. 1-9.
Krause, A. et al., "Near-optimal Nonmyopic Value of Information in Graphical Models," In UAI, (2005), pp. 1-8.
Krause, A. et al., "Near-Optimal Sensor Placements in Gaussian Processes: Theory, Efficient Algorithms and Empirical Studies," Journal of Machine Learning Research, (2008), vol. 9, pp. 235-284.
Krenn, M. et al., "Selectivity of transcutaneous stimulation of lumbar posterior roots at different spinal levels in humans," Biomedical Technology, (2013), vol. 58 (Suppl. 1), pp. 1-2.
Kwakkel, G. et al., "Effects of Robot-assisted therapy on upper limb recovery after stroke: A Systematic Review," Neurorehabilitation and Neural Repair, (2008), vol. 22, No. 2, pp. 111-121.
Lacour, S. et al., "Flexible and stretchable micro-electrodes for in vitro and in vivo neural interfaces," Medical & Biological Engineering & Computing, (2010), vol. 48, pp. 945-954.
Lacour, S. et al., "Stretchable gold conductors on elastomeric substrates," Applied Physics Letters, (2003), vol. 82, No. 15, pp. 2404-2406.
Ladenbauer, J. et al., "Stimulation of the human lumbar spinal cord with implanted and surface electrodes: a computer simulation study," IEEE Transactions on Neural Systems and Rehabilitation Engineering, (2010), vol. 18, No. 6, pp. 637-645.
Lavrov, I. et al., "Epidural Stimulation Induced Modulation of Spinal Locomotor Networks in Adult Spinal Rats," Journal of Neuroscience, (2008), vol. 28, No. 23, pp. 6022-6029.
Levine, A. et al., "Identification of cellular node for motor control pathways," Nature Neuroscience, (2014), vol. 17, No. 4, pp. 586-593.
Liu, J. et al., "Stimulation of the parapyramidal region of the neonatal rat brain stem produces locomotor-like activity involving spinal 5-HT7 and 5-HT2A receptors," Journal of Neurophysiology, (2005), vol. 94, No. 2, pp. 1392-1404.
Lizotte, D. et al., "Automatic gait optimization with Gaussian process regression," In IJCAI, (2007), vol. 7, pp. 944-949.
Lovely, R. et al., "Effects of Training on the Recovery of Full-Weight-Bearing Stepping in the Adult Spinal Cat," Experimental Neurology, (1986), vol. 92, No. 2, pp. 421-435.
Lozano, A. et al., "Probing and Regulating Dysfunctional Circuits Using Deep Brain Stimulation," Neuron, (2013), vol. 77, No. 3, pp. 406-424.
Lu, D. et al., "Engaging cervical spinal cord networks to re-enable volitional control of hand function in tetraplegic patients," Neurorehabilitation and Neural Repair, (2016), vol. 30, No. 10, pp. 951-962.
"Male and female muscle and skeletal systems," Shutterstock. com, (2021), Retrieved from the Internet: <URL: https://www.shutterstock.com/image-illustration/male-female-muscle-skeletal-systems-xray-1895443960>, 2 pages.
Mcintyre, C. et al., "Modeling the Excitability of Mammalian Nerve Fibers: Influence of Afterpotentials on the Recovery Cycle," Journal of Neurophysiology, (2002), vol. 87, No. 2, pp. 995-1006.
Meacham, K. W. et al., "A lithographically-patterned, elastic multi-electrode array for surface stimulation of the spinal cord," Biomed Microdevices, (2008), vol. 10, pp. 259-269.
Metzger, C. et al., "Flexible-foam-based capacitive sensor arrays for object detection at low cost," Applied Physics Letters, American Institute of Physics, (2008), vol. 92, No. 1, pp. 13506-1-13506-3.
Minassian, K. et al., "Human lumbar cord circuitries can be activated by extrinsic tonic input to generate locomotor-like activity," Human Movement Science, (2007), vol. 26, No. 2, pp. 275-295.
Minassian, K. et al., "Human Lumbar Cord Model of the Locomotor Central Pattern Generator," Second Congress International Society of Intraoperative Neurophysiology (ISIN), (2009), pp. 11-13.
Minassian, K. et al., "Mechanisms of rhythm generation of the human lumbar spinal cord in repose to tonic stimulation without and with step-related sensory feedback," Biomedical Technology, (2013), vol. 58, (Suppl. 1), pp. 1-3.
Minassian, K. et al., "Neuromodulation of lower limb motor control in restorative neurology," Clinical Neurology and Neurosurgery, (2012), vol. 114, No. 5, pp. 489-497.
Minassian, K. et al., "Neurophysiology of the human lumbar locomotor pattern generator," Proceedings 10th Vienna International Workshop on Functional Electrical Stimulation, Center for Medical Physics and Biomedical Engineering, (2010), pp. 259-261.
Minassian, K. et al., "Peripheral and Central Afferent Input to the Lumbar Cord," Biocybernetics and Biomedical Engineering, (2005), vol. 25, No. 3, pp. 11-29.
Minassian, K. et al., "Posterior root-muscle reflex," Second Congress International Society of Intraoperative Neurophysiology (ISIN), Dubrovnik, Croatia, (2009), pp. 77-80.
Minassian, K. et al., "Posterior root-muscle reflexes elicited by transcutaneous stimulation of the human lumbosacral cord," Muscle and Nerve, (2007), vol. 35, No. 3, pp. 327-336.
Minassian, K. et al., "Stepping-like movements in humans with complete spinal cord injury induced by epidural stimulation of the lumbar cord: electromyographic study of compound muscle action potentials," Spinal Cord, (2004), vol. 42, No. 7, pp. 401-416.
Minassian, K. et al., "Transcutaneous spinal cord stimulation," International Society for Restoration Neurology, (2011), pp. 1-6.
Minassian, K. et al., "Transcutaneous stimulation of the human lumbar spinal cord: Facilitating locomotor output in spinal cord injury," Society for Neuroscience, Conference Proceedings, Neuroscience 2010, San Diego, CA, Abstract Viewer/ Itinerary Planner No. 286.19, Abstract & Poster attached, (2010), 2 pages.
Minev, I. R. et al., "Electronic dura mater for long-term multimodal neural interfaces—with supplementary materials," Science, (2015), vol. 347, No. 6218, pp. 1-64.
Minev, I. R. et al., "Evaluation of an Elastomer Based Gold Microelectrode Array for Neural Recording Applications," Proceedings of the 5th International IEEE/EMBS Conference on Neural Engineering, Cancun, Mexico, (2011), pp. 482-485.
Minev, I. R. et al., "High sensitivity recording of afferent nerve activity using ultra-compliant microchannel electrodes: an acute in vivo validation," Journal of Neural Engineering, (2012), vol. 9, No. 2, pp. 1-7.
Minoux, M., "Accelerated greedy algorithms for maximizing submodular set functions," Optimization Techniques, LNCS, (1978), pp. 234-243.
Moraud, E. et al., "Mechanisms Underlying the Neuromodulation of Spinal Circuits for Correcting Gait and Balance Deficits after Spinal Cord Injury," Neuron, (2016), vol. 89, No. 4, pp. 814-828.
Murg, M. et al., "Epidural electric stimulation of posterior structures of the human lumbar spinal cord: 1. Muscle twitches—a functional method to define the site of stimulation," Spinal Cord, (2000), vol. 38, No. 7, pp. 394-402.
Musienko, P. et al., "Combinatory Electrical and Pharmacological Neuroprosthetic Interfaces to Regain Motor Function After Spinal Cord Injury," IEEE Transactions on Biomedical Engineering, (2009), vol. 56, No. 11, pp. 2707-2711.
Musienko, P. et al., "Controlling specific locomotor behaviors through multidimensional monoaminergic modulation of spinal circuitries," The Journal of Neuroscience, (2011), vol. 31, No. 25, pp. 9264-9278.

(56) References Cited

OTHER PUBLICATIONS

Musienko, P. et al., "Multi-system neurorehabilitative strategies to restore motor functions following severe spinal cord injury," Experimental Neurology, (2012), vol. 235, No. 1, pp. 100-109.
Musselman, K. et al., "Spinal Cord Injury Functional Ambulation Profile: A New Measure of Walking Ability," Neurorehabilitation and Neural Repair, (2011), vol. 25, No. 3, pp. 285-293.
Nandra, M. et al., "Microelectrode Implants for Spinal Cord Stimulation in Rats," Doctor of Philosophy Thesis, California Institute of Technology, (2014), pp. 1-104.
Nandra, M. S. et al., "A parylene-based microelectrode array implant for spinal cord stimulation in rats," Conference Proceedings IEEE Engineering in Medicine and Biology Society, (2011), pp. 1007-1010.
Nandra, M. S. et al., "A wireless microelectrode implant for spinal cord stimulation and recording in rats," Presentation Abstract, (2013), pp. 1-104.
Needle, A. R. et al., "Brain Regulation of muscle tone in healthy and functionally unstable ankles," Journal of Sport Rehabilitation, (2013), vol. 22, No. 3, pp. 202-211.
Nessler, J. et al., "A Robotic Device for Studying Rodent Locomotion After Spinal Cord Injury," IEEE Transactions on Neural Systems and Rehabilitation Engineering, (2005), vol. 13, No. 4, pp. 497-506.
Niu, T. et al., "A Proof-of-Concept Study of Transcutaneous Magnetic Spinal Cord Stimulation for Neurogenic Bladder," Scientific Reports, (2018), vol. 8, No. 1, pp. 1-12.
Non-Final Office Action in U.S. Appl. No. 17/595,384, mailed Jun. 5, 2025, 10 pages.
Notice of Allowance in U.S. Appl. No. 14/355,812, mailed Apr. 13, 2016, 7 pages.
Notice of Allowance in U.S. Appl. No. 14/775,618, mailed Jan. 18, 2018, 11 pages.
Dimitrijevic, M. R. et al., "Electrophysiological characteristics of H-reflexes elicited by percutaneous stimulation of the cauda equina," Abstract No. 4927, 34th Annual Meeting of the Society for Neuroscience, San Diego, CA (2004), 1 page.
Dominici, N. et al. "Versatile robotic interface to evaluate, enable and train locomotion and balance after neuromotor disorders," Nature Medicine, (2012), vol. 18, No. 7, pp. 1-8.
Drew, T. et al., "Cortical mechanisms involved in visuomotor coordination during precision walking," Brain Research Reviews, (2008), vol. 57, No. 1, pp. 199-211.
Drummond, G. B. et al., "Thoracic impedance used for measuring chest wall movement in postoperative patients," British Journal of Anaesthesia, (1996), vol. 77, No. 3, pp. 327-332.
Dubinsky, R. M. et al., "Assessment: Efficacy of transcutaneous electric nerve stimulation in the treatment of pain in neurologic disorders (an evidenced-based review)," Report of the Therapeutics and Technology Assessment Subcommittee of the American Academy of Neurology, Neurology, (2010), vol. 74, No. 2, pp. 173-176.
Dunne, L. et al., "Initial development and testing of a novel foam-based pressure sensor for wearable sensing," Journal of NeuroEngineering and Rehabilitation, (2005), vol. 2, No. 4, pp. 1-7.
Duschau-Wicke, A. et al., "Patient-cooperative control increases active participation of individuals with SCI during robot-aided gait training," Journal of NeuroEngineering and Rehabilitation, (2010), vol. 7, No. 43, pp. 1-13.
Edgerton, V. et al., "Robotic Training and Spinal Cord Plasticity," Brain Research Bulletin, (2009), vol. 78, No. 1, pp. 4-12.
Edgerton, V. et al., "Training Locomotor Networks," Brain Research Reviews, (2008), vol. 57, No. 1, pp. 241-254.
Edgerton, V. R. et al., "Epidural stimulation of the spinal cord in spinal cord injury: current status and future challenges," Expert Review of Neurotherapeutics, (2011), vol. 11, No. 10, pp. 1351-1353.
EPO Communication and Supplementary European Search Report in counterpart European Patent Application No. 17745012.9 mailed Aug. 13, 2019, 8 pages.
European Opposition filed in counterpart European Patent Application No. 17826212.7 mailed Dec. 2, 2022, 56 pages.
European Patent Office Action in counterpart European Patent Application No. 25165562.7 mailed Sep. 2, 2025, 9 pages.
European Reply to Communication in counterpart European Patent Application No. 12847885.6 mailed Oct. 24, 2016, 4 pages.
Extended European Search Report in counterpart European Patent Application No. 12847885.6 mailed May 6, 2015, 7 pages.
Extended European Search Report in counterpart European Patent Application No. 14765477.6 mailed Nov. 8, 2016, 10 pages.
Extended European Search Report in counterpart European Patent Application No. 14849355.4 mailed May 10, 2017, 7 pages.
Extended European Search Report in counterpart European Patent Application No. 15834593.4 mailed Apr. 4, 2018, 7 pages.
Extended European Search Report in counterpart European Patent Application No. 15836927.2 mailed Mar. 1, 2018, 9 pages.
Extended European Search Report in counterpart European Patent Application No. 16825005.8 mailed Feb. 19, 2019, 8 pages.
Extended European Search Report in counterpart European Patent Application No. 16833973.7 mailed Dec. 13, 2018, 6 pages.
Extended European Search Report in counterpart European Patent Application No. 18173218.1 mailed Jan. 7, 2019, 6 pages.
Extended European Search Report in counterpart European Patent Application No. 18744685.1 mailed Sep. 7, 2020, 8 pages.
Extended European Search Report in counterpart European Patent Application No. 19201998.2 mailed Apr. 21, 2020, 7 pages.
Extended European Search Report in counterpart European Patent Application No. 19211738.0 mailed May 27, 2020, 8 pages.
Extended European Search Report in counterpart European Patent Application No. 19851613.0 mailed Apr. 19, 2022, 9 pages.
Extended European Search Report in counterpart European Patent Application No. 19852797.0 mailed Apr. 19, 2022, 6 pages.
Extended European Search Report in counterpart European Patent Application No. 20020190.3 mailed Oct. 5, 2020, 7 pages.
Extended European Search Report in counterpart European Patent Application No. 20163794.9 mailed Sep. 18, 2020, 7 pages.
Extended European Search Report in counterpart European Patent Application No. 20164082.8 mailed Jul. 21, 2020, 7 pages.
Extended European Search Report in counterpart European Patent Application No. 20175385.2 mailed Jan. 22, 2021, 8 pages.
Extended European Search Report in counterpart European Patent Application No. 21166801.7 mailed Aug. 17, 2021, 11 pages.
Extended European Search Report in counterpart European Patent Application No. 23189900.6 mailed Jan. 15, 2024, 7 pages.
Extended European Search Report in counterpart European Patent Application No. 19211698.6 mailed May 28, 2020, 6 pages.
Feng, G. H. et al., "Universal concept for fabricating micron to millimeter sized 3-D parylene structures on rigid and flexible substrates," in Proc. IEEE 15th Internal Conference on Micro Electro Mechanical System, Kyoto, Japan, (2003), pp. 594-597.
Fleshman, J. et al., "Electronic Architecture of Type-Identified a-Motoneurons in in the Cat Spinal Cord," Journal of Neurophysiology, (1988), vol. 60, No. 1, pp. 60-85.
Fong, A J. et al., "Recovery of control of posture and locomotion after a spinal cord injury: solutions staring us in the face," Progress in Brain Research, Elsevier Amsterdam, Netherlands, (2009), vol. 175, Chapter 25, pp. 393-418.
Frey, M. et al., "A Novel Mechatronic Body Weight Support System," IEEE Transactions on Neural Systems and Rehabilitation Engineering, (2006), vol. 14, No. 3, pp. 311-321.
Fuentes, R. et al., "Spinal Cord Stimulation Restores Locomotion in Animal Models of Parkinson's Disease," Science, (2009), vol. 323, No. 5921, pp. 1578-1582.
Ganley, K. J. et al., "Epidural Spinal Cord Stimulation Improves Locomotor Performance in Low Asia C, Wheelchair-Dependent, Spinal Cord-Injured Individuals: Insights from Metabolic Response," Topics in Spinal Cord Injury Rehabilitation, (2005), vol. 11, No. 2, pp. 50-63.
Gerasimenko, Y. et al., "Initiation and modulation of locomotor circuitry output with multisite transcutaneous electrical stimulation of the spinal cord in noninjured humans," Journal of Neurophysiology, (2015), vol. 113, No. 3, pp. 834-842.

(56) References Cited

OTHER PUBLICATIONS

Gerasimenko, Y. et al., "Noninvasive Reactivation of Motor Descending Control after Paralysis," Journal of Neurotrauma, (2015), vol. 32, No. 24, pp. 1968-1980.
Gerasimenko, Y. et al., "Novel and Direct Access to the Human Locomotor Spinal Circuitry," Journal of Neuroscience, (2010), vol. 30, No. 10, pp. 3700-3708.
Gerasimenko, Y. et al., "Spinal cord reflexes induced by epidural spinal cord stimulation in normal awake rats," Journal of Neuroscience Methods, (2006), vol. 157, No. 2, pp. 253-263.
Gerasimenko, Y. et al., "Transcutaneous electrical spinal-cord stimulation in humans," Annals of Physical and Rehabilitation Medicine, (2015), vol. 58, No. 4, pp. 225-231.
Gerasimenko, Y. P. et al., "Control of Locomotor Activity in Humans and Animals in the Absence of Supraspinal Influences," Neuroscience and Behavioral Physiology, (2002), vol. 32, No. 4, pp. 417-423.
Gerasimenko, Y. P. et al., "Epidural Spinal Cord Stimulation Plus Quipazine Administration Enable Stepping Complete Spinal Adult Rats," Journal of Neurophysiology, (2007), vol. 98, No. 5, pp. 2525-2536.
Gilja, V. et al., "A high-performance neural prosthesis enabled by control algorithm design—with supplementary materials," Nature Neuroscience, (2012), vol. 15, No. 12, pp. 1-56.
Ginsbourger, D. et al., "Kriging is well-suited to parallelize optimization," Computational Intelligence in Expensive Optimization Problems, Berlin, Heidelberg: Springer Berlin Heidelberg, (2010), Ch. 6, pp. 131-162.
Gittins, J.C., "Bandit Processes and Dynamic Allocation Indices," Journal of the Royal Statistical Society B, (1979), vol. 41, No. 2, pp. 148-164.
Notice of Allowance in U.S. Appl. No. 15/025,201, mailed Aug. 1, 2018, 10 pages.
Notice of Allowance in U.S. Appl. No. 15/208,529, mailed Jun. 17, 2020, 7 pages.
Notice of Allowance in U.S. Appl. No. 15/344,381, mailed Apr. 27, 2021, 12 pages.
Notice of Allowance in U.S. Appl. No. 15/505,053, mailed Feb. 13, 2020, 8 pages.
Notice of Allowance in U.S. Appl. No. 15/505,053, mailed Jun. 4, 2020, 9 pages.
Notice of Allowance in U.S. Appl. No. 15/506,696, mailed May 4, 2020, 8 pages.
Notice of Allowance in U.S. Appl. No. 15/753,963, mailed Dec. 13, 2021, 8 pages.
Notice of Allowance in U.S. Appl. No. 15/975,678, mailed Mar. 4, 2022, 9 pages.
Notice of Allowance in U.S. Appl. No. 16/200,467, mailed May 19, 2021, 8 pages.
Office Action in U.S. Appl. No. 14/355,812, mailed Apr. 8, 2015, 9 pages.
Office Action in U.S. Appl. No. 14/355,812, mailed Sep. 21, 2015, 10 pages.
Office Action in U.S. Appl. No. 14/775,618, mailed Jul. 13, 2016, 17 pages.
Office Action in U.S. Appl. No. 14/775,618, mailed Apr. 25, 2017, 19 pages.
Office Action in U.S. Appl. No. 14/925,791, mailed Jul. 20, 2017, 12 pages.
Office Action in U.S. Appl. No. 15/025,201, mailed Oct. 3, 2017, 10 pages.
Office Action in U.S. Appl. No. 15/096,014, mailed Sep. 14, 2017, 13 pages.
Office Action in U.S. Appl. No. 15/208,529, mailed Oct. 18, 2016, 9 pages.
Office Action in U.S. Appl. No. 15/208,529, mailed Jul. 13, 2017, 9 pages.
Office Action in U.S. Appl. No. 15/208,529, mailed Jul. 27, 2018, 8 pages.
Office Action in U.S. Appl. No. 15/208,529, mailed Apr. 19, 2019, 12 pages.
Office Action in U.S. Appl. No. 15/208,529, mailed Oct. 28, 2019, 7 pages.
Office Action in U.S. Appl. No. 15/344,381, mailed Apr. 17, 2019, 26 pages.
Office Action in U.S. Appl. No. 15/344,381, mailed Dec. 30, 2019, 40 pages.
Office Action in U.S. Appl. No. 15/344,381, mailed Aug. 4, 2020, 41 pages.
Office Action in U.S. Appl. No. 15/505,053, mailed Jun. 4, 2019, 10 pages.
Office Action in U.S. Appl. No. 15/506,696, mailed Jul. 22, 2019, 9 pages.
Office Action in U.S. Appl. No. 15/713,456, mailed Oct. 24, 2018, 13 pages.
Office Action in U.S. Appl. No. 15/740,323, mailed Apr. 7, 2020, 12 pages.
Office Action in U.S. Appl. No. 15/740,323, mailed Nov. 20, 2020, 12 pages.
Office Action in U.S. Appl. No. 15/740,323, mailed Mar. 29, 2021, 11 pages.
Office Action in U.S. Appl. No. 15/740,323, mailed Nov. 26, 2021, 14 pages.
Office Action in U.S. Appl. No. 15/740,323, mailed May 11, 2022, 14 pages.
Office Action in U.S. Appl. No. 15/740,323, mailed Feb. 15, 2023, 16 pages.
Office Action in U.S. Appl. No. 15/750,499, mailed Oct. 31, 2019, 24 pages.
Office Action in U.S. Appl. No. 15/750,499, mailed Aug. 6, 2020, 28 pages.
Office Action in U.S. Appl. No. 15/750,499, mailed Aug. 6, 2021, 30 pages.
Office Action in U.S. Appl. No. 15/753,963, mailed Nov. 13, 2020, 13 pages.
Office Action in U.S. Appl. No. 15/753,963, mailed Jul. 16, 2021, 9 pages.
Office Action in U.S. Appl. No. 15/821,076, mailed Oct. 10, 2018, 13 pages.
Office Action in U.S. Appl. No. 15/975,678, mailed Jan. 8, 2020, 14 pages.
Office Action in U.S. Appl. No. 15/975,678, mailed Jul. 29, 2020, 17 pages.
Office Action in U.S. Appl. No. 15/975,678, mailed Feb. 10, 2021, 12 pages.
Office Action in U.S. Appl. No. 15/975,678, mailed Jul. 20, 2021, 21 pages.
Office Action in U.S. Appl. No. 16/200,467, mailed Apr. 10, 2020, 10 pages.
Office Action in U.S. Appl. No. 16/200,467, mailed Nov. 24, 2020, 7 pages.
Office Action in U.S. Appl. No. 16/479,201, mailed Aug. 25, 2022, 24 pages.
Office Action in U.S. Appl. No. 16/479,201, mailed Jun. 1, 2023, 18 pages.
Office Action in U.S. Appl. No. 16/615,765, mailed May 12, 2021, 13 pages.
Office Action in U.S. Appl. No. 16/615,765, mailed Dec. 6, 2021, 15 pages.
Office Action in U.S. Appl. No. 16/615,765, mailed Jun. 20, 2022, 18 pages.
Office Action in U.S. Appl. No. 18/297,222, mailed Feb. 12, 2026, 7 pages.
Office Action in U.S. Appl. No. 19/335,824, mailed Feb. 19, 2026, 10 pages.
Office Action in U.S. Appl. No. 16/953,322, mailed Feb. 2, 2026, 8 pages.
Abernethy, J. et al., "Competing in the dark: An efficient algorithm for bandit linear optimization," Conference on Learning Theory, (2009), No. 110, pp. 1-13.

(56) References Cited

OTHER PUBLICATIONS

"Aching knee or sore back? New app helps doctors treat pain," medicalxpress.com, (2017), Retrieved from the Internet: <URL: https://medicalxpress.com/news/2017-05-aching-knee-sore-app-doctors.html>, 1 page.
Ada, L. et al., "Mechanically assisted walking with body weight support results in more independent walking than assisted overground walking in non-ambulatory patients early after stroke: a systematic review," Journal of Physiotherapy, (2010), vol. 56, No. 3, pp. 153-161.
Alto, L. et al., "Chemotropic guidance facilitates axonal regeneration and synapse formation after spinal cord injury," Nature Neuroscience, (2009), vol. 12, No. 9, pp. 1106-1113.
Anderson, K., "Targeting recovery: priorities of the spinal cord-injured population," Journal of Neurotrauma, (2004), vol. 21, No. 10, pp. 1371-1383.
Andersson, K. E. et al., "CNS Involvement in Overactive Bladder—Pathophysiology and Opportunities for Pharmacological Intervention," Drugs, (2003), vol. 63, No. 23, pp. 2595-2611.
Angeli, C. et al., "Altering spinal cord excitability enables voluntary movements after chronic complete paralysis in humans," Brain: A Journal of Neurology, (2014), vol. 137, No. 5, pp. 1394-1409.
Anonymous, "Re: Round corners (fillet) in Illustrator CS6," in: Stack Exchange [online], Graphic Design, Jan. 22, 2018; 17:52 [retrieved on Feb. 6, 2024]. Retrieved from the Internet: <URL:https://graphicdesign.stackexchange.com/questions/104349/round-corners-fillet-in-illustrator-cs6>, 10 pages.
Anonymous, "Lumbar Decompression Surgery: When it's used," Datasheet [online], National Health Service, 2022. Retrieved from the Internet: <URL:https://www.nhs.uk/conditions/lumbar-decompression-surgery/why-its-done/#:-:text=Cauda%equina%20syndrome%20a.is%20severe%20or%20getting%20worse, 2 pages.
Anonymous, "Vital Signs," Datasheet [online], Cleveland Clinic [retrieved on Nov. 22, 2021]. Retrieved from the Internet: <URL:https://my.clevelandclinic.org/health/articles/10881-vital-signs, 19 pages.
Ateh, D. D. et al., "Polypyrrole-based conducting polymers and interactions with biological tissues," Journal of the Royal Society Interface, (2006), vol. 3, No. 11, pp. 741-752.
Auer, P. et al., "Finite-time analysis of the multiarmed bandit problem," Machine Learning, (2002), vol. 47, No. 2, pp. 235-256.
Auer, P., "Using confidence bounds for exploitation-exploration trade-offs," Journal of Machine Learning Research, (2002), vol. 3, pp. 397-422.
Australian Examination Report No. 1 in counterpart Australian Patent Application No. 2012334926 mailed Jul. 11, 2016, 3 pages.
Australian Examination Report No. 1 in counterpart Australian Patent Application No. 2014228794 mailed May 11, 2018, 4 pages.
Australian Examination Report No. 1 in counterpart Australian Patent Application No. 2014324660 mailed Jan. 11, 2019, 5 pages.
Australian Examination Report No. 1 in counterpart Australian Patent Application No. 2015305237 mailed Jun. 14, 2019, 4 pages.
Australian Examination Report No. 1 in counterpart Australian Patent Application No. 2015308779 mailed Jul. 18, 2019, 3 pages.
Australian Examination Report No. 1 in counterpart Australian Patent Application No. 2017202237 mailed Apr. 6, 2018, 3 pages.
Australian Examination Report No. 1 in counterpart Australian Patent Application No. 2017203132 mailed Oct. 13, 2017, 4 pages.
Australian Examination Report No. 1 in counterpart Australian Patent Application No. 2017221868 mailed Jan. 23, 2018, 3 pages.
Australian Examination Report No. 1 in counterpart Australian Patent Application No. 2019206059 mailed Jan. 6, 2020, 4 pages.
Australian Examination Report No. 1 in counterpart Australian Patent Application No. 2020200152 mailed Dec. 21, 2020, 4 pages.
Australian Examination Report No. 2 in counterpart Australian Patent Application No. 2014324660 mailed Nov. 7, 2019, 4 pages.
Australian Examination Report No. 2 in counterpart Australian Patent Application No. 2015305237 mailed Apr. 17, 2020, 4 pages.
Australian Examination Report No. 2 in counterpart Australian Patent Application No. 2015308779 mailed May 20, 2020, 3 pages.
Australian Examination Report No. 3 in counterpart Australian Patent Application No. 2014324660 mailed Jan. 6, 2020, 4 pages.
Axisa, F. et al., "Elastic and Conformable Electronic Circuits and Assemblies using MID in polymer," 6th International Conference on Polymers and Adhesives in Microelectronics and Photonics, IEEE Polytronic 2007 Conference, (2007), pp. 280-286.
Azimi, J. et al., "Batch Active Learning via Coordinated Matching," In Proceedings of the 29th International Conference on Machine Learning, (2012), pp. 1-8.
Azimi, J. et al., "Batch Bayesian Optimization via Simulation Matching," In Advances in Neural Information Processing Systems (NIPS), (2010), pp. 1-9.
Azimi, J. et al., "Hybrid Batch Bayesian Optimization," In Proceedings of the 29th International Conference on Machine Learning, (2012), pp. 1-12.
"Back pain and body posture infographic", Alamy.com, (2017), Retrieved from the Internet: <URL:https://www.alamy.com/stock-photo-back-pain-and-body-posture-infographic-with-anatomical-illustrations-141494074.html?imageid=27CC5905-F123-4DSC-847A4C76D50631C1&p=313080&pn=1&searchId=526c9d4db7f91a3e259d7b785fa370c3&searchtype=0>, 2 pages.
Barbeau, H. et al., "Recovery of locomotion after chronic spinalization in the adult cat," Brain Research, (1987), vol. 412, No. 1, pp. 84-95.
Bareyre, F. et al., "The injured spinal cord spontaneously forms a new intraspinal circuit in adult rats," Nature Neuroscience, (2004), vol. 7, No. 3, pp. 269-277.
Basso, D. et al., "MASCIS Evaluation of Open Field Locomotor Scores: Effects of Experience and Teamwork on Reliability," Journal of Neurotrauma, (1996), vol. 13, No. 7, pp. 343-359.
Bizzi, E. et al., "Modular organization of motor behavior," Zeitschrift für Naturforschung, (1998), vol. 53, No. 7-8, pp. 510-517.
Brochu, et al., "A Tutorial on Bayesian Optimization of Expensive Cost Functions, with Application to Active User Modeling and Hierarchical Reinforcement Learning," In TR-2009-23, UBC, (2009), pp. 1-49.
Brosamle, C. et al., "Cells of Origin, Course, and Termination Patterns of the Ventral, Uncrossed Component of the Mature Rat Corticospinal Tract," The Journal of Comparative Neurology, (1997), vol. 386, No. 2, pp. 293-303.
Bruckenstein, S. et al., "An experimental study of nonuniform current distribution at rotating disk electrodes," Journal of the Electrochemical Society, (1970), vol. 117, No. 8, pp. 1044-1048.
Bubeck, S. et al., "Online Optimization in X-Armed Bandits," Advances in Neural Information Processing Systems (NIPS), (2008), pp. 1-8.
Bubeck, S. et al., "Pure Exploration in Finitely-Armed and Continuous-Armed Bandits problems," In ALT, (2009), pp. 1-35.
Burke, R., "Group Ia Synaptic Input to Fast and Slow Twitch Motor Units of Cat Triceps Surae," The Journal of Physiology, (1968), vol. 196, No. 3, pp. 605-630.
Cai, L. et al., "Implications of Assist-As-Needed Robotic Step Training after a Complete Spinal Cord Injury on Intrinsic Strategies of Motor Learning," The Journal of Neuroscience, (2006), vol. 26, No. 41, pp. 10564-10568.
Canadian Office Action in counterpart Canadian Patent Application No. 2823592 mailed Oct. 5, 2017, 4 pages.
Canadian Office Action in counterpart Canadian Patent Application No. 2824782 mailed Nov. 29, 2017, 4 pages.
Canadian Office Action in counterpart Canadian Patent Application No. 2825550 mailed Jan. 24, 2018, 4 pages.
Canadian Office Action in counterpart Canadian Patent Application No. 2856202 mailed Jun. 19, 2018, 4 pages.
Canadian Office Action in counterpart Canadian Patent Application No. 2864473 mailed Aug. 14, 2020, 4 pages.
Canadian Office Action in counterpart Canadian Patent Application No. 2864473 mailed Aug. 31, 2018, 5 pages.
Canadian Office Action in counterpart Canadian Patent Application No. 2864473 mailed Jul. 30, 2019, 5 pages.
Giuliano, F. et al., "Neural Control of Erection," Physiology & Behavior, (2004), vol. 83, No. 2, pp. 189-201.

(56) References Cited

OTHER PUBLICATIONS

Graf, N. et al., "Electrochemically Stimulated Release from Liposomes Embedded in a Polyelectrolyte Multilayer," Advanced Functional Materials, (2011), vol. 21, No. 9, pp. 1666-1672.
Graz, I. et al., "Flexible ferroelectret field-effect transistor for large-area sensor skins and microphones," Applied Physics Letters, American Institute of Physics, (2006), vol. 89, No. 7, pp. 73501-1-73501-3.
Graz, I. et al., "Silicone substrate with in situ strain relief for stretchable thin-film transistors," Applied Physics Letters, AIP, American Institute of Physics, (2011), vol. 98, No. 12, pp. 124101-1-124101-3.
Guyatt, G. et al., "The 6-minute walk: a new measure of exercise capacity in patients with chronic heart failure," Canadian Medical Association Journal, (1985), vol. 132, No. 8, pp. 919-923.
Hagglund, M. et al., "Activation of groups of excitatory neurons in the mammalian spinal cord or hindbrain evokes locomotion," Nature Neuroscience, (2010), vol. 13, No. 2, pp. 246-252.
Harkema, S. et al., "Effect of Epidural stimulation of the lumbosacral spinal cord on voluntary movement, standing, and assisted stepping after motor complete paraplegia: a case study," Lancet, (2011), vol. 377, No. 9781, pp. 1938-1947.
Harkema, S. et al., "Human Lumbosacral Spinal Cord Interprets Loading During Stepping," Journal of Neurophysiology, (1997), vol. 77, No. 2, pp. 797-811.
Harkema, S. et al., "Normalization of Blood Pressure with Spinal Cord Epidural Stimulation After Severe Spinal Cord Injury," Frontiers in Human Neuroscience, (2018), vol. 12, pp. 1-11.
Harrison, P. et al., "Individual Excitatory Post-Synaptic Potentials Due to Muscle Spindle la Afferents in Cat Triceps Surae Motoneurones," The Journal Physiology, (1981), vol. 312, No. 1, pp. 455-470.
Hashtrudi-Zaad, K. et al., "On the Use of Local Force Feedback for Transparent Teleoperation," Proceedings of the 1999 IEEE International Conference on Robotics and Automation, (1999), vol. 3, pp. 1863-1869.
Health Journalism Glossary: Bidirectional, Definition [online], Association of Health Care Journalists, 2024. Retrieved from the Internet: <URL:https://healthjournalism.org/glossary-terms/bidirectional/>, 3 pages.
Hennig, P. et al., "Entropy search for information-efficient global optimization," Journal of Machine Learning Research (JMLR), (2012), vol. 13, No. 1, pp. 1809-1837.
Herman, R. et al., "Spinal cord stimulation facilitates functional walking in a chronic, incomplete spinal cord injured," Spinal Cord, (2002), vol. 40, No. 2, pp. 65-68.
Hidler, J. et al., "ZeroG: Overground gait and balance training system," Journal of Rehabilitation Research & Development, (2011), vol. 48, No. 4, pp. 287-298.
Hines, M. et al., "The NEURON Simulation Environment," Neural Computation, (1997), vol. 9, No. 6, pp. 1179-1209.
Hofstoetter, U. S. et al., "Modification of spasticity by transcutaneous spinal cord stimulation in individuals with incomplete spinal cord injury," The Journal of Spinal Cord Medicine, (2014), vol. 37, No. 2, pp. 202-211.
Hofstoetter, U.S. et al., "Effects of transcutaneous spinal cord stimulation on voluntary locomotor activity in an incomplete spinal cord injured individual," Biomedical Technology, (2013), vol. 58 (Suppl. 1), pp. 1-3.
Hofstoetter, U.S. et al., "Modification of Reflex Responses to Lumbar Posterior Root Stimulation by Motor Tasks in Healthy Subjects," Artificial Organs, (2008), vol. 32, No. 8, pp. 644-648.
Hofstotter, U.S. et al., "Model of spinal cord reflex circuits in humans: Stimulation frequency-dependence of segmental activities and their interactions," Second Congress International Society of Intraoperative Neurophysiology (ISIN), Dubrovnik, Croatia, (2009), pp. 1-149.
Hohenschurz-Schmidt, D. J. et al., "Linking Pain Sensation to the Autonomic Nervous System: The Role of the Anterior Cingulate and Periaqueductal Gray Resting-State Networks," Front Neuroscience, (2020), vol. 14, No. 147, pp. 1-15.
Hovey, C. et al., "The New Guide to Magnet Stimulation," The Magstim Company Ltd., (2006), pp. 1-45.
Hung, C. C. et al., "Transparent microprobe array fabricated by MEMS hot embossing technology for photodynamic therapy application," IEICE Electronics Express, (2010), vol. 7, No. 9, pp. 569-576.
Ichiyama et al., "Step training reinforces specific spinal locomotor circuitry in adult spinal rats," Journal of Neuroscience, (2008), vol. 28, No. 29, pp. 7370-7375.
Ichiyama, R. M. et al., "Hindlimb stepping movements in complete spinal rats induced by epidural spinal cord stimulation," Neuroscience Letters, (2005), vol. 383, No. 3, pp. 339-344.
International Preliminary Report on Patentability issued in counterpart PCT Application No. PCT/US2012/020112 mailed Jul. 10, 2013, 5 pages.
International Preliminary Report on Patentability issued in counterpart PCT Application No. PCT/US2012/064878 mailed May 22, 2014, 8 pages.
International Preliminary Report on Patentability issued in counterpart PCT Application No. PCT/US2014/029340 mailed Sep. 24, 2015, 8 pages.
International Preliminary Report on Patentability issued in counterpart PCT Application No. PCT/US2014/057886, mailed Apr. 7, 2016, 6 pages.
International Preliminary Report on Patentability issued in counterpart PCT Application No. PCT/US2015/046378 mailed Feb. 21, 2017, 5 pages.
International Preliminary Report on Patentability issued in counterpart PCT Application No. PCT/US2015/047268 mailed Feb. 28, 2017, 12 pages.
International Preliminary Report on Patentability issued in counterpart PCT Application No. PCT/US2015/047272 mailed Feb. 28, 2017, 8 pages.
International Preliminary Report on Patentability issued in counterpart PCT Application No. PCT/US2016/041802 mailed Jan. 25, 2018, 12 pages.
International Preliminary Report on Patentability issued in counterpart PCT Application No. PCT/US2016/045898 mailed Feb. 15, 2018, 8 pages.
International Preliminary Report on Patentability issued in counterpart PCT Application No. PCT/US2016/049129 mailed Mar. 8, 2018, 9 pages.
International Preliminary Report on Patentability issued in counterpart PCT Application No. PCT/US2018/015098 mailed Jul. 30, 2019, 7 pages.
International Preliminary Report on Patentability issued in counterpart PCT Application No. PCT/US2018/033942 mailed Nov. 26, 2019, 6 pages.
International Preliminary Report on Patentability issued in counterpart PCT Application No. PCT/US2019/047551 mailed Feb. 23, 2021, 7 pages.
International Preliminary Report on Patentability issued in counterpart PCT Application No. PCT/US2019/047777 mailed Feb. 23, 2021, 12 pages.
International Preliminary Report on Patentability issued in counterpart PCT Application No. PCT/US2020/033830 mailed Dec. 2, 2021, 7 pages.
International Search Report and Written Opinion issued in counterpart PCT Application No. EP2020/063564, mailed Sep. 11, 2020, 12 pages.
International Search Report and Written Opinion issued in counterpart PCT Application No. PCT/EP2017/083478, mailed May 3, 2018, 10 pages.
International Search Report and Written Opinion issued in counterpart PCT Application No. PCT/EP2018/082939, mailed Feb. 14, 2019, 11 pages.
International Search Report and Written Opinion issued in counterpart PCT Application No. PCT/EP2018/082942, mailed Feb. 14, 2019, 11 pages.
International Search Report and Written Opinion issued in counterpart PCT Application No. PCT/EP2020/053381, mailed May 12, 2020, 8 pages.

(56) References Cited

OTHER PUBLICATIONS

International Search Report and Written Opinion issued in counterpart PCT Application No. PCT/EP2020/063563, mailed Jul. 30, 2020, 14 pages.
International Search Report and Written Opinion issued in counterpart PCT Application No. PCT/US2012/064878 mailed Mar. 19, 2013, 11 pages.
International Search Report and Written Opinion issued in counterpart PCT Application No. PCT/US2014/029340 mailed Aug. 6, 2014, 11 pages.
International Search Report and Written Opinion issued in counterpart PCT Application No. PCT/US2014/057886 mailed Dec. 24, 2014, 6 pages.
International Search Report and Written Opinion issued in counterpart PCT Application No. PCT/US2015/011263 mailed May 19, 2015, 12 pages.
International Search Report and Written Opinion issued in counterpart PCT Application No. PCT/US2015/046378 mailed Dec. 1, 2015, 5 pages.
International Search Report and Written Opinion issued in counterpart PCT Application No. PCT/US2015/047268 mailed Dec. 8, 2015, 17 pages.
International Search Report and Written Opinion issued in counterpart PCT Application No. PCT/US2015/047272 mailed Dec. 3, 2015, 11 pages.
International Search Report and Written Opinion issued in counterpart PCT Application No. PCT/US2016/041802 mailed Sep. 12, 2016, 17 pages.
International Search Report and Written Opinion issued in counterpart PCT Application No. PCT/US2016/045898 mailed Dec. 5, 2016, 13 pages.
International Search Report and Written Opinion issued in counterpart PCT Application No. PCT/US2016/049129 mailed Dec. 5, 2016, 13 pages.
International Search Report and Written Opinion issued in counterpart PCT Application No. PCT/US2017/015435, mailed May 8, 2017, 9 pages.
International Search Report and Written Opinion issued in counterpart PCT Application No. PCT/US2018/015098 mailed Mar. 12, 2018, 9 pages.
International Search Report and Written Opinion issued in counterpart PCT Application No. PCT/US2018/033942 mailed Aug. 31, 2018, 8 pages.
International Search Report and Written Opinion issued in counterpart PCT Application No. PCT/US2019/047551 mailed Nov. 21, 2019, 9 pages.
International Search Report and Written Opinion issued in counterpart PCT Application No. PCT/US2019/047777 mailed Nov. 14, 2019, 15 pages.
International Search Report and Written Opinion issued in counterpart PCT Application No. PCT/US2020/033830 mailed Oct. 14, 2020, 10 pages.
International Search Report and Written Opinion issued in counterpart PCT Application No. PCT/US2022/024673 mailed Jun. 28, 2022, 8 pages.
International Search Report issued in counterpart PCT Application No. PCT/US2012/020112 mailed Jul. 30, 2012, 4 pages.
International Search Report issued in counterpart PCT Application No. PCT/US2012/022257 mailed Sep. 3, 2012, 4 pages.
International Search Report issued in counterpart PCT Application No. PCT/US2012/030624 mailed Oct. 31, 2012, 3 pages.
International Search Report issued in counterpart PCT Application No. PCT/US2012/064874 mailed Mar. 19, 2013, 4 pages.
Ivanenko, Y. P. et al., "Temporal Components of the Motor Patterns Expressed by the Human Spinal Cord Reflect Foot Kinematics," Journal of Neurophysiology, (2003), vol. 90, No. 5, pp. 3555-3565.
Iyer, P. C. et al., "Characterization of stimulus response curves obtained with transcranial magnetic stimulation from bilateral tibialis anterior muscles post stroke," Neuroscience Letters, (2019), vol. 713, pp. 1-15.
Jaman, R., "A retrospective cross-sectional survey of lumbo-sacral recorded at the D.U.T. Chiropractic Day Clinic (1995-2005)," (2014). Durban University of Technology, Master's Degree in Technology dissertation. Retrieved from the Internet: <URL: https://doi.org/10.51415/10321/221>, 94 pages.
Japanese Patent Office Action in counterpart Japanese Patent Application No. 2017198155 mailed Aug. 20, 2019, 4 pages.
Japanese Patent Office Action in counterpart Japanese Patent Application No. 2017198155 mailed Sep. 11, 2018, 8 pages.
Japanese Patent Office Action in counterpart Japanese Patent Application No. 2018501208 mailed Jul. 13, 2020, 10 pages.
Japanese Patent Office Action in counterpart Japanese Patent Application No. 2018501208 mailed Mar. 22, 2021, 6 pages.
Japanese Patent Office Action in counterpart Japanese Patent Application No. 2019539960 mailed Feb. 17, 2023, 10 pages.
Japanese Patent Office Action in counterpart Japanese Patent Application No. 2019539960 mailed Nov. 29, 2021, 14 pages.
Japanese Patent Office Action in counterpart Japanese Patent Application No. 2019539960 mailed Sep. 26, 2022, 8 pages.
Japanese Patent Office Action in counterpart Japanese Patent Application No. 2021188658 mailed Nov. 21, 2022, 16 pages.
Japanese Patent Office Action in counterpart Japanese Patent Application No. 2021188658 mailed Sep. 4, 2023, 7 pages.
Japanese Patent Office Action in counterpart Japanese Patent Application No. 2021509772 mailed Jul. 18, 2023, 17 pages.
Japanese Patent Office Action in counterpart Japanese Patent Application No. 2021510130 mailed Aug. 21, 2023, 20 pages.
Jarosiewicz, B. et al., "Supplementary Materials for Virtual typing by people with tetraplegia using a self-calibrating intracortical brain-computer interface," Science Translational Medicine, (2015), vol. 7, No. 313, pp. 1-26.
Jarosiewicz, B. et al., "Virtual typing by people with tetraplegia using a self-calibrating intracortical brain-computer interface," Science Translational Medicine, (2015), vol. 7, No. 313, pp. 1-11.
Jenny, A. B. et al., "Principles of Motor Organization of the Monkey Cervical Spinal Cord," The Journal of Neuroscience, (1983), vol. 3, No. 3, pp. 567-575.
Jilge, B. et al., "Initiating extension of the lower limbs in subjects with complete spinal cord injury by epidural lumbar cord stimulation," Experimental Brain Research, (2004), vol. 154, pp. 308-326.
Johnson, W. et al., "Application of a Rat Hindlimb Model: A Prediction of Force Spaces Reachable Through Stimulation of Nerve Fascicles," IEEE Transactions on Bio-Medical Engineering, (2011), vol. 58, No. 12, pp. 3328-3338.
Jones, D. R. et al., "Efficient Global Optimization of Expensive Black-Box Functions," Journal of Global Optimization, (1998), vol. 13, pp. 455-492.
Jones, K. et al., "Computer Simulation of the Responses of Human Motoneurons to Composite 1A EPSPS: Effects of Background Firing Rate," The Journal of Physiology, (1997), vol. 77, No. 1, pp. 405-420.
Jonic, S. et al., "Three machine learning techniques for automatic determination of rules to control locomotion," IEEE Transactions on Biomedical Engineering, (1999), vol. 46, No. 3, pp. 300-310.
Kakulas, A. B., "A Review of the Neuropathology of Human Spinal Cord Injury with Emphasis on Special Features," Proceedings of the Donald Munro Memorial Lecture at the American Paraplegia Society 44th Annual Conference, Las Vegas, NV, Spinal Cord, (1999), vol. 22, No. 2, pp. 119-124.
Kapetanakis, S. et al., "Cauda Equina Syndrome Due to Lumbar Disc Herniation: a Review of Literature," Folia Medica, (2017), vol. 59, No. 4, pp. 377-386.
Kim, W. S. et al., "Ultra-sensitive Flexible Pressure Sensor with Stamped Polyurethane Rubber," 2011 11th IEEE Conference on Nanotechnology, (2011), pp. 1607-1610.
Kim, Y. et al., "Electrical behavior of defibrillation and pacing electrodes," Proceedings of the IEEE, (2002), vol. 84, No. 3, pp. 446-456.
Kirazh, O. et al., "Anatomy of the spinal dorsal root entry zone: its clinical significance," Acta Neurochirurgica, (2014), vol. 156, pp. 2351-2358.
Kirkwood, P., "Neuronal Control of Locomotion: From Mollusc to Man," G.N. Orlovsky, T.G. Deliagina and S. Grillner. Oxford

(56) References Cited

OTHER PUBLICATIONS

University Press, Oxford, 1999. ISBN 0198524056 (Hbk), 322 pp., Clinical Neurophysiology, vol. 111, (2000): 1524-1525.
Kitano, K. et al., "Spinal reflex in human lower leg muscles evolved by transcutaneous spinal cord stimulation," Journal of Neuroscience Methods, (2009), vol. 180, No. 1, pp. 111-115.
Kleinberg, R. et al., "Multi-armed bandits in metric spaces," In STOC, Computer and Automation Research Institute of the Hungarian Academy of Sciences, Budapest, Hungary, (2008), pp. 1-26.
Kocsis, L. et al., "Bandit Based Monte-Carlo Planning," European Conference on Machine Learning, Springer, Berlin, Heidelberg, (2006), pp. 282-293.
Kondo, T. et al., "Laser monitoring of chest wall displacement," European Respiratory Journal, (1997), vol. 10, No. 8, pp. 1865-1869.
Krassioukov, A. et al., "A Systematic Review of the Management of Autonomic Dysreflexia Following Spinal Cord Injury," Archives of Physical Medicine and Rehabilitation, (2009), vol. 90, No. 4, pp. 682-695.
Office Action in U.S. Appl. No. 17/206,007, mailed Dec. 15, 2025, 18 pages.
Office Action in U.S. Appl. No. 17/511,496, mailed Oct. 3, 2025, 17 pages.
Steward, O. et al., "False Resurrections: Distinguishing Regenerated from Spared Axons in the Injured Central Nervous System," The Journal of Comparative Neurology, (2003), vol. 459, No. 1, pp. 1-8.
Stienen, A. et al., "Analysis of reflex modulation with a biologically realistic neural network," Journal of Computer Neuroscience, (2007), vol. 23, pp. 333-348.
Sun, F. et al., "Sustained axon regeneration induced by co-deletion of PTEN and SOCS3—with supplementary material," Nature, (2011), vol. 480, No. 7377, pp. 372-375.
Suzuki, T. et al., "A 3D flexible parylene probe array for multi-channel neural recording," IEEE Neural Engineering, (2003), pp. 154-156.
Szava, Z. et al., "Transcutaneous electrical spinal cord stimulation: Biophysics of a new rehabilitation method after spinal cord injury," VDM Publishing, Saarbrucken, Germany, (2011), pp. 1-95.
Takeoka, A. et al., "Muscle Spindle Feedback Directs Locomotor Recovery and Circuit Reorganization after Spinal Cord Injury," Cell, (2014), vol. 159, No. 7, pp. 1626-1639.
Takeuchi, S. et al., "3D flexible multichannel neural probe array," Journal of Micromechanics and Microengineering, (2004), vol. 14, No. 1, pp. 104-107.
Tanabe, S. et al., "Effects of transcutaneous electrical stimulation combined with locomotion-like movement in the treatment of post-stroke gait disorder: a single-case study," (2008), vol. 30, No. 5, pp. 411-416.
Temel, Y. et al., "Case Report—Deep brain stimulation of the thalamus can influence penile erection," International Journal of Impotence Research, (2004), vol. 16, No. 1, pp. 91-94.
Tenne, Y. et al., "Computational Intelligence in Expensive Optimization Problems," Adaptation, Learning, and Optimization, Springer, Berlin Heidelberg, (2010), vol. 2, pp. 131-162.
The State Intellectual Property Office of People's Republic of China Office Action in counterpart Chinese Patent Application No. 201610987062.5 mailed Sep. 30, 2018, 20 pages.
The State Intellectual Property Office of People's Republic of China Office Action in counterpart Chinese Patent Application No. 201680058067.8 mailed Jan. 6, 2021, 1 page.
The State Intellectual Property Office of People's Republic of China Office Action in counterpart Chinese Patent Application No. 201780080305.X mailed Aug. 31, 2023, 9 pages.
Timoszyk, W. et al., "Hindlimb loading determines stepping quantity and quality following spinal cord transection," Brain Research, (2005), vol. 1050, No. 1-2, pp. 180-189.
Troni, W. et al., "A methodological reappraisal of non invasive high voltage electrical stimulation of lumbosacral nerve roots," Clinical Neurophysiology, (2011), vol. 122, No. 10, pp. 2071-2080.
Tungjitkusolmun, S. et al., "Finite element analyses of uniform current density electrodes for radio-frequency cardiac ablation," IEEE Transactions on Biomedical Engineering, (2000), vol. 47, No. 1, pp. 32-40.
U.S. Appl. No. 15/821,076, filed Nov. 22, 2017, 52 pages.
U.S. Appl. No. 16/153,472, filed Oct. 5, 2018, 51 pages.
U.S. Appl. No. 16/189,655, filed Nov. 13, 2018, 37 pages.
U.S. Appl. No. 61/802,034, filed Mar. 15, 2013, 29 pages.
U.S. Appl. No. 62/171,427, filed Jun. 5, 2015, 55 pages.
U.S. Appl. No. 62/171,436, filed Jun. 5, 2015, 44 pages.
U.S. Appl. No. 62/201,973, filed Aug. 6, 2015, 54 pages.
Valchinov, E. S. et al., "An active electrode for biopotential recording from small localized bio-sources," BioMedical Engineering OnLine, (2004), vol. 3, No. 25, pp. 1-14.
Vallery, H. et al., "Compliant Actuation of Rehabilitation Robots," IEEE Robotics & Automation Magazine, (2008), vol. 15, No. 3, pp. 60-69.
Van Den Brand, R. et al., "Restoring Voluntary Control of Locomotion after Paralyzing Spinal Cord Injury," Science Magazine, (2012), vol. 336, No. 6085, pp. 1182-1185.
Wan, D. et al., "Life-threatening outcomes associated with autonomic dysreflexia: A clinical review," Journal of Spinal Cord Medicine, (2014), vol. 37, No. 1, pp. 2-10.
Wang, J. M. et al., "Gaussian process dynamical models for human motion," IEEE Transactions on Pattern Analysis and Machine Intelligence, (2007), vol. 30, No. 2, pp. 283-298.
Wang, T. et al., "Incidence of C5 nerve root palsy after cervical surgery—A meta-analysis for decade," Medicine, (2017), vol. 96, No. 45, pp. 1-14.
Ward, A. R. et al., "Sensory, motor, and pain thresholds for stimulation with medium frequency alternating current," Archives of Physical Medicine and Rehabilitation, (1998), vol. 79, No. 3, pp. 273-278.
Ward, A. R., "Electrical Stimulation Using Kilohertz-Frequency Alternating Current," Physical Therapy, (2009), vol. 89, No. 2, pp. 181-190.
Wei, P. et al., "Stretchable microelectrode array using room-temperature liquid alloy interconnects," Journal of Micromechanics and Microengineering, (2011), vol. 21, No. 054015, pp. 1-8.
Wenger, N. et al., "Closed-loop neuromodulation of spinal sensorimotor circuits controls refined locomotion after complete spinal cord injury," Science Translational Medicine, (2014), vol. 6, Issue 255, pp. 1-11.
Wenger, N. et al., "Spatiotemporal neuromodulation therapies engaging muscle synergies improve motor control after spinal cord injury—with supplementary material," Natural Medicine, (2016), vol. 22, No. 2, pp. 138-145.
Wenger, N. et al., "Supplementary Materials for Closed-loop neuromodulation of spinal sensorimotor circuits controls refined locomotion after complete spinal cord injury," Science Translational Medicine, (2014), vol. 6, Iss. 255, pp. 1-14.
Wernig, A. et al., "Laufband locomotion with body weight support improved walking in persons with severe spinal cord injuries," International Medical Society of Paraplegia, (1992), vol. 30, No. 4, pp. 229-238.
Wernig, A., "Ineffectiveness of Automated Locomotor Training," Archives of Physical Medicine and Rehabilitation, (2005), vol. 86, No. 12, pp. 2385-2386.
Wessels, M. et al., "Body Weight-Supported Gait Training for Restoration of Walking in People With an Incomplete Spinal Cord Injury: A Systematic Review," Journal of Rehabilitation Medicine, (2010), vol. 42, No. 6, pp. 513-519.
Widmer, C. et al., "Inferring latent task structure for multitask learning by multiple kernel learning," BMC Bioinformatics, (2010), vol. 11, pp. 1-8.
Wiley, J. D. et al., "Analysis and Control of the Current Distribution under Circular Dispersive Electrodes," Biomedical Engineering, IEEE Transactions on BME, (1982), vol. 29, No. 5, pp. 381-385.
Winter, D. et al., "An integrated EMG/biomechanical model of upper body balance and posture during human gait," Progress in Brain Research, (1993), vol. 97, Ch. 32, pp. 359-367.

(56) References Cited

OTHER PUBLICATIONS

Wirz, M. et al., "Effectiveness of automated locomotor training in patients with chronic incomplete spinal cord injury: a multicenter trial," Archives of Physical Medicine and Rehabilitation, (2005), vol. 86, No. 4, pp. 672-680.
Yakovenko, S. et al., "Spatiotemporal Activation of Lumbosacral Motoneurons in the Locomotor Step Cycle," Journal of Neurophysiology, (2002), vol. 87, No. 3, pp. 1542-1553.
YouTube video entitled: "How to Round Corners in Illustrator," uploaded Sep. 6, 2017 by user "Mohamed Achraf" [retrieved on Jul. 7, 2022]. Retrieved from the Internet: <URL:https://www.youtube.com/watch?v=q8Cyd0sqY6A>, 3 pages.
Zhang, T. C. et al., "Mechanisms and models of spinal cord stimulation for the treatment of neuropathic pain," Brain Research, (2014), vol. 1569, pp. 19-31.
Zorner, B. et al., "Profiling locomotor recovery: comprehensive quantification of impairments after CNS damage in rodents," Nature Methods, (2010), vol. 7, No. 9, pp. 701-708.
Office Action in U.S. Appl. No. 16/615,765, mailed Apr. 6, 2023, 18 pages.
Office Action in U.S. Appl. No. 16/953,322, mailed Aug. 29, 2025, 12 pages.
Office Action in U.S. Appl. No. 17/269,970, mailed Jan. 5, 2022, 16 pages.
Office Action in U.S. Appl. No. 17/269,970, mailed Oct. 13, 2022, 21 pages.
Office Action in U.S. Appl. No. 17/269,970, mailed Aug. 16, 2023, 7 pages.
Office Action in U.S. Appl. No. 17/270,402, mailed Apr. 28, 2023, 9 pages.
Office Action in U.S. Appl. No. 17/399,780, mailed Jun. 12, 2025, 12 pages.
Office Action in U.S. Appl. No. 17/407,043, mailed Sep. 13, 2023, 7 pages.
Office Action in U.S. Appl. No. 18/339,085, mailed Sep. 4, 2025, 15 pages.
Office Action in U.S. Appl. No. 29/874,320, mailed Aug. 18, 2025, 9 pages.
Park, K. J. et al., "Continuous "Over and Over" Suture for Tricuspid Ring Annuloplasty," Korean Journal of Thoracic and Cardiovascular Surgery, (2012), vol. 45, No. 1, pp. 19-23.
PeachPit, "Working with Basic Shapes in Adobe Illustrator CC (2014 release)," PeachPit, Nov. 3, 2014 [retrieved on Feb. 6, 2024]. Retrieved from the Internet: <URL: https://www.peachpit.com/articles/article.aspx?p=2253413&seqNum=3>.
Pearson, K. G., "Generating the walking gait: role of sensory feedback," Progress in Brain Research, (2004), vol. 143, Chapter 12, pp. 123-129.
Pellinen, D.S. et al., "Multifunctional Flexible Parylene-Based Intracortical Microelectrodes," Proceedings of the 2005 IEEE: Engineering in Medicine and Biology 27th Annual Conference, (2005), pp. 5272-5275.
Pflug, H. et al., "Parallel Resonant Inductive Wireless Power Transfer," IEEE, Proceedings of Wireless Power Week 2019, London, United Kingdom (2019), pp. 182-187.
Phillips, A. A. et al., "Contemporary Cardiovascular Concerns after Spinal Cord Injury: Mechanisms, Maladaptations, and Management," Journal of Neurotrauma, (2015), vol. 32, No. 24, pp. 1927-1942.
Phillips, A. et al., "Perturbed and spontaneous regional cerebral blood flow responses to changes in blood pressure secondary high-level spinal cord injury: the effect of midodrine," Journal of Applied Physiology, (2014), vol. 116, No. 6, pp. 645-653.
Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, (2014), vol. 34, No. 5, pp. 794-801.
Pratt, G. et al., "Stiffness Isn't Everything," Proceedings of the Fourth International Symposium on Experimental Robotics, (1995), pp. 1-6.
Pratt, J. et al., "Series elastic actuators for high fidelity force control," Industrial Robot: An International Journal, (2002), vol. 29, No. 3, pp. 234-241.
Prochazka, A. et al., "Ensemble firing of muscle afferents recorded during normal locomotion in cats," The Journal of Physiology, (1998), vol. 507, No. 1, pp. 293-304.
Prochazka, A. et al., "Models of ensemble firing of muscle spindle afferents recorded during normal locomotion in cats," The Journal of Physiology, (1998), vol. 507, No. 1, pp. 277-291.
Pudo, D. et al., "Estimating Intensity Fluctuations in High Repetition Rate Pulse Trains Generated Using the Temporal Talbot Effect," IEEE Photonics Technology Letters, (2006), vol. 18, No. 5, pp. 658-660.
Purves, D. et al., "Autonomic Regulation of the Bladder," Neuroscience, 2nd edition, Chapter Twenty-One, Sunderland, (MA), (2022), pp. 1-5.
Rasmussen, C. E. et al., "Gaussian Processes for Machine Learning (GPML) Toolbox," The Journal of Machine Learning Research, (2010), vol. 11, pp. 3011-3015.
Rasmussen, C. E. et al., "Gaussian Processes for Machine Learning," The MIT Press, Cambridge, Massachusetts, (2006), pp. 1-266.
Rasmussen, C. E., "Gaussian Processes in Machine Learning," LNAI, (2003), vol. 3176, pp. 63-71.
Rattay, F. et al., "Epidural electrical stimulation of posterior structures of the human lumbosacral cord: 2. Quantitative analysis by computer modeling," Spinal Cord, (2000), vol. 38, No. 8, pp. 473-489.
Reinkensmeyer, D. et al., "Tools for understanding and optimizing robotic gait training," Journal of Rehabilitation Research & Development, (2006), vol. 43, No. 5, pp. 657-670.
Rejc, E. et al., "Effects of Lumbosacral Spinal Cord Epidural Stimulation for Standing after Chronic Complete Paralysis in Humans," PLoS One, (2015), vol. 10, No. 7, pp. 1-20.
Restriction Requirement in U.S. Appl. No. 16/479,201, mailed Apr. 19, 2022, 9 pages.
Restriction Requirement in U.S. Appl. No. 17/270,402, mailed Dec. 1, 2022, 25 pages.
Robbins, H., "Some Aspects of the Sequential Design of Experiments," Bulletin of the American Mathematical Society, (1952), vol. 58, pp. 527-535.
Robinson, A. et al., "Hybrid stretchable circuits on silicone substrate," Journal of Applied Physics, (2014), vol. 115, No. 14, pp. 143511-1-143511-5.
Rodger, D. C. et al., "High Density Flexible Parylene-Based Multielectrode Arrays for Retinal and Spinal Cord Stimulation," Proc. of the 14th International Conference on Solid-State Sensors, Actuators and Microsystems, (2007), pp. 1385-1888.
Rosenzweig, E. et al., "Extensive Spontaneous Plasticity of Corticospinal Projections After Primate Spinal Cord Injury—with supplementary materials," Nature Neuroscience, (2010), vol. 13, No. 12, pp. 1505-1510.
Roy, F. D. et al., "Effect of percutaneous stimulation at different spinal levels on the activation of sensory and motor roots," Experimental Brain Research, (2012), vol. 223, pp. 281-289.
Rubinstein et al., "Current Density Profiles of Surface Mounted and Recessed Electrodes for Neural Prostheses," Biomedical Engineering, IEEE Transactions on BME, (1987), vol. 34, No. 11, pp. 864-875.
Ryzhov, I. O. et al., "The knowledge gradient algorithm for a general class of online learning problems," Operations Research, (2012), vol. 60, No. 1, pp. 1-47.
Sayenko, D. et al., "Neuromodulation of evoked muscle potentials induced by epidural spinal-cord stimulation in paralyzed individuals," Journal of Neurophysiology, (2014), vol. 111, No. 5, pp. 1088-1099.
Sayenko, D. G. et al., "Spinal segment-specific transcutaneous stimulation differentially shapes activation pattern among motor pools in humans," Journal of Applied Physiology, (2015), vol. 118, No. 11, pp. 1364-1374.

(56) References Cited

OTHER PUBLICATIONS

Schmidlin, E. et al., "Behavioral Assessment of Manual Dexterity in Non-Human Primates," Journal of Visualized Experiments, (2011), vol. 57, No. e3258, pp. 1-11.
Screenshots of the electric patient-reported outcome app final prototype, Researchgate.net, (2020), Retrieved from the Internet: <URL:https://www.researchgate.net/figure/Screenshots-of-the-electronic-patient-reported-outcome-app-final-prototype_fig>, 1 page.
Seifert, H. M. et al., "Restoration of Movement Using Functional Electrical Stimulation and Bayes' Theorem," The Journal of Neuroscience, (2002), vol. 22, No. 21, pp. 9465-9474.
Shafik, A. et al., "Extrapelvic cavernous nerve stimulation in erectile dysfunction. Human Study," Andrologia, (1996), vol. 28, No. 3, pp. 151-156.
Shafik, A. et al., "Magnetic stimulation of the cavernous nerve for the treatment of erectile dysfunction in humans," International Journal of Impotence Research, (2000), vol. 12, No. 3, pp. 137-141.
Shamir, R. et al., "Machine learning approach to optimizing combined stimulation and medication therapies for Parkinson's disease—with supplementary materials," Brain Stimulation, (2015), vol. 8, No. 6, pp. 1025-1032.
Sharpe, A. et al., "Upper-limb muscles responses to epidural, subdural and intraspinal stimulation of the cervical spinal cord," Journal of Neural Engineering, (2014), vol. 11, No. 1, pp. 1-16.
Sherman, J. et al., "Measurements of the normal cervical spinal cord on MR Imaging," American Journal of Neuroradiology, (1990), vol. 11, No. 2, pp. 369-372.
Srinivas, N. et al., "Gaussian process optimization in the bandit setting: No regret and experimental design," In Proceedings of the 27th International Conference on Machine Learning, (2010), pp. 1-17.

* cited by examiner

MULTI-SITE TRANSCUTANEOUS ELECTRICAL STIMULATION OF THE SPINAL CORD FOR FACILITATION OF LOCOMOTION

CROSS-REFERENCE TO RELATED APPLICATIONS

This application is a continuation of U.S. Ser. No. 19/214,843, filed May 21, 2025, which is a continuation of U.S. Ser. No. 17/837,913, filed Jun. 10, 2022, U.S. Pat. No. 12,311,169, which is a continuation of U.S. Ser. No. 15/975,678, filed May 9, 2018, U.S. Pat. No. 11,400,284, which is a continuation of U.S. Ser. No. 14/775,618, filed Sep. 11, 2015, U.S. Pat. No. 9,993,642, which is a U.S. 371 National Phase of PCT/US2014/029340, filed on Mar. 14, 2014, which claims benefit of and priority to U.S. Ser. No. 61/802,034, filed Mar. 15, 2013, all of which are incorporated herein by reference in their entirety for all purposes.

STATEMENT OF GOVERNMENTAL SUPPORT

This invention was made with Government support under NS062009, awarded by the National Institutes of Health. The Government has certain rights in the invention.

FIELD

This application relates to the field of neurological treatment and rehabilitation for injury and disease including traumatic spinal cord injury, non-traumatic spinal cord injury, stroke, movement disorders, brain injury, ALS, Neurodegenerative Disorder, Dementia, Parkinson's disease, and other diseases or injuries that result in paralysis and/or nervous system disorder. Devices, pharmacological agents, and methods are provided to facilitate recovery of posture, locomotion, and voluntary movements of the arms, trunk, and legs, and recovery of autonomic, sexual, vasomotor, speech, swallowing, and respiration, in a human subject having spinal cord injury, brain injury, or any other neurological disorder.

BACKGROUND

Serious spinal cord injuries (SCI) affect approximately 1.3 million people in the United States, and roughly 12-15,000 new injuries occur each year. Of these injuries, approximately 50% are complete spinal cord injuries in which there is essentially total loss of sensory motor function below the level of the spinal lesion.

Neuronal networks formed by the interneurons of the spinal cord that are located in the cervical and lumbar enlargements, such as the spinal networks (SNs), can play an important role in the control of posture, locomotion and movements of the upper limbs, breathing and speech. Most researchers believe that all mammals, including humans, have SNs in the lumbosacral cord. Normally, the activity of SNs is regulated supraspinally and by peripheral sensory input. In the case of disorders of the connections between the brain and spinal cord, e.g., as a result of traumatic spinal cord lesions, motor tasks can be enabled by epidural electrical stimulation of the lumbosacral and cervical segments as well as the brainstem.

SUMMARY

We have demonstrated that enablement of motor function can be obtained as well with the use of non-invasive external spinal cord electrical stimulation.

Various embodiments described herein are for use with a mammal including (e.g., a human or a non-human mammal) who has a spinal cord with at least one selected dysfunctional spinal circuit or other neurologically derived source of control of movement or function in a portion of the subject's body. Transcutaneous electrical spinal cord stimulation (tESCS) can be applied in the regions of the C4-C5, T11-T12 and/or L1-L2 vertebrae with a frequency of 5-40 Hz. Such stimulation can elicit involuntary step-like movements in healthy subjects with their legs suspended in a gravity-neutral position. By way of non-limiting examples, application of transcutaneous electrical spinal cord stimulation (tESCS) at multiple sites on the subject's spinal cord is believed to activate spinal locomotor networks (SNs), in part via the dorsal roots and the gray matter of the spinal cord. When activated, the SNs may, inter alia (a) enable voluntary movement of muscles involved in at least one of standing, stepping, reaching, grasping, voluntarily changing positions of one or both legs, breathing, speech control, swallowing, voiding the patient's bladder, voiding the patient's bowel, postural activity, and locomotor activity; (b) enable or improve autonomic control of at least one of cardiovascular function, body temperature, and metabolic processes; and/or (c) help facilitate recovery of at least one of an autonomic function, sexual function, or vasomotor function. According to some embodiments, the present disclosure provides that the spinal circuitry is neuromodulated to a physiological state that facilitates or enables the recovery or improved control of movement and function following some neuromotor dysfunction.

The paralysis may be a motor complete paralysis or a motor incomplete paralysis. The paralysis may have been caused by a spinal cord injury classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative condition affecting the brain and/or spinal cord. The neurodegenerative brain injury may be associated with at least one of Parkinson's disease, Huntington's disease, Alzheimer's, Frontotemporal Dementia, dystonia, ischemic stroke, amyotrophic lateral sclerosis (ALS), primary lateral sclerosis (PLS), and other conditions such as cerebral palsy and Multiple Sclerosis.

By way of non-limiting example, a method includes applying electrical stimulation to a portion of a spinal cord or brainstem of the subject. The electrical stimulation may be applied by (or through) a surface electrode(s) that is applied to the skin surface of the subject. Such an electrode may be positioned at, at least one of a thoracic region, a cervical region, a thoraco-lumbar region, a lumbosacral region of the spinal cord, the brainstem and/or a combination thereof. In certain embodiments the electrical stimulation is delivered at 5-40 Hz at 20-100 mA. While not a requirement, the electrical stimulation may not directly activate muscle cells in the portion of the patient's body having the paralysis. The electrical stimulation may include at least one of tonic stimulation and intermittent stimulation. The electrical stimulation may include simultaneous or sequential stimulation of different regions of the spinal cord.

If the paralysis was caused by a spinal cord injury at a first location along the spinal cord, the electrical stimulation may be applied by an electrode that is on the spinal cord of the patient at a second location below the first location along the spinal cord relative to the patient's brain.

Optionally, the method may include administering one or more neuropharmaceutical agents to the patient. The neuropharmaceutical agents may include at least one of a serotonergic drug, a dopaminergic drug, a noradrenergic drug, a GABAergic drug, and glycinergic drugs. By way of non-limiting examples, the neuropharmaceutical agents may include at least one of 8-OHDPAT, Way 100.635, Quipazine, Ketanserin, SR 57227A, Ondanesetron, SB 269970, Buspirone, Methoxamine, Prazosin, Clonidine, Yohimbine, SKF-81297, SCH-23390, Quinpirole, and Eticlopride.

The electrical stimulation is defined by a set of parameter values, and activation of the selected spinal circuit may generate a quantifiable result. Optionally, the method may be repeated using electrical stimulation having different sets of parameter values to obtain quantifiable results generated by each repetition of the method. Then, a machine learning method may be executed by at least one computing device. The machine learning method builds a model of a relationship between the electrical stimulation applied to the spinal cord and the quantifiable results generated by activation of the at least one spinal circuit. A new set of parameters may be selected based on the model. By way of a non-limiting example, the machine learning method may implement a Gaussian Process Optimization.

Another illustrative embodiment is a method of enabling one or more functions selected from a group consisting of postural and/or locomotor activity, voluntary movement of leg position when not bearing weight, improved breathing and ventilation, speech control, swallowing, voluntary voiding of the bladder and/or bowel, return of sexual function, autonomic control of cardiovascular function, body temperature control, and normalized metabolic processes, in a human subject having a neurologically derived paralysis. The method includes stimulating the spinal cord of the subject using a surface electrode while subjecting the subject to physical training that exposes the subject to relevant postural proprioceptive signals, locomotor proprioceptive signals, and supraspinal signals. At least one of the stimulation and physical training modulates in real time provoke or incite the electrophysiological properties of spinal circuits in the subject so the spinal circuits are activated by at least one of supraspinal information and proprioceptive information derived from the region of the subject where the selected one or more functions are facilitated.

The region where the selected one or more functions are facilitated may include one or more regions of the spinal cord that control (a) lower limbs; (b) upper limbs and brainstem for controlling speech; (c) the subject's bladder; (d) the subject's bowel and/or other end organ. The physical training may include, but need not be limited to, standing, stepping, sitting down, laying down, reaching, grasping, stabilizing sitting posture, and/or stabilizing standing posture. It is also contemplated that in certain embodiments, the physical training can include, but need not be limited to swallowing, chewing, grimacing, shoulder shrugging, and the like.

The surface electrode may include single electrode(s) or one or more arrays of one or more electrodes stimulated in a monopolar biphasic configuration, a monopolar monophasic configuration, or a bipolar biphasic or monophasic configuration. Such a surface electrode may be placed over at least one of all or a portion of a lumbosacral portion of the spinal cord, all or a portion of a thoracic portion of the spinal cord, all or a portion of a cervical portion of the spinal cord, the brainstem or a combination thereof.

The stimulation may include tonic stimulation and/or intermittent stimulation. The stimulation may include simultaneous or sequential stimulation, or combinations thereof, of different spinal cord regions. Optionally, the stimulation pattern may be under control of the subject.

The physical training may include inducing a load bearing positional change in the region of the subject where locomotor activity is to be facilitated. The load bearing positional change in the subject may include standing, stepping, reaching, and/or grasping. The physical training may include robotically guided training.

The method may also include administering one or more neuropharmaceuticals. The neuropharmaceuticals may include at least one of a serotonergic drug, a dopaminergic drug, a noradrenergic drug, a GABAergic drug, and a glycinergic drug.

Another illustrative embodiment is a method that includes placing an electrode on the patient's spinal cord, positioning the patient in a training device configured to assist with physical training that is configured to induce neurological signals in the portion of the patient's body having the paralysis, and applying electrical stimulation to a portion of a spinal cord of the patient, such as a biphasic signal of 30-40 Hz at 85-100 mA.

Another illustrative embodiment is a system that includes a training device configured to assist with physically training of the patient, a surface electrode array configured to be applied on the patient's spinal cord, and a stimulation generator connected to the electrode. When undertaken, the physical training induces neurological signals in the portion of the patient's body having the paralysis. The stimulation generator is configured to apply electrical stimulation to the electrode. Electrophysiological properties of at least one spinal circuit in the patient's spinal cord is modulated by the electrical stimulation and at least one of (1) a first portion of the induced neurological signals and (2) supraspinal signals such that the at least one spinal circuit is at least partially activatable by at least one of (a) the supraspinal signals and (b) a second portion of the induced neurological signals.

Definitions

The term "motor complete" when used with respect to a spinal cord injury indicates that there is no motor function below the lesion, (e.g., no movement can be voluntarily induced in muscles innervated by spinal segments below the spinal lesion.

As used herein "electrical stimulation" or "stimulation" means application of an electrical signal that may be either excitatory or inhibitory to a muscle or neuron. It will be understood that an electrical signal may be applied to one or more electrodes with one or more return electrodes.

The term "monopolar stimulation" refers to stimulation between a local electrode and a common distant return electrode.

As used herein "epidural" means situated upon the dura or in very close proximity to the dura. The term "epidural stimulation" refers to electrical epidural stimulation. In certain embodiments epidural stimulation is referred to as "electrical enabling motor control" (eEmc).

The term "transcutaneous stimulation" or "transcutaneous electrical stimulation" or "cutaneous electrical stimulation" refers to electrical stimulation applied to the skin, and, as typically used herein refers to electrical stimulation applied to the skin in order to effect stimulation of the spinal cord or a region thereof. The term "transcutaneous electrical spinal cord stimulation" may also be referred to as "tSCS".

The term "autonomic function" refers to functions controlled by the peripheral nervous system that are controlled largely below the level of consciousness, and typically involve visceral functions. Illustrative autonomic functions include, but are not limited to control of bowel, bladder, and body temperature.

The term "sexual function" refers to the ability to sustain a penile erection, have an orgasm (male or female), generate viable sperm, and/or undergo an observable physiological change associated with sexual arousal.

The term "co-administering", "concurrent administration", "administering in conjunction with" or "administering in combination" when used, for example with respect to transcutaneous electrical stimulation, epidural electrical stimulation, and pharmaceutical administration, refers to administration of the transcutaneous electrical stimulation and/or epidural electrical stimulation and/or pharmaceutical such that various modalities can simultaneously achieve a physiological effect on the subject. The administered modalities need not be administered together, either temporally or at the same site. In some embodiments, the various "treatment" modalities are administered at different times. In some embodiments, administration of one can precede administration of the other (e.g., drug before electrical stimulation or vice versa). Simultaneous physiological effect need not necessarily require presence of drug and the electrical stimulation at the same time or the presence of both stimulation modalities at the same time. In some embodiments, all the modalities are administered essentially simultaneously.

BRIEF DESCRIPTION OF THE DRAWINGS

FIG. 5 shows angular movements of the right (R) knee and left (L) knee joints and representative EMG activity in the rectus femoris (RF), biceps femoris (BF) tibialis anterior (TA) and medial gastrocnemius (MG) muscles during involuntary locomotor-like activity induced by transcutaneous spinal cord stimulation at the T11 vertebra at 5 and 30 Hz. FIG. 5B shows stick diagram decompositions (40 ms between sticks) of the movements of the R leg and trajectory of toe movements during one step cycle during PTES at T11-T12. Arrows in FIG. 5B indicate the direction of movement.

DETAILED DESCRIPTION

Figure 1:
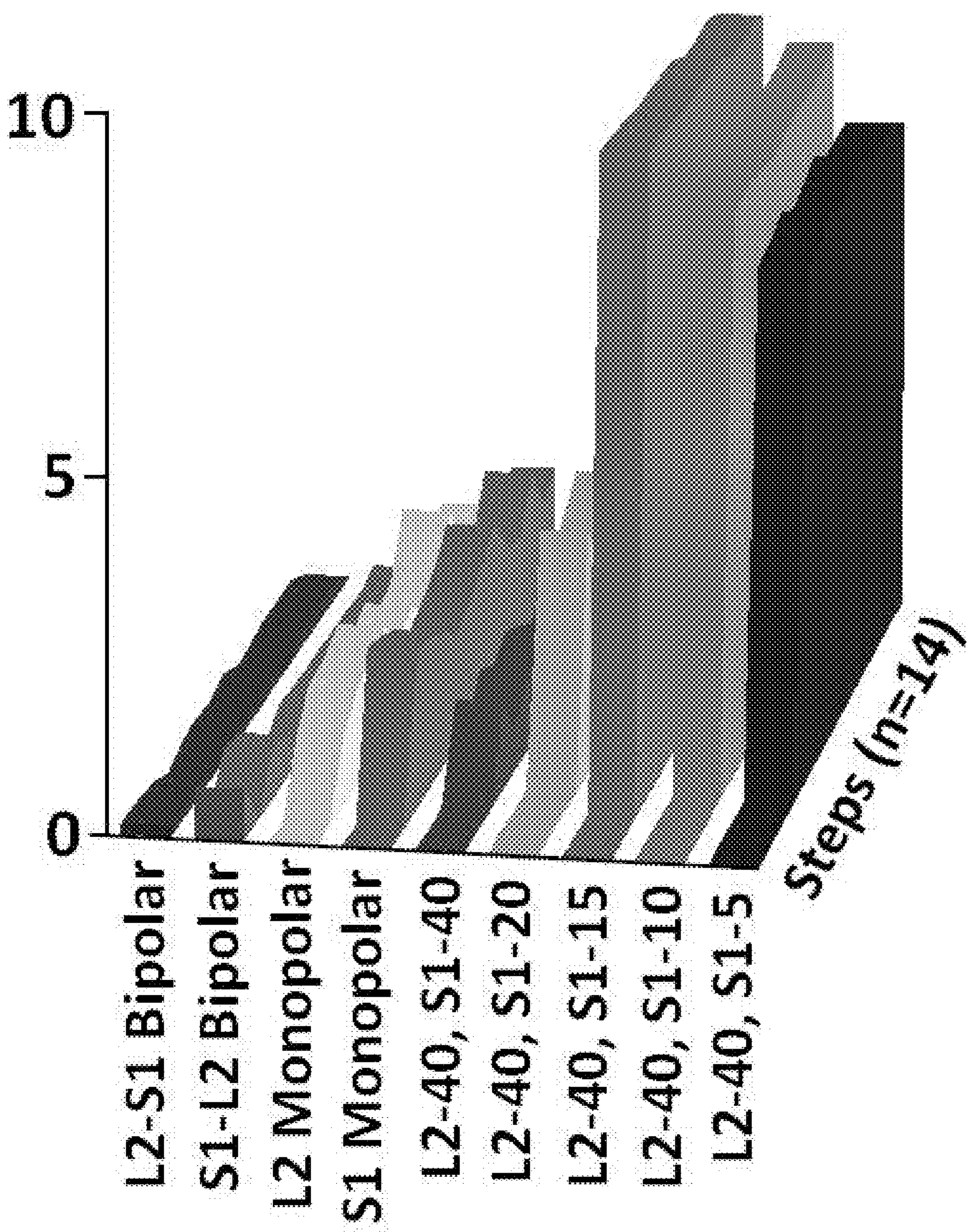
FIG. 1 is an example embodiment illustrating peak EMG amplitudes in the vastus lateralis in response to epidural stimulation at L2 and/or S1 spinal segments using nine combinations.

Disclosed herein are methods for inducing locomotor activity in a mammal. These methods can comprise administering epidural or transcutaneous electrical spinal cord stimulation (tSCS) to the mammal at a frequency and intensity that induces the locomotor activity.

It is demonstrated herein in spinal rats (motor complete rats) and non-injured human subjects that simultaneous spinal cord stimulation at multiple sites has an interactive effect on the spinal neural circuitries responsible for generating locomotion. In particular, it was discovered inter alia, that simultaneous multisite epidural stimulation with specific parameters allows for a more precise control of these postural-locomotor interactions, resulting in robust, coordinated plantar full weight-bearing stepping in complete spinal rats. The EMG stepping pattern during simultaneous multisite epidural stimulation was significantly improved compared to certain bipolar stimulation configurations (e.g., between L2 and S1) or certain monopolar stimulation configurations (e.g., at L2 or S1). Without being bound to a particular theory it is believed that one added benefit of second-site (e.g., S1 added to L2) stimulation with specific parameters may be related to activation of postural neuronal circuitries and activation of rostrally projecting propriospinal neurons from the more caudal segments that contribute to the rhythm and pattern of output of the locomotor circuitry.

It is also demonstrated herein using transcutaneous spinal cord stimulation in non-injured humans that the lumbosacral locomotor circuitry can be accessed using a non-invasive pain free procedure. In an illustrative, but non-limiting embodiment, it is shown that transcutaneous spinal cord stimulation applied to stimulation at the L2 spinal segment (T11-T12 vertebral level) is able to activate this locomotor circuitry. It is believed the results demonstrated herein provide the first example of using multi-segmental non-invasive electrical spinal cord stimulation to facilitate involuntary, coordinated stepping movements.

Without being bound by a particular theory, it is believed that the synergistic and interactive effects of multi-level stimulation in both the animal and human studies indicates a multi-segmental convergence of descending and ascending, and most likely propriospinal, influences on the spinal neuronal circuitries associated with locomotor and postural activity.

Accordingly, in some embodiments, the electrical spinal cord stimulation is applied at two spinal levels simultaneously. In other embodiments, the electrical spinal cord stimulation is applied at three spinal levels simultaneously. In still over embodiments the electrical spinal cord stimulation is at four spinal levels simultaneously. The spinal levels can be the cervical, thoracic, lumbar, sacral, or a combination thereof. In certain embodiments the spinal levels can be the cervical, thoracic, lumbar, or a combination thereof.

In certain embodiments, the stimulation can be to a brain stem and/or cervical level. In some embodiments, the brainstem/cervical level can be a region over at least one C0-C7 or C1-C7, over at least two of C0-C7 or C1-C7, over at least three of C0-C7 or C1-C7, over at least four of C0-C7 or C1-C7, over at least five of C0-C7 or C1-C7, over at least six of C0-C7 or C1-C7, over C1-C7, over C4-C5, over C3-C5, over C4-C6, over C3-C6, over C2-C5, over C3-C7, or over C3 to C7.

Additionally or alternatively, the stimulation can be to a thoracic level. In some embodiments, the thoracic level can be a region over at least one of T1 to T12, at least two of T1 to T12, at least three of T1 to T12, at least four of T1 to T12, at least five of T1 to T12, at least six of T1 to T12, at least seven of T1 to T12, at least 8 of T1 to T12, at least 9 of T1 to T12, at least 10 of T1 to T12, at least 11 of T1 to T12, T1 to T12, over T1 to T6, or over a region of T11-T12, T10-T12, T9-T12, T8-T12, T8-T11, T8 to T10, T8 to T9, T9-T12, T9-T11, T9-T10, or T11-T12.

Additionally or alternatively, the stimulation can be to a lumbar level. In some embodiments, the lumbar level can be a region over at least one of L1-L5, over at least two of L1-L5, over at least three of L1-L5, over at least four of L1-L5, or L1-L5.

Additionally or alternatively, the stimulation can be to a sacral level. In some embodiments, the sacral level can be a region over at least one S1-S5, over at least two of S1-S5, over late least three of S1-S5, over at least four of S1-S5, or over S1-S5. In certain embodiments, the stimulation is over a region including S1. In certain embodiments, the stimulation over a sacral level is over S1.

In some embodiments, the transcutaneous electrical spinal cord stimulation is applied paraspinally over regions that include, but need not be limited to C4-C5, T11-T12, and/or L1-L2 vertebrae. In some embodiments, the transcutaneous electrical spinal cord stimulation is applied paraspinally over regions that consist of regions over C4-C5, T11-T12, and/or L1-L2 vertebrae.

In various embodiments, the transcutaneous stimulation can be applied at an intensity ranging from about 30 to 200 mA, about 110 to 180 mA, about 10 mA to about 150 mA, from about 20 mA to about 100 mA, or from about 30 or 40 mA to about 70 mA or 80 mA.

In various embodiments the transcutaneous stimulation can be applied at a frequency ranging from about 1 Hz to about 100 Hz, from about 5 Hz to about 80 Hz, or from about 5 Hz to about 30 Hz, or about 40 Hz, or about 50 Hz.

As demonstrated herein, non-invasive transcutaneous electrical spinal cord stimulation (tSCS) can induce locomotor-like activity in non-injured humans. Continuous tSCS (e.g., at 5-40 Hz) applied paraspinally over the T11-T12 vertebrae can induce involuntary stepping movements in subjects with their legs in a gravity-independent position. These stepping movements can be enhanced when the spinal cord is stimulated at two to three spinal levels (C5, T12, and/or L2) simultaneously with frequency in the range of 5-40 Hz. Further, locomotion of spinal animals can be improved, in some embodiments substantially, when locomotor and postural spinal neuronal circuitries are stimulated simultaneously.

In some embodiments, epidural spinal cord stimulation can be applied independently at the L2 and at the S1 spinal segments to facilitate locomotion as demonstrated herein in complete spinal adult rats. Simultaneous epidural stimulation at L2 (40 Hz) and at S1 (10-20 Hz) can enable full weight-bearing plantar hindlimb stepping in spinal rats. Stimulation at L2 or S1 alone can induce rhythmic activity, but, in some embodiments, with minimal weight bearing. In non-injured human subjects with the lower limbs placed in a gravity-neutral position, transcutaneous electrical stimulation (5 Hz) delivered simultaneously at the C5, T11, and L2 vertebral levels facilitated involuntary stepping movements that were significantly stronger than stimulation at T11 alone. Accordingly, simultaneous spinal cord stimulation at multiple sites can have an interactive effect on the spinal circuitry responsible for generating locomotion.

By non-limiting example, transcutaneous electrical stimulation can be applied to facilitate restoration of locomotion and other neurologic function in subjects suffering with spinal cord injury, as well as other neurological injury and illness. Successful application can provide a device for widespread use in rehabilitation of neurologic injury and disease.

In embodiments, methods, devices, and optional pharmacological agents are provided to facilitate movement in a mammalian subject (e.g., a human) having a spinal cord injury, brain injury, or other neurological disease or injury. In some embodiments, the methods can involve stimulating the spinal cord of the subject using a surface electrode where the stimulation modulates the electrophysiological properties of selected spinal circuits in the subject so they can be activated by proprioceptive derived information and/or input from supraspinal. In various embodiments, the stimulation may be accompanied by physical training (e.g., movement) of the region where the sensory-motor circuits of the spinal cord are located.

In some embodiments, the devices, optional pharmacological agents, and methods described herein stimulate the spinal cord with, e.g., electrodes that modulate the proprioceptive and supraspinal information which controls the lower limbs during standing and/or stepping and/or the upper limbs during reaching and/or grasping conditions. It is the proprioceptive and cutaneous sensory information that guides the activation of the muscles in a coordinated manner and in a manner that accommodates the external conditions, e.g., the amount of loading, speed, and direction of stepping or whether the load is equally dispersed on the two lower limbs, indicating a standing event, alternating loading indicating stepping, or sensing postural adjustments signifying the intent to reach and grasp.

Unlike approaches that involve specific stimulation of motor neurons to directly induce a movement, the methods described herein enable the spinal circuitry to control the movements. More specifically, the devices, optional pharmacological agents, and methods described herein can exploit the spinal circuitry and its ability to interpret proprioceptive information and to respond to that proprioceptive information in a functional way. In various embodiments, this is in contrast to other approaches where the actual movement is induced/controlled by direct stimulation (e.g., of particular motor neurons).

In one embodiment, the subject is fitted with one or more surface electrodes that afford selective stimulation and control capability to select sites, mode(s), and intensity of stimulation via electrodes placed superficially over, for example, the lumbosacral spinal cord and/or the thoracic spinal cord, and/or the cervical spinal cord to facilitate movement of the arms and/or legs of individuals with a severely debilitating neuromotor disorder.

In some embodiments, the subject is provided a generator control unit and is fitted with an electrode(s) and then tested to identify the most effective subject specific stimulation paradigms for facilitation of movement (e.g., stepping and standing and/or arm and/or hand movement). Using the herein described stimulation paradigms, the subject practices standing, stepping, reaching, grabbing, breathing, and/or speech therapy in an interactive rehabilitation program while being subject to spinal stimulation.

Depending on the site/type of injury and the locomotor activity it is desired to facilitate, particular spinal stimulation protocols include, but are not limited to, specific stimulation sites along the lumbosacral, thoracic, cervical spinal cord or a combination thereof; specific combinations of stimulation sites along the lumbosacral, thoracic, cervical spinal cord and/or a combination thereof; specific stimulation amplitudes; specific stimulation polarities (e.g., monopolar and bipolar stimulation modalities); specific stimulation frequencies; and/or specific stimulation pulse widths.

In various embodiments, the system is designed so that the patient can use and control in the home environment.

In various embodiments, the electrodes of electrode arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using, e.g., constant current or constant voltage delivery of the stimulation.

In one illustrative but non-limiting system a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to use or receive instructions from a programmer (or another source). Thus, in certain embodiments the pulse generator/controller is configurable by software and the control parameters may be programmed/entered locally, or downloaded as appropriate/necessary from a remote site.

In certain embodiments the pulse generator/controller may include or be operably coupled to memory to store instructions for controlling the stimulation signal(s) and may contain a processor for controlling which instructions to send for signal generation and the timing of the instructions to be sent.

While in certain embodiments, two leads are utilized to provide transcutaneous stimulation, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in one or more regions of the spine. A return electrode such as a ground or other reference electrode can be located on same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

In various embodiments, the approach is not to electrically induce a walking pattern or standing pattern of activation, but to enable/facilitate it so that when the subject manipulates their body position, the spinal cord can receive proprioceptive information from the legs (or arms) that can be readily recognized by the spinal circuitry. Then, the spinal cord knows whether to step or to stand or to do nothing. In other words, this enables the subject to begin stepping or to stand or to reach and grasp when they choose after the stimulation pattern has been initiated.

Moreover, the methods and devices described herein are effective in a spinal cord injured subject that is clinically classified as motor complete; that is, there is no motor function below the lesion; however the approach is not limited and may be used in subjects classified as motor-incomplete. In various embodiments, the specific combination of electrode(s) activated/stimulated and/or the desired stimulation of any one or more electrodes and/or the stimulation amplitude (strength) can be varied in real time, e.g., by the subject. Closed loop control can be embedded in the process by engaging the spinal circuitry as a source of feedback and feedforward processing of proprioceptive input and by voluntarily imposing fine tuning modulation in stimulation parameters based on visual, and/or kinetic, and/or kinematic input from selected body segments.

In various embodiments, the devices, optional pharmacological agents, and methods are designed so that a subject with no voluntary movement capacity can execute effective standing and/or stepping and/or reaching and/or grasping. In addition, the approach described herein can play an important role in facilitating recovery of individuals with severe although not complete injuries.

The approach described herein can provide some basic postural, locomotor and reaching and grasping patterns on their own. However, in some embodiments, the methods described herein can also serve as building blocks for future recovery strategies. In other embodiments, combining transcutaneous stimulation of appropriate spinal circuits with physical rehabilitation and pharmacological intervention can provide practical therapies for complete SCI human patients. The methods described herein can be sufficient to enable weight bearing standing, stepping and/or reaching or grasping in SCI patients. Such capability can give SCI patients with complete paralysis or other neuromotor dysfunctions the ability to participate in exercise, which can be beneficial, if not highly beneficial, for their physical and mental health.

In other embodiments, the methods described herein can enable movement with the aid of assistive walkers. In some embodiments, simple standing and short duration walking can increase these patients' autonomy and quality of life. The stimulating technology described herein (e.g., transcutaneous electrical spinal cord stimulation) can provide a direct brain-to-spinal cord interface that can enable more lengthy and finer control of movements.

While the methods and devices described herein are discussed with reference to complete spinal injury, it will be recognized that they can apply to subjects with partial spinal injury, subjects with brain injuries (e.g., ischemia, traumatic brain injury, stroke, and the like), and/or subjects with neurodegenerative diseases (e.g., Parkinson's disease, Alzheimer's disease, Huntington's disease, amyotrophic lateral sclerosis (ALS), primary lateral sclerosis (PLS), cerebral palsy, dystonia, and the like).

In various embodiments, the methods combine the use of transcutaneous stimulating electrode(s) with physical training (e.g., rigorously monitored (robotic) physical training), optionally in combination with pharmacological techniques. The methods enable the spinal cord circuitry to utilize sensory input as well as newly established functional connections from the brain to circuits below the spinal lesion as a source of control signals. The herein described methods can enable and facilitate the natural sensory input as well as supraspinal connections to the spinal cord in order to control movements, rather than induce the spinal cord to directly induce the movement. That is, the presently described methods can facilitate and enhance intrinsic neural control mechanisms of the spinal cord that exist post-SCI, rather than replace or ignore them.

Processing of Sensory Input by the Spinal Cord: Using Afferents as a Source of Control In various embodiments the methods and devices described herein can exploit spinal control of locomotor activity. For example, the human spinal cord can receive sensory input associated with a movement such as stepping, and this sensory information can be used to modulate the motor output to accommodate the appropriate speed of stepping and level of load that is imposed on lower limbs. In some embodiments, the present methods can utilize the central-pattern-generation-like properties of the human spinal cord (e.g., the lumbosacral spinal cord). Thus, for example, exploiting inter alia the central-pattern-generation-like properties of the lumbosacral spinal cord, oscillations of the lower limbs can be induced simply by vibrating the vastus lateralis muscle of the lower limb, by transcutaneous stimulation, and by stretching the hip. The methods described herein exploit the fact that the human spinal cord, in complete or incomplete SCI subjects, can receive and interpret proprioceptive and somatosensory information that can be used to control the patterns of neuromuscular activity among the motor pools necessary to generate particular movements, e.g., standing, stepping, reaching, grasping, and the like.

Moreover, in certain embodiments, the methods described herein exploit the fact that stimulation (e.g., transcutaneous stimulation) of multiple levels can improve the ability of the spinal cord in complete or incomplete SCI subjects to receive and interpret proprioceptive and somatosensory information that can be used to control the patterns of neuromuscular activity among the motor pools necessary to generate particular movements In various embodiments, The methods described herein can facilitate and adapt the operation of the existing spinal circuitry that generates, for example, cyclic step-like movements via a combined approach of transcutaneous stimulation, physical training, and, optionally, pharmacology.

Facilitating Stepping and Standing in Humans Following a Clinically Complete Lesion In various embodiments, the methods described herein can comprise stimulation of one or more regions of the spinal cord in combination with locomotory activities. In other embodiments, spinal stimulation can be combined with locomotor activity thereby providing modulation of the electrophysiological properties of spinal circuits in the subject so they are activated by proprioceptive information derived from the region of the subject where locomotor activity is to be facilitated. Further, spinal stimulation in combination with pharmacological agents and locomotor activity may result in the modulation of the electrophysiological properties of spinal circuits in the subject so they are activated by proprioceptive information derived from the region of the subject where locomotor activity is to be facilitated.

In certain embodiments of the presently described methods, locomotor activity of the region of interest can be assisted or accompanied by any of a number of methods known, for example, to physical therapists. By way of illustration, individuals after severe SCI can generate standing and stepping patterns when provided with body weight support on a treadmill and manual assistance. During both stand and step training of human subjects with SCI, the subjects can be placed on a treadmill in an upright position and suspended in a harness at the maximum load at which knee buckling and trunk collapse can be avoided. Trainers positioned, for example, behind the subject and at each leg assist as needed in maintaining proper limb kinematics and kinetics appropriate for each specific task. During bilateral standing, both legs can be loaded simultaneously and extension can be the predominant muscular activation pattern, although co-activation of flexors can also occur. Additionally, or alternatively, during stepping the legs can be loaded in an alternating pattern and extensor and flexor activation patterns within each limb also alternated as the legs moved from stance through swing. Afferent input related to loading and stepping rate can influence these patterns, and training has been shown to improve these patterns and function in clinically complete SCI subjects.

Transcutaneous Electrical Stimulation of the Spinal Cord

As indicated above, without being bound by a particular theory, it is believed that transcutaneous electrical stimulation, e.g., over one spinal level, over two spinal levels simultaneously, or over three spinal levels simultaneously, in combination with physical training can facilitate recovery of stepping and standing in human subjects following a complete SCI.

In some embodiments, the location of electrode(s) and the stimulation parameters may be important in defining the motor response. In other embodiments, the use of surface electrode(s), as described herein, facilitates selection or alteration of particular stimulation sites as well as the application of a wide variety of stimulation parameters.

Use of Neuromodulatory Agents

In certain embodiments, the transcutaneous and/or epidural stimulation methods described herein are used in conjunction with various pharmacological agents, particularly pharmacological agents that have neuromodulatory activity (e.g., are monoamergic). In certain embodiments, the use of various serotonergic, and/or dopaminergic, and/or noradrenergic and/or GABAergic, and/or glycinergic drugs is contemplated. These agents can be used in conjunction with the stimulation and/or physical therapy as described above. This combined approach can help to put the spinal cord (e.g., the cervical spinal cord) in an optimal physiological state for controlling a range of hand movements.

In certain embodiments, the drugs are administered systemically, while in other embodiments, the drugs are administered locally, e.g., to particular regions of the spinal cord. Drugs that modulate the excitability of the spinal neuromotor networks include, but are not limited to combinations of noradrenergic, serotonergic, GABAergic, and glycinergic receptor agonists and antagonists. Illustrative pharmacological agents include, but are not limited to. agonists and antagonists to one or more combinations of serotonergic: 5-HT1A, 5-HT2A, 5-HT3, and 5HT7 receptors; to noradrenergic alpha1 and 2 receptors; and to dopaminergic D1 and D2 receptors (see, e.g., Table 1).

TABLE 1

Illustrative pharmacological agents.

| Name | Target | Action | Route | Typical Dose (mg/Kg) | Typical Range (mg/kg) |
|---|---|---|---|---|---|
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| Quipazine | 5-HT2A/C | Agonist | I.P. | 0.2 | 0.18-0.6 |
| Ketanserin | 5-HT2A/C | Antagonist | I.P. | 3 | 1.5-6.0 |
| SR 57227A | 5-HT3 | Agonist | I.P. | 1.5 | 1.3-1.7 |
| Ondanesetron | 5-HT3 | Antagonist | I.P. | 3 | 1.4-7.0 |
| SB269970 | 5-HT7 | Antagonist | I.P. | 7 | 2.0-10.0 |
| Noradrenergic receptor systems | | | | | |
| Methoxamine | Alpha1 | Agonist | I.P. | 2.5 | 1.5-4.5 |
| Prazosin | Alpha1 | Antagonist | I.P. | 3 | 1.8-3.0 |
| Clonidine | Alpha2 | Agonist | I.P. | 0.5 | 0.2-1.5 |
| Yohimbine | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| Quinipirole | D2-like | Agonist | I.P. | 0.3 | 0.15-0.3 |
| Eticlopride | D2-like | Antagonist | I.P. | 1.8 | 0.9-1.8 |

The foregoing methods are intended to be illustrative and non-limiting. Using the teachings provided herein, other methods involving transcutaneous electrical stimulation and/or epidural electrical stimulation and/or the use of neuromodulatory agents to improve motor control and/or strength of a hand or paw will be available to one of skill in the art.

In various aspects, the invention(s) contemplated herein may include, but need not be limited to, any one or more of the following embodiments:

Embodiment 1: A method of inducing locomotor activity in a mammal, said method including administering transcutaneous electrical spinal cord stimulation (tSCS) to said mammal at a frequency and intensity that induces said locomotor activity.

Embodiment 2: The method of embodiment 1, wherein said mammal is a human.

Embodiment 3: The method of embodiment 2, wherein said electrical spinal cord stimulation is applied at two spinal levels simultaneously.

Embodiment 4: The method of embodiment 3, wherein said two spinal levels are selected from cervical thoracic, lumbar or combinations thereof.

Embodiment 5: The method of embodiment 4, wherein said two spinal levels include cervical and thoracic.

Embodiment 6: The method of embodiment 4, wherein said two spinal levels include cervical and lumbar.

Embodiment 7: The method of embodiment 4, wherein said two spinal levels include thoracic and lumbar.

Embodiment 8: The method of embodiment 2, wherein said electrical spinal cord stimulation is applied at three spinal levels simultaneously.

Embodiment 9: The method according to any one of embodiments 3-8, wherein stimulation to a cervical level is to a region over at least one C1-C7, over at least two of C1-C7, over late least three of C1-C7, over at least four of C1-C7, over at least five of C1-C7, over at least six of C1-C7, or over C1-C7.

Embodiment 10: The method according to any one of embodiments 3-8, wherein stimulation to a cervical level is to a region over C4-C5, over C3-C5, over C4-C6, over C3-C6, over C2-C5, over C3-C7, or over C3 to C7.

Embodiment 11: The method according to any one of embodiments 3-10, wherein stimulation to a thoracic level is to a region over at least one of T1 to T12, at least two of T1 to T12, at least three of T1 to T12, at least four of T1 to T12, at least five of T1 to T12, at least six of T1 to T12, at least seven of T1 to T12, at least 8 of T1 to T12, at least 9 of T1 to T12, at least 10 of T1 to T12, at least 11 of T1 to T12, or T1 to T12.

Embodiment 12: The method of embodiment 11, wherein stimulation to a thoracic level is to a region over T1 to T6, over a region of T11-T12, T10-T12, T9-T12, T8-T12, T8-T11, T8 to T10, T8 to T9, T9-T12, T9-T11, T9-T10, or T11-T12.

Embodiment 13: The method according to any one of embodiments 3-10, wherein stimulation to a lumbar level is to a region over at least one of L1-L5, over at least two of L1-L5, over at least three of L1-L5, over at least four of L1-L5, or L1-L5.

Embodiment 14: The method of embodiment 2-3, wherein said transcutaneous electrical spinal cord stimulation is applied paraspinally over C4-C5, T11-T12, or L1-L2 vertebrae.

Embodiment 15: The method according to any one of embodiments 2-3, and 8, wherein said transcutaneous electrical spinal cord stimulation is applied paraspinally over regions including one or more of C4-C5, T11-T12, or L1-L2 vertebrae.

Embodiment 16: The method of embodiment 15, wherein said transcutaneous electrical spinal cord stimulation is applied paraspinally over regions including two or more of C4-C5, T11-T12, or L1-L2 vertebrae.

Embodiment 17: The method according to any one of embodiments 2-3, and 8, wherein said transcutaneous electrical spinal cord stimulation is applied paraspinally over one or more of C4-C5, T11-T12, or L1-L2 vertebrae.

Embodiment 18: The method of embodiment 17, wherein said transcutaneous electrical spinal cord stimulation is applied paraspinally over two or more of C4-C5, T11-T12, or L1-L2 vertebrae.

Embodiment 19: The method of embodiment 17, wherein said transcutaneous electrical spinal cord stimulation is applied paraspinally over C4-C5, T11-T12, and L1-L2 vertebrae.

Embodiment 20: The method according to any one of embodiments 1-21, wherein said transcutaneous electrical stimulation is painless transcutaneous electrical stimulation (PTES).

Embodiment 21: The method according to any one of embodiments 1-20, wherein said transcutaneous stimulation is applied at an intensity ranging from about 30 to 200 mA, about 110 to 180 mA, about 10 mA to about 150 mA, from about 20 mA to about 100 mA, from about 30 or 40 mA to about 70 mA or 80 mA.

Embodiment 22: The method according to any one of embodiments 1-21, wherein said transcutaneous stimulation is applied at a frequency ranging from about 1 Hz to about 100 Hz, from about 3 Hz to about 90 Hz, from about 5 Hz to about 80 Hz, from about 5 Hz to about 30 Hz, or about 40 Hz, or about 50 Hz.

Embodiment 23: The method according to any one of embodiments 1-22, wherein said mammal has a spinal cord injury.

Embodiment 24: The method of embodiment 23, wherein said spinal cord injury is clinically classified as motor complete.

Embodiment 25: The method of embodiment 23, wherein said spinal cord injury is clinically classified as motor incomplete.

Embodiment 26: The method according to any one of embodiments 1-22, wherein said mammal has an ischemic brain injury.

Embodiment 27: The method of embodiment 26, wherein said ischemic brain injury is brain injury from stroke or acute trauma.

Embodiment 28: The method according to any one of embodiments 1-22, wherein said mammal has a neurodegenerative brain injury.

Embodiment 29: The method of embodiment 28, wherein said neurodegenerative brain injury is brain injury associated with a condition selected from the group consisting of Parkinson's disease, Huntington's disease, Alzheimers, ischemic, stroke, amyotrophic lateral sclerosis (ALS), primary lateral sclerosis (PLS), dystonia, and cerebral palsy.

Embodiment 30: The method according to any one of embodiments 1-29, wherein said locomotor/motor activity includes standing, stepping, reaching, grasping, speech, swallowing, or breathing.

Embodiment 31: The method according to any one of embodiments 1-30, wherein said locomotor activity includes a walking motor pattern.

Embodiment 32: The method according to any one of embodiments 1-31, wherein said locomotor activity includes sitting down, laying down, sitting up, or standing up.

Embodiment 33: The method according to any one of embodiments 1-32, wherein the stimulation is under control of the subject.

Embodiment 34: The method according to any one of embodiments 1-33, wherein said method further includes physical training of said mammal.

Embodiment 35: The method of embodiment 34, wherein said physical training includes inducing a load bearing positional change in said mammal.

Embodiment 36: The method according to embodiment 34, wherein the load bearing positional change in said subject includes standing.

Embodiment 37: The method according to embodiment 34, wherein the load bearing positional change in said subject includes stepping.

Embodiment 38: The method according to any one of embodiments 34-37, wherein said physical training includes robotically guided training.

Embodiment 39: The method according to any one of embodiments 1-38, wherein said method further includes administration of one or more neuropharmaceuticals.

Embodiment 40: The method of embodiment 39, wherein said neuropharmaceutical includes one or more agents selected from the group consisting of a serotonergic drug, a dopaminergic drug, and a noradrenergic drug.

Embodiment 41: The method of embodiment 39, wherein said neuropharmaceutical includes a serotonergic drug.

Embodiment 42: The method of embodiment 41, wherein said neuropharmaceutical includes the serotonergic drug 8-OHDPAT.

Embodiment 43: The method according to any one of embodiments 39-42, wherein said neuropharmaceutical includes the serotonergic drug Way 100.635.

Embodiment 44: The method according to any one of embodiments 39-43, wherein said neuropharmaceutical includes the serotonergic drug Quipazine.

Embodiment 45: The method according to any one of embodiments 39-44, wherein said neuropharmaceutical includes the serotonergic drug Ketanserin, SR 57227A.

Embodiment 46: The method according to any one of embodiments 39-45, wherein said neuropharmaceutical includes the serotonergic drug Ondanesetron.

Embodiment 47: The method according to any one of embodiments 39-46, wherein said neuropharmaceutical includes the serotonergic drug SB269970.

Embodiment 48: The method according to any one of embodiments 39-47, wherein said neuropharmaceutical includes a dopaminergic drug.

Embodiment 49: The method according to any one of embodiments 39-48, wherein said neuropharmaceutical includes the dopaminergic drug SKF-81297.

Embodiment 50: The method according to any one of embodiments 39-49, wherein said neuropharmaceutical includes the dopaminergic drug SCH-23390.

Embodiment 51: The method according to any one of embodiments 39-50, wherein said neuropharmaceutical includes the dopaminergic drug Quinpirole.

Embodiment 52: The method according to any one of embodiments 39-51, wherein said neuropharmaceutical includes the dopaminergic drug Eticlopride.

Embodiment 53: The method according to any one of embodiments 39-52, wherein said neuropharmaceutical includes a noradrenergic drug.

Embodiment 54: The method according to any one of embodiments 39-53, wherein said neuropharmaceutical includes the noradrenergic drug Methoxamine.

Embodiment 55: The method according to any one of embodiments 39-54, wherein said neuropharmaceutical includes the noradrenergic drug Prazosin.

Embodiment 56: The method according to any one of embodiments 39-55, wherein said neuropharmaceutical includes the noradrenergic drug Clonidine.

Embodiment 57: The method according to any one of embodiments 39-56, wherein said neuropharmaceutical includes the noradrenergic drug Yohimbine.

Embodiment 58: An electrical stimulator said stimulator configured to induce locomotor or motor activity in a mammal according to anyone of embodiments 1-54.

Embodiment 59: An electrical stimulator according to embodiment 58 in combination with the pharmaceutical as recited in any one of embodiments 39-57 for use in inducing or restoring locomotor function in a mammal.

Embodiment 60: The electrical stimulator of embodiment 59, wherein said mammal has a spinal cord injury.

Embodiment 61: The electrical stimulator of embodiment 60, wherein said spinal cord injury is clinically classified as motor complete.

Embodiment 62: The electrical stimulator of embodiment 60, wherein said spinal cord injury is clinically classified as motor incomplete.

Embodiment 63: The electrical stimulator of embodiment 60, wherein said mammal has an ischemic brain injury.

Embodiment 64: The electrical stimulator of embodiment 63, wherein said ischemic brain injury is brain injury from stroke or acute trauma.

Embodiment 65: The electrical stimulator of embodiment 60, wherein said mammal has a neurodegenerative brain injury.

Embodiment 66: The electrical stimulator of embodiment 65, wherein said neurodegenerative brain injury is brain injury associated with a condition selected from the group consisting of Parkinson's disease, Huntington's disease, Alzheimer's, ischemic, stroke, amyotrophic lateral sclerosis (ALS), primary lateral sclerosis (PLS), dystonia, and cerebral palsy.

Illustrative, but non-limiting embodiments of the contemplated are described herein. Variations on these embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context

EXAMPLES

The following examples are offered to illustrate, but not to limit the claimed invention.

Example 1

Six non-injured individuals were tested while lying on their right side with their legs supported in a gravity-independent position. tSCS was delivered using a 2.5 cm round electrode placed midline on the skin between the spinous processes of C4-C5, T11-T12, and/or L1-L2 as a cathode and two 5.0×10.2 cm$^2$ rectangular plates made of conductive plastic placed symmetrically on the skin over the iliac crests as anodes. Bipolar rectangular stimuli (1-msec duration) with a carrier frequency of 10 kHz and at intensities ranging from 30 to 200 mA were used. The stimulation was at 5 Hz and the exposure ranged from 10 to 30 sec. The threshold intensity of tSCS applied at T12 that induced involuntary stepping movements ranged from 110 to 180 mA. The same intensity was used during stimulation of C5 and/or L2. The strongest facilitation of stepping movements occurred when tSCS was applied at all three levels simultaneously. The multi-segmental stimulation of the cervical, thoracic, and lumbar spinal cord initiated stepping movements that had a short latency of initiation (~1 sec) and reached maximal amplitude within seconds. These data suggest that the synergistic and interactive effects of multi-site stimulation reflect the multi-segmental convergence of descending and ascending, and most likely propriospinal, influences on the spinal neuronal circuitry associated with locomotor activity. These data demonstrate the potential of a non-invasive means of stimulating the spinal cord, providing a new tool for modulating spinal locomotor circuitries and facilitating locomotion after a spinal cord injury.

EXAMPLE

Experimental Methods

Animal Study

Twelve adult female Sprague-Dawley rats (200-250 g body weight) underwent EMG and epidural stimulating electrode implantations and spinal cord transection surgeries. All experimental procedures were approved by the University of California Los Angeles Chancellor's Animal Research Committee and complied with the guidelines of the National Institutes of Health Guide for the Care and Use of Laboratory Animals.

Bipolar intramuscular EMG electrodes were implanted in the vastus lateralis (VL), semitendinosus (St), medial gastrocnemius (MG), and tibialis anterior (TA) muscles. Epidural electrodes were implanted at the L2 and S1 spinal segments. Spinal cord transection at T7-T8 was performed 14 days after the implantation of the EMG electrodes. Post-surgery, the bladders of all animals were expressed manually three times daily for the first two weeks and two times thereafter throughout the study. All of these procedures are performed routinely in our lab (Gerasimenko et al. (2007) J. Neurophysiol. 98:2525-2536). The rats were trained 5 days/week, 20 min/session for 3 weeks (15 training sessions) starting 7 days after the spinal cord transection surgery. The treadmill belt speed was increased progressively from 6 to 13.5 cm/s.

All rats were tested in the presence of epidural stimulation at spinal segments L2 or S1 (monopolar stimulation) or at L2 and S1 simultaneously at intensities of 2.5 to 3.5V. A stimulation frequency of 40 Hz with 200 μs duration rectangular pulses was used during monopolar stimulation. For simultaneous stimulation, the stimulation frequency at L2 was set to 40 Hz whereas the stimulation frequency at S1 varied (5, 10, 20, or 40 Hz).

Human Study

Figure 2:
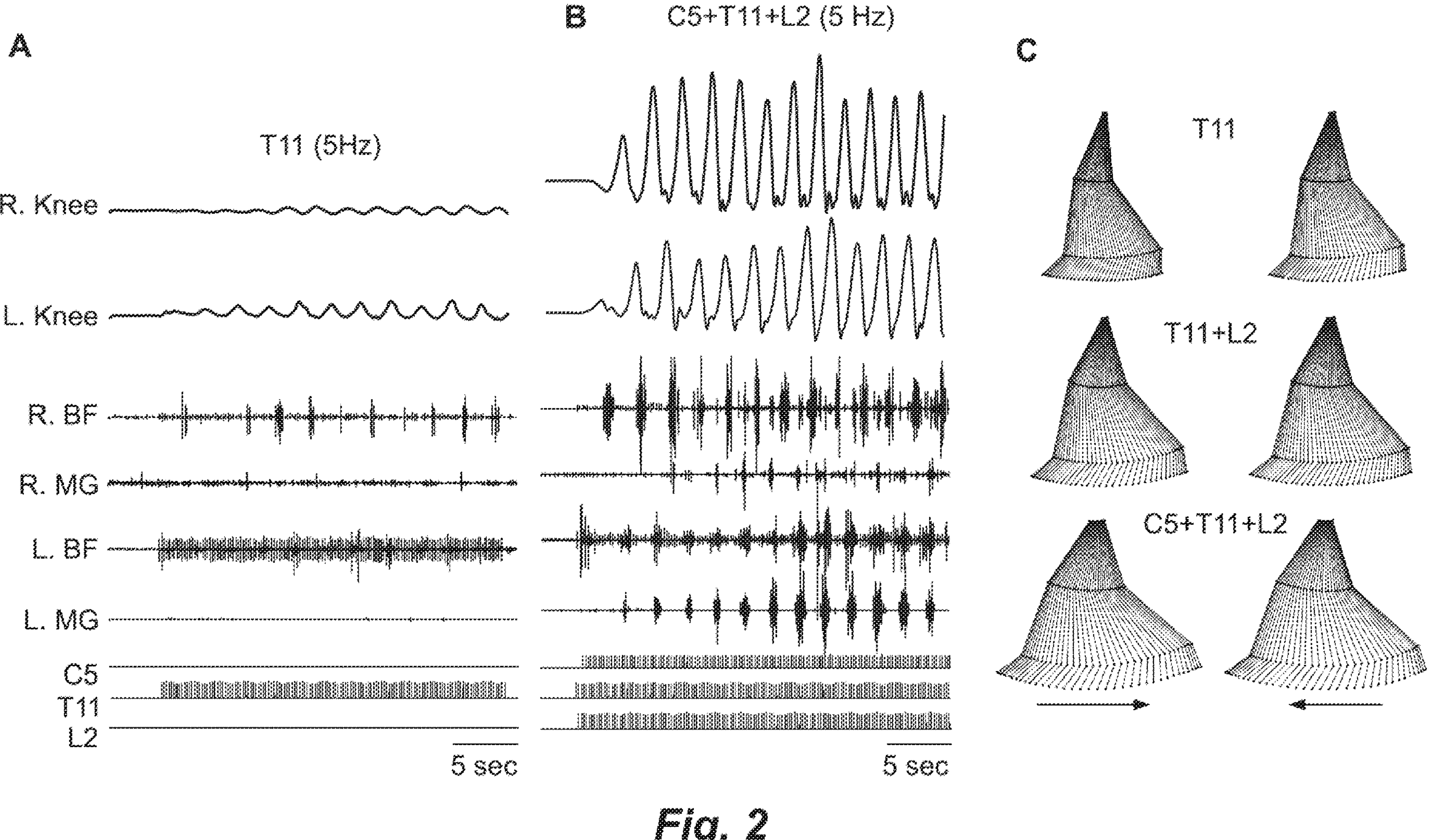
FIG. 2, panels A-C, provide an illustrative, but non-limiting, example of EMG and kinematic features of locomotor patterns induced by painless transcutaneous electrical spinal cord stimulation at the C5, T11, and L2 vertebral levels in non-injured human subjects. Panels A, B: Angular movements of the right (R) knee and left (L) knee joints and representative EMG activity in the biceps femoris (BF) and medial gastrocnemius (MG) muscles of the right (R) and left (L) legs during involuntary locomotor-like activity induced by transcutaneous spinal cord stimulation applied at the T11 vertebra alone (panel A) and at the C5+T11+L2 vertebrae simultaneously (panel B). Panel C: Stick diagram decompositions (40 ms between sticks) of the movements of the right leg during one step cycle during transcutaneous spinal cord stimulation at T11, T11+L2, and C5+T11+L2 simultaneously. Arrows indicate the direction of movement.

Six non-injured individuals participated in this study. The subjects were tested while lying on their right side with the upper leg supported directly in the area of the shank and the lower leg placed on a rotating brace attached to a horizontal board supported by vertical ropes secured to hooks in the ceiling as described previously (Gerasimenko et al. (2010) J. Neurosci. 30:3700-3708). The subjects were instructed not to voluntarily intervene with the movements induced by the stimulation. Painless transcutaneous electrical stimulation (PTES) was delivered using a 2.5 cm round electrode (Lead_Lok, Sandpoint, United States) placed midline on the skin between the spinous processes of C4-C5, T11-T12 and L1-L2 as a cathode and two 5.0×10.2 cm2 rectangular plates made of conductive plastic (Ambu, Ballerup, Germany) placed symmetrically on the skin over the iliac crests as anodes. Step-like movements were evoked by bipolar rectangular stimuli with 0.5 ms duration filled with a carrier frequency of 10 kHz and at an intensity ranging from 30 to 200 mA. The stimulation frequency was 5 Hz and the duration of exposure ranged from 10 to 30 s. Bilateral EMG activity was recorded from the biceps femoris, and medial gastrocnemius muscles throughout the entire testing period using bipolar surface electrodes. EMG signals were amplified by a ME 6000 16-channel telemetric electroneuromyograph (MegaWin, Finland). Flexion-extension movements at the knee joints were recorded. (training sessions) starting 7 days after the using goniometers. Reflective markers were placed bilaterally on the lateral epicondyle of the humerus, greater trochanter, lateral epicondyle of the femur, lateral malleolus, and hallux. Kinematics measures of leg movements were recorded using the Qualisy video system (Sweden). A single step cycle during stable stepping is illustrated to show the coordination between joint movements (FIG. 2, panel C).

Example 3

Effects of Combinations of Epidural Stimulation on Hindlimb EMG Activity in Spinal Rats Among all combinations of epidural stimulation parameters used to evoke bipedal stepping in spinal rats, simultaneous stimulation at L2 (40 Hz) and S1 (5-15 Hz) produced the most coordinated and robust EMG stepping pattern in the hindlimb muscles. FIG. 1 shows the mean (14 steps/condition) peak EMG amplitudes of the antigravity muscle, in response to different combinations of epidural stimulation in a spinal rat. The peak amplitudes of filtered raw EMG signals from the same rat were 25-fold higher in all hindlimb muscles when tested during simultaneous epidural stimulation at L2 (40 Hz) and S1 (20 Hz) compared to L2 monopolar stimulation.

Example 4

PTES-Induced Involuntary Locomotor-Like Activity in Human Subjects

PTES was easily tolerated by subjects and did not cause pain even when the strength of current was increased to 200 mA. Lack of pain can be attributed to the use of biphasic stimuli with a carrier frequency of 10 kHz that suppresses the sensitivity of pain receptors. The threshold intensity of the stimulus that induced involuntary stepping movements ranged from 110 to 180 mA. PTES at a frequency of 5 Hz applied to T11 alone caused step-like movements in five out of the six tested subjects (see FIG. 2, panel A). The involuntary stepping movements induced by PTES were reflected in the alternating EMG bursting activity in symmetric muscles of the left and right legs as well as the alternation of the EMG bursts in antagonist muscles of the hip and shank. These movements were further facilitated with simultaneous stimulation at either C5 or L2. The strongest facilitation of stepping movements occurred when PTES was applied at all three levels simultaneously (see FIG. 2, panel B).

The multi-segmental stimulation of the cervical, thoracic, and lumbar spinal cord initiated stepping movements had a short latency of initiation (~1 sec) and reached maximal amplitude within sec (see FIG. 2, panel B). Importantly, immediately after simultaneous PTES of the cervical, thoracic, and lumbar spinal cord, the right and left knees moved in opposite directions clearly reflecting a distinct alternating stepping pattern (see FIG. 2, panel C). Although the kinematics (joint angles, trajectory characteristics) of the lower limb movements were qualitatively similar during PTES at T11, T11+L2, or C5+T11+L2, stimulation at the three spinal levels simultaneously produced flexion-extension movements with larger amplitudes than stimulation at either one or two segments (see FIG. 2, panel C).

The obtained results from both spinal rats and human subjects suggest that simultaneous spinal cord stimulation at multiple sites has an interactive effect on the spinal neural circuitries responsible for generating locomotion. Thus, in some embodiments, simultaneous multisite epidural stimulation with specific parameters can allow for a more precise control of these postural-locomotor interactions, resulting in robust, coordinated plantar full weight-bearing stepping in complete spinal rats. For example, the EMG stepping pattern during simultaneous multi-site epidural stimulation was significantly improved compared to bipolar stimulation between L2 and S1 or monopolar stimulation at L2 or S1 (FIG. 1). An added benefit of second-site (S1 added to L2) stimulation with specific parameters may be related to activation of postural neuronal circuitries and activation of rostrally projecting propriospinal neurons from the more caudal segments that contribute to the rhythm and pattern of output of the locomotor circuitry.

In some embodiments, accessing the lumbosacral locomotor circuitry can be accomplished using the present methods in a noninvasive, pain-free procedure. In other embodiments of the present methods, PTES applied to the same level of the spinal cord is also able to activate locomotor circuitry. In still other embodiments, the present methods can use multi-segmental non-invasive electrical spinal cord stimulation to facilitate involuntary, coordinated stepping movements.

Further, the present methods can provide synergistic and interactive effects of stimulation in both animals and humans. This synergistic and interactive effect can result from a multi-segmental convergence of descending and ascending, for example, propriospinal, influences on the spinal neuronal circuitries associated with locomotor and postural activity.

Example 5

In other embodiments, stepping movements can be enhanced when the spinal cord is stimulated at two to three spinal levels (e.g., C5, T12, and/or L2) simultaneously.

Figure 3:
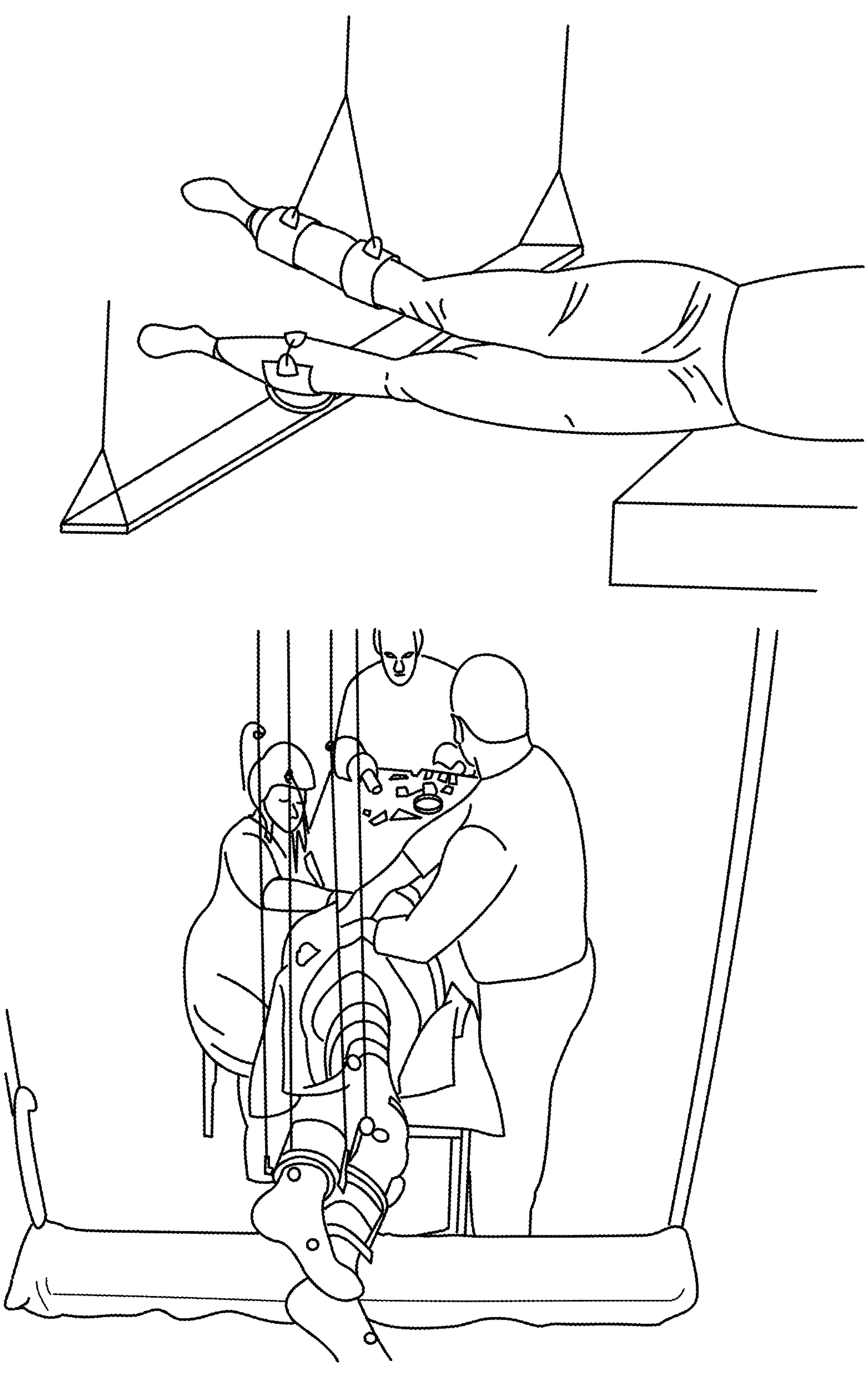
FIG. 3 is one example embodiment illustrating the positioning of test subjects.

The subjects were tested while lying on their right side with the upper leg supported directly in the area of the shank and the lower leg placed on a rotating brace attached to a horizontal board supported by vertical ropes secured to hooks in the ceiling (FIG. 3). The subjects were instructed not to voluntarily intervene with the movements induced by the stimulation. Painless transcutaneous electrical stimulation (PTES) was delivered using a 2.5 cm round electrode (Lead_Lok, Sandpoint, United States) placed midline on the skin between the spinous processes of C4-C5, T11-T12 and L1-L2 as a cathode and two 5.0×10.2 $cm^2$ rectangular plates made of conductive plastic (Ambu, Ballerup, Germany) placed symmetrically on the skin over the iliac crests as anodes. Step-like movements were evoked by bipolar rectangular stimuli with 0.5 ms duration filled with a carrier frequency of 10 kHz and at an intensity ranging from 30 to 200 mA. The stimulation frequency was 5 Hz and the duration of exposure ranged from 10 to 30 s.

Figure 4:
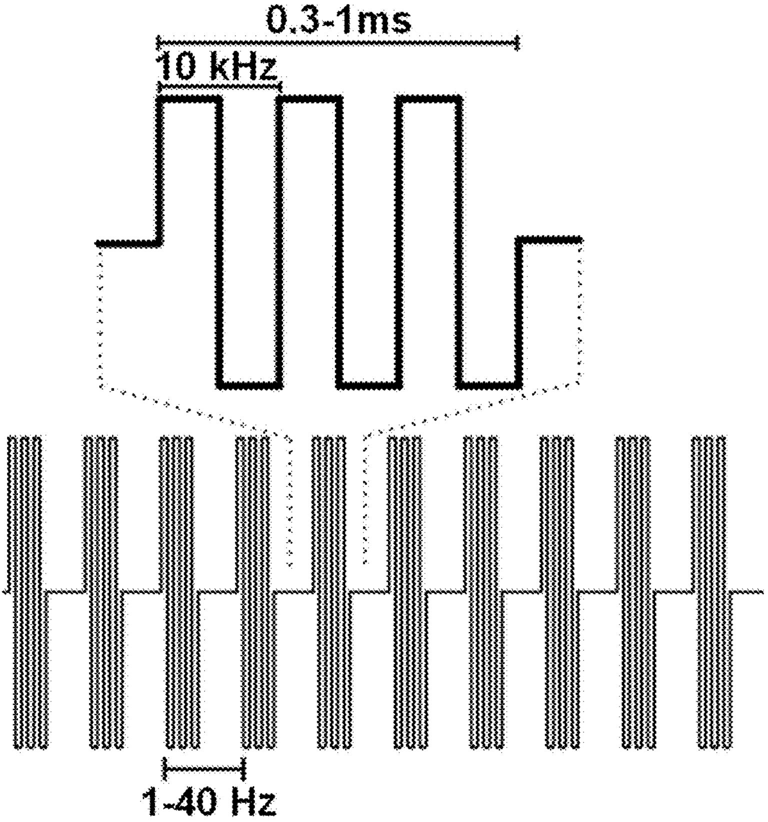
FIG. 4 is one example embodiment illustrating a graph depicting a 10 kHz biphasic stimulation is delivered in 0.3 to 1 ms. These pulses are delivered at 1-40 Hz.

TES was easily tolerated by subjects and did not cause pain even when the strength of current was increased to 200 mA. Lack of pain can be attributed to the use of biphasic stimuli with a carrier frequency of 10 kHz that suppresses the sensitivity of pain receptors. The threshold intensity of the stimulus that induced involuntary stepping movements ranged from 110 to 180 mA (FIG. 4).

Figure 5A:
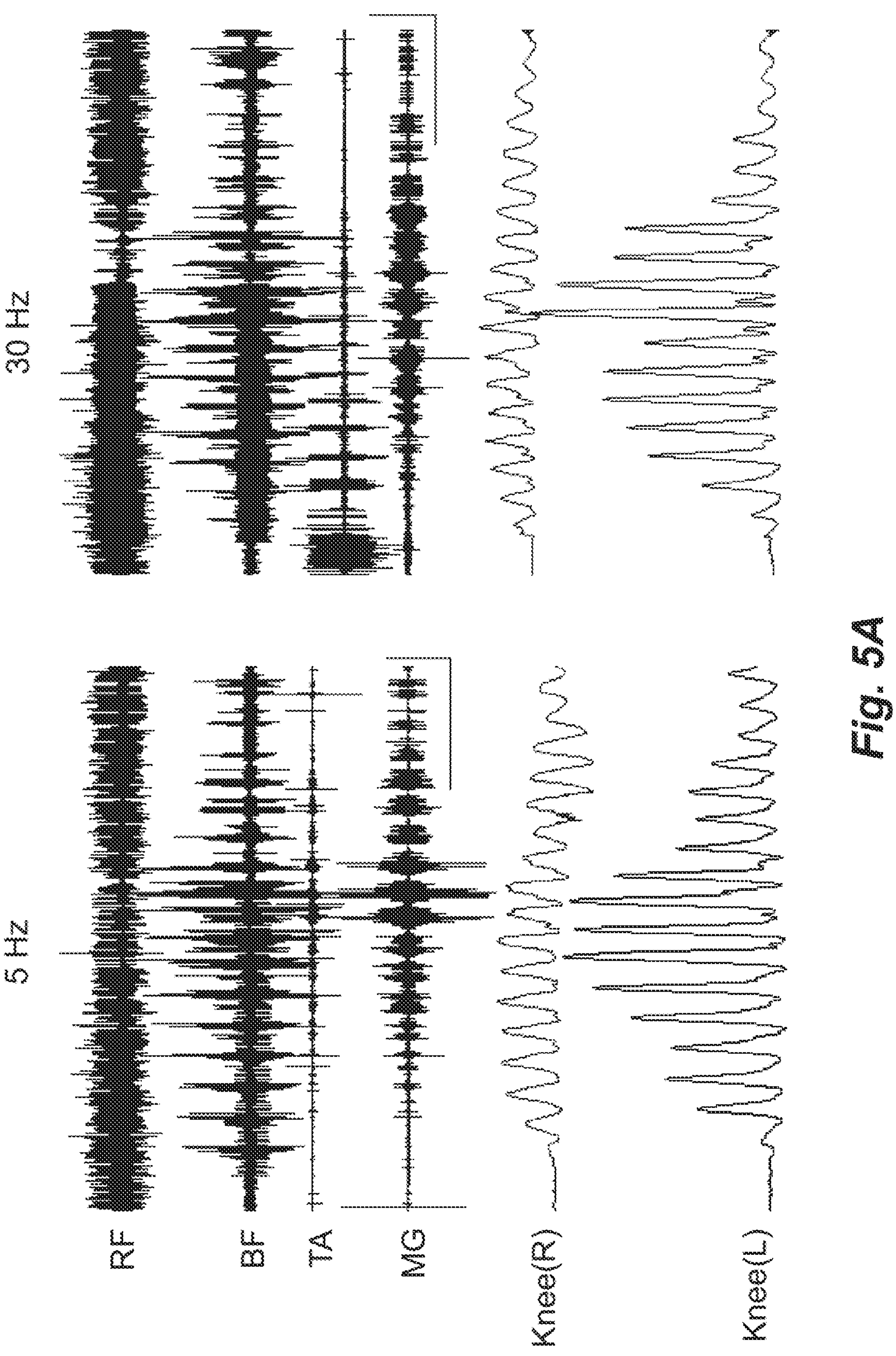
FIGS. 5A and 5B are examples of an embodiment illustrating EMG and kinematic features of locomotor patterns induced by painless transcutaneous electrical spinal cord stimulation at the T11-T12 vertebral level at 5 and 30 Hz of frequency in non-injured human subjects.
Figure 5B:
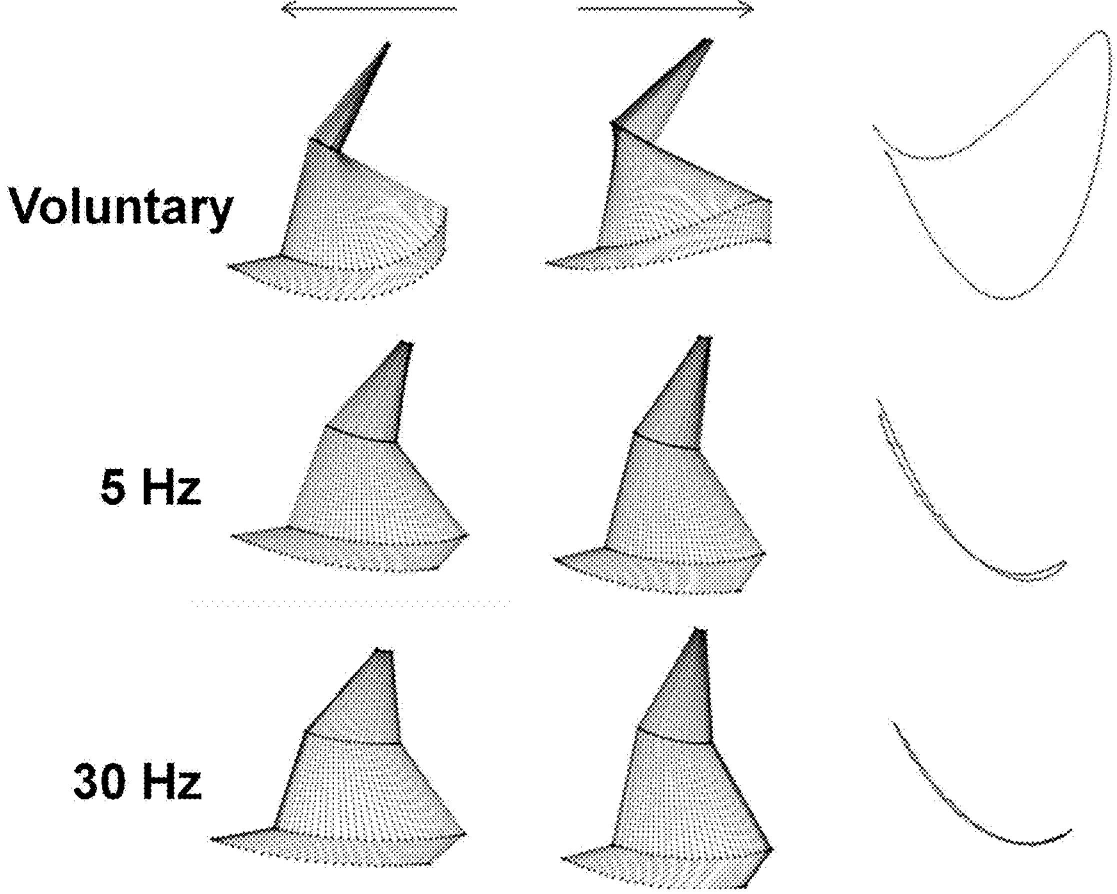

MG and kinematics features of locomotor patterns induced by painless transcutaneous electrical stimulation at the T11-T12 vertebral level at 5 and 30 Hz of frequency in non-injured human subjects are shown in FIGS. 5A and 5B. Angular movements of the right (R) knee and left (L) knee joints and representative EMG activity in the rectus femoris (RF), biceps femoris (BF) tibialis anterior (TA) and medial gastrocnemius (MG) muscles during involuntary locomotor-like activity induced by PTES at the T11 vertebra. Stick diagram decompositions (40 ms between sticks) of the movements of the R leg and trajectory of toe movements during one step cycle during PTES at T11-T12 are shown in FIG. 5B. Arrows in FIG. 5B indicate the direction of movement.

Figure 6:
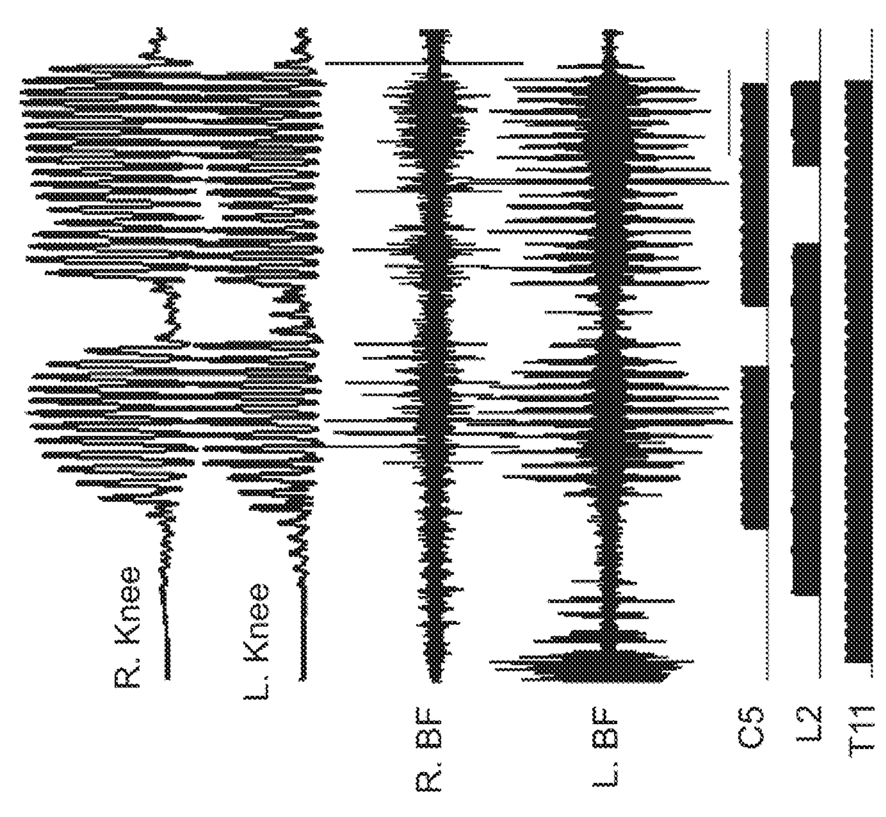
FIG. 6 is an example of one embodiment illustrating EMG and kinematic features of locomotor patterns induced by transcutaneous spinal cord stimulation at the C5, T11, and L2 vertebral levels. Angular movements of the right (R) knee and left (L) knee joints and representative EMG activity in the biceps femoris (BF) muscles of the R and left L legs during involuntary locomotor-like activity induced by transcutaneous spinal cord stimulation at the C5+T11+L2 vertebrae simultaneously (left) and sequentially (right).
Figure 6:
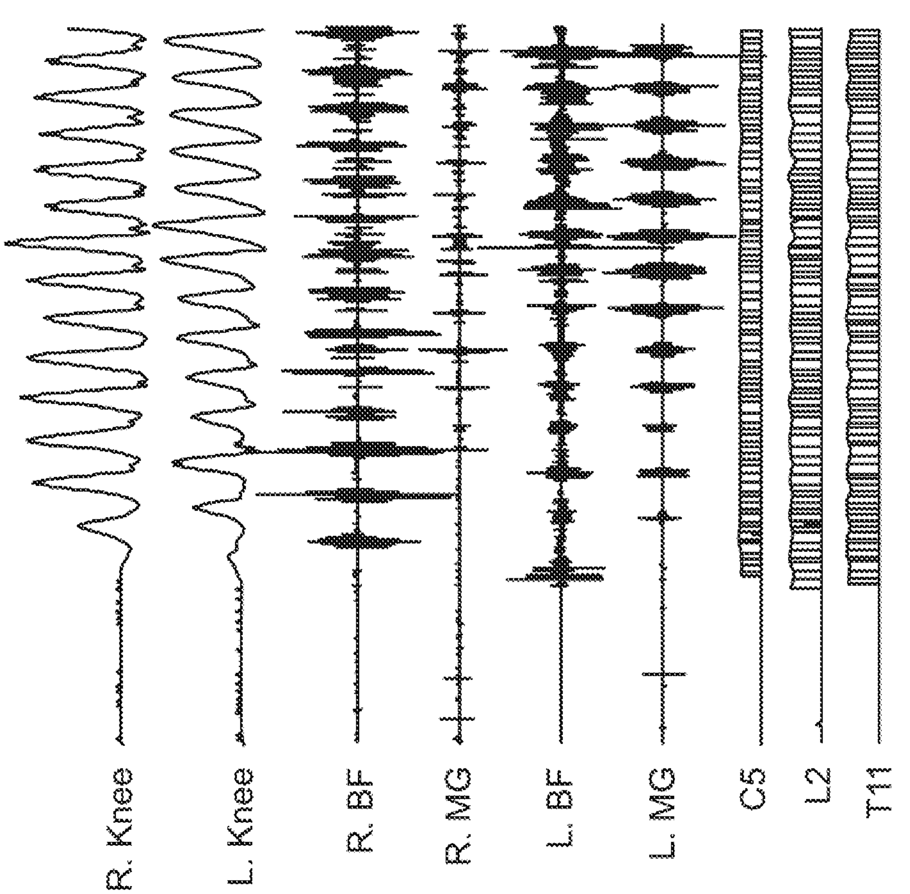

EMG and kinematics features of locomotor patterns induced by PTES at the C5, T11, and L2 vertebral levels (FIG. 6). Angular movements of the right (R) knee and left (L) knee joints and representative EMG activity in the biceps femoris (BF) muscles of the R and left L legs during involuntary locomotor-like activity induced by PTES at the C5+T11+L2 vertebrae simultaneously (left) and sequentially (right).

Figure 7:
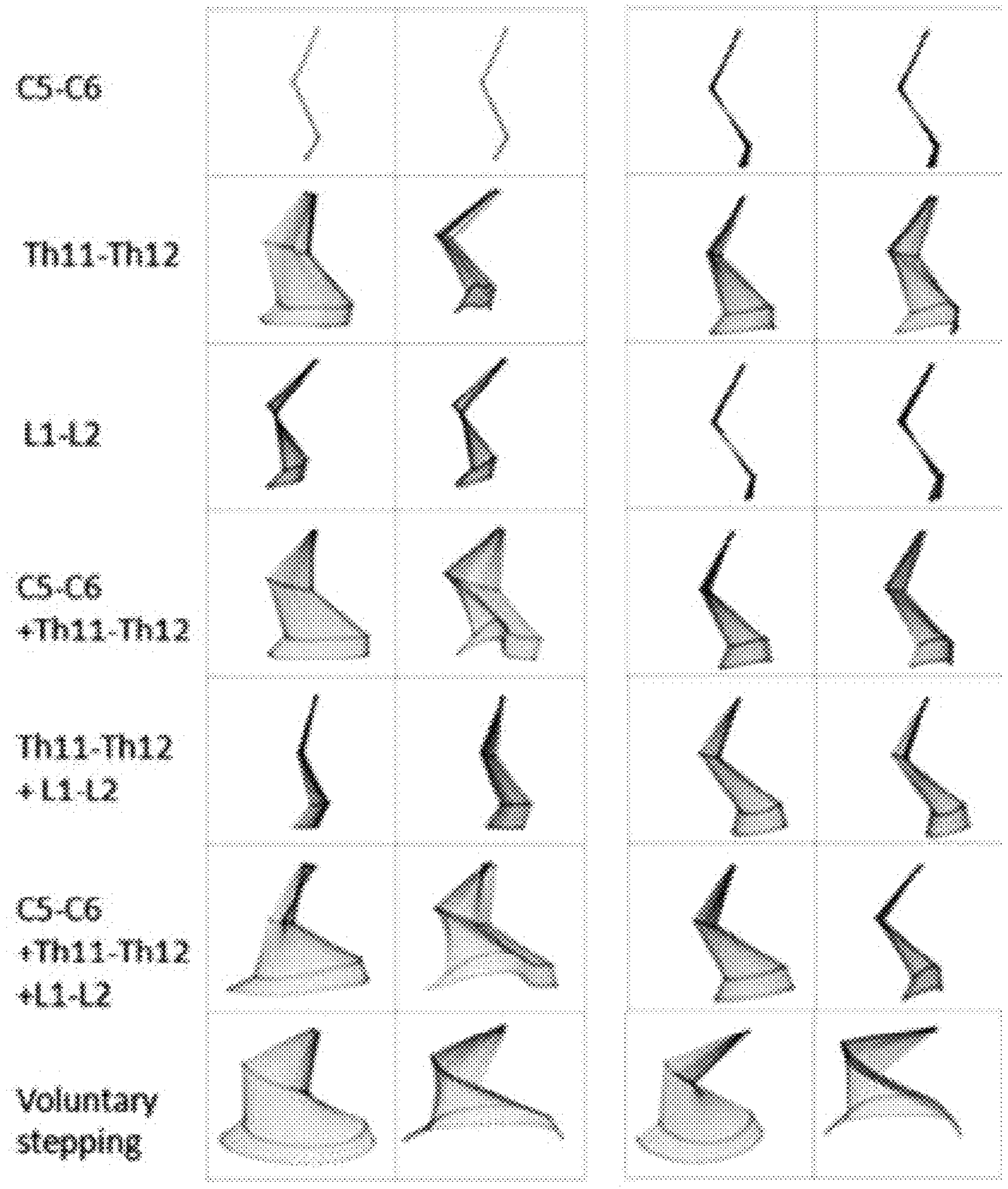
FIG. 7 is an example of one embodiment illustrating stick diagram decompositions (40 ms between sticks) of the movements of the R leg during one step cycle during transcutaneous spinal cord stimulation at different vertebral levels in two subjects are shown. Arrows indicate the direction of movement.

FIG. 7 shows stick diagram decompositions (40 ms between sticks) of the movements of the R leg during one step cycle during PTES at different vertebral levels in two subjects are shown. Arrows indicate the direction of movement. Multi-segmental non-invasive electrical spinal cord stimulation was used to facilitate involuntary, coordinated stepping movements. Simultaneous spinal cord stimulation at multiple sites can have an interactive effect on the spinal neural circuitries responsible for generating locomotion. The synergistic and interactive effects of multi-site spinal cord stimulation can be a multi-segmental convergence of descending and ascending, and most likely propriospinal, influences on the spinal circuitries associated with locomotor and postural activity.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A system for stimulation of the spinal cord to improve and restore upper extremity motor function in a subject having paralysis due to a spinal cord injury, the system comprising:

a multichannel stimulation generator;

an electrode array connectable to the stimulation generator and comprising a plurality of electrodes configured to be applied to the skin of the subject over a predetermined spinal section of the subject's spinal cord;

wherein the stimulation generator comprises control circuitry configured to administer to the subject a transcutaneous electrical spinal cord stimulation (tSCS) through one or more electrodes of the electrode array at a frequency and intensity to activate spinal locomotor networks that facilitates the recovery or improved voluntary movement of the arms without directly activating muscle cells;

wherein the transcutaneous electrical spinal cord stimulation enables or induces improved control of movement of the upper limbs of the subject.

2. The system of claim 1, wherein the transcutaneous electrical spinal cord stimulation is adjustable for each electrode for at least one of waveform, amplitude, frequency, pulse width, phase or polarity.

3. The system of claim 1, wherein the transcutaneous electrical spinal cord stimulation is applied over the spinal cord over the cervical portion of the spinal cord.

4. The system of claim 3, wherein the transcutaneous electrical spinal cord stimulation is applied over the spinal cord over one or more of C1-C7.

5. The system of claim 1, wherein the transcutaneous electrical spinal cord stimulation is applied over the spinal cord over at least one of T1-T12.

6. The system of claim 1, wherein the transcutaneous stimulation is applied at an intensity ranging from about 30 mA to 200 mA.

7. The system of claim 1, wherein the transcutaneous stimulation is applied at a frequency ranging from about 3 Hz to about 100 Hz.

8. The system of claim 1, wherein the stimulation generator has a portable form factor.

9. The system of claim 1, wherein the subject has a spinal cord injury that is clinically classified as motor complete.

10. The system of claim 1, wherein the subject has a spinal cord injury that is clinically classified as motor incomplete.

11. The system of claim 1, further comprising a return electrode connectable to the stimulation generator.

12. The system of claim 1, wherein the control circuitry is configured to use or receive instructions from a programmer.

13. The system of claim 12, wherein the stimulation generator is configurable by software and wherein the control circuitry has control parameters that may be programmed.

14. The system of claim 13, wherein the control parameters are downloaded from a remote site.

15. The system of claim 1, wherein the transcutaneous electrical spinal cord stimulation is superimposed on a carrier frequency that suppresses the sensitivity of pain receptors.

16. The system of claim 15, wherein the carrier frequency is about 10 kHz.

17. The system of claim 1, wherein the transcutaneous electrical spinal cord stimulation additionally facilitates at least one autonomic function.

18. A method for treating a subject having paralysis due to a spinal cord injury, the method comprising:

applying stimulation of the spinal cord using the system of claim 1; and providing physical trainings to the subject.

19. The method of claim 18, wherein the physical trainings generate at least one of proprioceptive signals or supraspinal signals.

20. The method of claim 18, wherein the physical training comprises robotically guided training.

21. The method of claim 18, wherein the physical training comprises inducing a positional change in the arms of the subject.

22. The method of claim 21, wherein the positional change comprises reaching.

23. The method of claim 21, wherein the positional change comprises grasping.

24. The system of claim 1, wherein the control stimulation generator is configured to provide transcutaneous electrical spinal cord stimulation to at least one electrode at a location along the spinal cord below a spinal injury of the subject relative to the patient's brain.

25. The system of claim 1, further comprising a plurality of electrode arrays.

26. The system of claim 1, wherein the electrode array comprises one or more lead of one or more electrodes.

* * * * *